US009650616B2

(12) United States Patent
Hannah et al.

(10) Patent No.: US 9,650,616 B2
(45) Date of Patent: May 16, 2017

(54) METHODS FOR INCREASING GRAIN YIELD

(71) Applicant: University of Florida Research Foundation, Inc., Gainesville, FL (US)

(72) Inventors: Larkin Curtis Hannah, Gainesville, FL (US); Janine R. Shaw, Gainesville, FL (US); Susan Kim Boehlein, Gainesville, FL (US); Jon Dale Stewart, Gainesville, FL (US); Bradford T. Sullivan, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 14/711,517

(22) Filed: May 13, 2015

(65) Prior Publication Data

US 2015/0329839 A1    Nov. 19, 2015

Related U.S. Application Data

(60) Provisional application No. 62/000,173, filed on May 19, 2014.

(51) Int. Cl.
*C12N 15/82* (2006.01)
*C12N 9/12* (2006.01)

(52) U.S. Cl.
CPC ........... *C12N 9/1241* (2013.01); *C12N 15/82* (2013.01); *C12N 15/8245* (2013.01); *C12N 15/8271* (2013.01); *C12Y 207/07027* (2013.01)

(58) Field of Classification Search
None
See application file for complete search history.

(56) References Cited

U.S. PATENT DOCUMENTS

| | | |
|---|---|---|
| 5,589,618 A | 12/1996 | Hannah et al. |
| 5,650,557 A | 7/1997 | Hannah et al. |
| 5,872,216 A | 2/1999 | Hannah et al. |
| 6,069,300 A | 5/2000 | Hannah et al. |
| 6,184,438 B1 | 2/2001 | Hannah |
| 6,403,863 B1 | 6/2002 | Hannah et al. |
| 6,809,235 B2 | 10/2004 | Hannah et al. |
| 6,969,783 B2 | 11/2005 | Hannah et al. |
| 7,173,165 B2 | 2/2007 | Hannah et al. |
| 7,312,378 B2 | 12/2007 | Hannah et al. |
| 8,362,321 B2 | 1/2013 | Hannah et al. |
| 8,536,407 B2 | 9/2013 | Hannah et al. |
| 8,710,298 B2 | 4/2014 | Hannah et al. |
| 8,802,926 B2 | 8/2014 | Hannah et al. |
| 2003/0056248 A1 | 3/2003 | Hannah et al. |
| 2005/0177901 A1 | 8/2005 | Zhu et al. |
| 2008/0319927 A1 | 12/2008 | Dallmier et al. |
| 2010/0199385 A1 | 8/2010 | Hannah et al. |

FOREIGN PATENT DOCUMENTS

WO   WO 2011/019391   2/2011

OTHER PUBLICATIONS

Chen et al 1996 Plant Mol. Biol. 32:999-1001, sequence alignment provided in action.*
U.S. Appl. No. 61/857,546, filed Jul. 23, 2013, Hannah et al.
Boehlein et al., "Purification and characterization of adenosine diphosphate glucose pyrophosphorylase from maize/potato mosaics," *Plant Physiol* 138:1552-1562, 2005.
Boehlein et al., "Heat stability and allosteric properties of the maize endosperm ADP-glucose pyrophosphorylase are intimately intertwined," *Plant Physiol* 146:289-299, 2008.
Boehlein et al., "Studies of the kinetic mechanism of maize endosperm ADP-glucose pyrophosphorylase uncovered complex regulatory properties," *Plant Physiol* 152:1056-64, 2010.
Boehlein et al., "Probing allosteric binding sites of the maize endospermADP-glucose pyrophosphorylase," *Plant Physiol.*, 152:85-95, 2010.
Boehlein et al., "Deciphering the kinetic mechanisms controlling selected plant ADP-glucose pyrophosphorylases," *Arch Biochem Biophys*, 535:215-226, 2013.
Boehlein et al., "Enhancing the heat stability and kinetic parameters of the maize endosperm ADP-glucose pyrophosphorylase using iterative saturation mutagenesis," *Arch Biochem Biophys* 568:28-37, 2015.
Genbank Accession No. AAC49942 dated Mar. 9, 1998.
Genbank Accession No. AAK27727 dated Oct. 31, 2005.
Genbank Accession No. AAS00542 dated Feb. 1, 2004.
Genbank Accession No. ACF77017 dated Aug. 3, 2008.
Genbank Accession No. AF030383 dated Nov. 18, 1999.
Genbank Accession No. AF030384 dated Nov. 18, 1999.
Genbank Accession No. AF356003 dated Apr. 29, 2002.
Genbank Accession No. AFL55396 dated Jun. 11, 2012.
Genbank Accession No. AFL55397 dated Jun. 11, 2012.
Genbank Accession No. AFL55398 dated Jun. 11, 2012.
Genbank Accession No. AFL55399 dated Jun. 11, 2012.
Genbank Accession No. D50317 dated Feb. 19, 2008.
Genbank Accession No. JE0132 dated Mar. 15, 2004 (replaced by O22659).
Genbank Accession No. JE0133 dated Mar. 15, 2004 (replaced by O22658).
Genbank Accession No. M81603 Apr. 23, 1997.
Genbank Accession No. NP 001106017 dated May 30, 2015.
GenBank Accession No. O22658 dated Oct. 31, 2006.
GenBank Accession No. O22659 dated Oct. 31, 2006.
GenBank Accession No. O48877 dated Oct. 31, 2006.
GenBank Accession No. O04924 dated Nov. 28, 2006.
Genbank Accession No. P12299 dated Jun. 24, 2015.
Genbank Accession No. P55233 May 27, 2015.
Genbank Accession No. P55242 dated Jun. 24, 2015.
GenBank Accession No. P93230 dated Nov. 28, 2006.
GenBank Accession No. P93430 dated Nov. 28, 2006.

(Continued)

*Primary Examiner* — Brent Page
(74) *Attorney, Agent, or Firm* — Dentons US LLP

(57) ABSTRACT

Compositions and methods for increasing heat resistance or starch biosynthesis in plants are provided herein. Polynucleotides, polypeptides, and expression constructs for expressing mutant AGPase subunit proteins, plants comprising the polynucleotides, polypeptides or expression constructs, and methods of producing transgenic plants are also provided.

19 Claims, 12 Drawing Sheets

(56) References Cited

OTHER PUBLICATIONS

Genbank Accession No. T03445 dated Jun. 18, 1999 (replaced by O48877).
Genbank Accession No. T04156 dated May 11, 2000 (replaced by P93430).
Genbank Accession No. T07674 dated May 11, 2000 (replaced by P93230).
Genbank Accession No. T07682 dated May 11, 2000 (replaced by O04924).
Genbank Accession No. U66041 dated Dec. 17, 1996.
Genbank Accession No. U66876 dated May 28, 1997.
Genbank Accession No. X61187 dated Aug. 28, 1996.
Genbank Accession No. X67151 dated Oct. 7, 1996.
Genbank Accession No. X76136 dated Jul. 20, 1995.
Genbank Accession No. X96766 dated Sep. 21, 1998.
Genbank Accession No. Z38111 dated Oct. 31, 1995.
Giroux et al., "A single mutation that increases maize seed weight," *Proc Natl Acad Sci USA* 93:5824-5829, 1996.
Iglesias et al., "Expression of the potato tuber ADP-glucose pyrophosphorylase in *Escherichia coli*," *J. Biol. Chem* 268:1081-1086, 1993.
Jin et al., "Crystal structure of potato tuber ADP-glucose pyrophosphorylase," *EMBO J* 24:694-704, 2005.
Reetz et al., "Iterative saturation mutagenesis (ISM) for rapid directed evolution of functional enzymes," *Nature Prot* 2:891-903, 2007.
Sullivan et al., "Library construction and evaluation for site saturation mutagenesis," *Enzyme Microb Technol* 53(1):70-77, 2013.
International Search Report and Written Opinion regarding International Application No. PCT/US2015/030604, dated Feb. 2, 2016.

\* cited by examiner

| Common Name | Scientific Name | SEQ ID NO. | GenBank Accession Number |
|---|---|---|---|
| Maize | Zea mays | 40 | M81603 (Sh2) |
| | | 41 | Z38111 |
| | | 42 | NP_001106017 |
| Barley | Hordeum vulgare | 43 | X67151 |
| | | 44 | U66876 |
| Sorghum | Sorghum bicolor | 45 | T03445 |
| Rice | Oryza sativa | 46 | T04156 |
| | | 47 | AAK27727 |
| | | 48 | U66041 |
| | | 49 | D50317 |
| Wheat | Triticum aestivum | 50 | P12299 |
| Tomato | Lycopersicon esculentum | 51 | T07674 |
| | | 52 | T07682 |
| | | 53 | AAC49942 |
| Potato | Solanum tuberosum | 54 | X76136 |
| | | 55 | X61187 |
| | | 56 | P55242 |
| Sweet Potato | Ipomoea batatas | 57 | AFL55396 |
| | | 58 | AFL55397 |
| | | 59 | AFL55398 |
| | | 60 | AFL55399 |
| Sweet orange | Citrus sinensis | 61 | ACF77017 |
| Pea | Pisum sativum | 62 | X96766 |
| Strawberry | Fragaria x ananassa | 63 | AAS00542 |
| Beet | Beta vulgaris | 64 | P55233 |
| Chickpea | Cicer arietinum | 65 | AF356003 |
| Watermelon | Citrullus lanatus | 66 | JE0132 |
| | | 67 | JE0133 |
| Muskmelon | Cucumis melo | 68 | AF030383 |
| | | 69 | AF030384 |

FIG. 1

```
Sequence Alignment

Maize_SH2-M81603              ---MQFA--LALDTNSGPHQIR-SCEGDGIDR-LEKLSIGGRKQEKALRN 43
Sorghum-T03445                ---MQFS--LASDANSGPHPIRRSCEGGGIDR-LERLSIGGSKQEKALRN 44
Rice-T04156                   ---MQFM--MPLDTNACAQPMRRAGEGAGTERLMERLNIGGMTQEKALRK 45
Rice-AAK27727                 ---MEFM--MPLDTNACAQPMRRAGEGAGTERLMERLNIGGMTQEKALRK 45
Rice-U66041                   ---MQFM--MPLDTNACAQPMRRAGEGAGTERLMERLNIGGMTQEKALRK 45
Maize_Agp1-Z38111             ---MQFSSVLPLEGKACMSPVRRGSGGYGSER-MRIN-CCSIRRNKALRR 45
Rice-D50317                   ---MQFSSVFPLEGKACVSPIRRGGEGSASDR-LKIGDSSSIKHDRAVRR 46
Barley-X67151                 MSSMQFSSVLPLEGKACVSPVRR--EGSACER-LKIGDSSSIRHERASRR 47
Wheat-P12299                  MSSMQFSSVLPLEGKACISPVRR--EGSASER-LKVGDSSSIRHERASRR 47
Maize_Agp1lzm                 ----MGLRVAATAPAPAGVRVLGRGAARVTPRPW------AAVGGRR--- 37
Barley-U66876                 ----MDLRVAAPASVAAAARRGALGCARVRP----------LQGRRQ-- 33
Sweet_Potato-AFL55399         ----MAVTADGRIALLAARQLREGAAMTVSSCRLSVKFCNGEFMGKKIKL 46
Tomato-T07674                 ----MSVATDVRFALLRN----NPAALTGTNLKI-VKFCNGELMGKKLKY 41
Potato-X76136                 ------------------------------------------MGKKLKY 7
Sweet_Potato-AFL55396         -----MEFCPTLKSSAHLPR---------ETEFFGGRIRGSLNNNVLASK 36
Sweet_Potato-AFL55397         ----MDAYCATLKSTTHLPR---------ESELWG---KRMLKTSVVVNQ 34
Tomato-T07682                 ----MDTCCAAMKSTVHLGRVSTGGFNNGEKEIFGEKIRGSLNNNLRINQ 46
Potato-X61187                 --------------------------------------------------
Watermelon-JE0133             -MVAMDSCFVSLKSNTHLMKGNWGGLDRCENGFYGEKVRGSFNENAWIKS 49
Muskmelon-AF030383            -MVAMDSCFVSLKSNTQLMKGNWGGLDRCENGFMVEKVRGGFNENVWIKS 49
Citrus_sinensis-ACF77017      ----MDSCCVGLRANTHVVKASKYGSKIGDNALWGERIRGSVSNDGCTKQ 46
Pea-X96766                    ----MASGCVSLKTNTHFPNSKK-------GSFFGERIKGSLKNSSWVTT 39
Fragaria_x_ananassa-AAS00542  ----MDSWCVTLKPNTHLRQPTQAGLCCGANGFLGQRIRESFGNRGWVHG 46
Sweet_Potato-AFL55398         ----MDALCASMRAHPVPVSKGFG---YGDSGLWGEKIRGCSRIKTER-- 41
Tomato-AAC49942               ----MDALCA---GTAQSVAICN-----QESTFWGQKISGRRLINKGFGV 38
Potato-P55242                 ----MDALCASMKGTAQLVAICN-----QESAFWGEKISGRRLINKGFGV 41
Beet-P55233                   ----MDASAAAINVNAHLTEVGKK---RFLGERISQSLKGKDLR-ALFSR 42
Chickpea-AF356003             ---------MDLAIGSNYASLRSS---VFLGETLKGNLSTKFLTSPKFSQ 38
Watermelon-JE0132             --------------------------------------------------
Muskmelon-AF030384            ----------MHKISSQEKNQCFG---FWGDSSLGRNGRWKQIQRNASSR 37
```

FIG. 1 (continued)

```
Maize_SH2-M81603              RCFGG---------RVAATTQCILTSDACP-ETLHSQTQSSRKNYADANR 83
Sorghum-T03445                RCFGG---------RVAATTQCILTSDACP-ETLHFQTQSSRKSYADANH 84
Rice-T04156                   RCFGD---------GVTGTARCVFTSDADR-DTPHLRTQSSRKNYADASH 85
Rice-AAK27727                 RCFGD---------GVTGTARCVFTSDADR-DTPHLRTQSSRKNYADASH 85
Rice-U66041                   RCFGD---------GVTGTARRVFTSDADR-DTPHLRTQFSRKNYADASH 85
Maize_Agp1-Z38111             MCFSA-------RGAVS-STQCVLTSDAGP-DTLVVRT-SFRRNYADPNE 85
Rice-D50317                   MCLGY-------RGTKN-GAQCVLTSDAGP-DTLHVRT-SFRRNFADPNE 86
Barley-X67151                 MCNGGA------RGPAATGAQCVLTSDASPADTLVLRT-SFRRNYADPNE 90
Wheat-P12299                  MCNGG-------RGPAATGAQCVLTSDASPADTLVLRT-SFRRNYADPNE 89
Maize_Agp1lzm                 -RFSVRMS------VATTE-ATTTIAVGASE---DQALEAR-----NSKT 71
Barley-U66876                 CRPSVRVS------VATTESAAAAAAVSASA---DEDAETT-----NPRT 69
Sweet_Potato-AFL55399         RKFQQRNGTKYNVVARPRVSMSLTTDVAGEAKLKDYGMEKT-----DPRT 91
Tomato-T07674                 TKFQLRSN-----VVKPHICMSLTTDIAGEAKLKDLEAKKE-----DART 81
Potato-X76136                 TKFQLRSN-----VVKPNICMSLTTDIAGEAKLKDLERQKKG----DART 48
Sweet_Potato-AFL55396         SRKSLRVDGNKR-KIKPGVAFSVLTRENGTETLTVEAPILER-RRANPKN 84
Sweet_Potato-AFL55397         FGKSLKLERNGR-KIKPGVAFSVLTRETGRETLSVEAPRLER-VRANPKN 82
Tomato-T07682                 LSKSLKLE---K-KIKFGEAYSVITIENDTETVFVDMPRLER-RRANPKD 91
Potato-X61187                 -----------N-KIKPGVAYSVITTENDTQTVFVDMPRLER-RRANPKD 37
Watermelon-JE0133             LKS----EKKAL-KLTPNVAYAVATPNISKQPVSIQVPSIPK-VKANPKN 93
Muskmelon-AF030383            LKY----EKKAL-KLTPNVAYAVT-PNVSKQPMTIQVPTVPK-VKANPKN 92
Citrus_sinensis-ACF77017      LKKSLKAEKRDE-KVKPGVAYAVMTSKHPNEVMTLAPPRLER-RRVDPKN 94
Pea-X96766                    QKK-----------IKPASFSAILTSDDPKGSLNLQVPSFLR-LRADPKN 77
Fragaria_x_ananassa-AAS00542  SE-----------KTRPGVVSSVV--TTKDFETTLKVPTYHR-PRVDPKN 82
Sweet_Potato-AFL55398         ---HEGMPKKVN-LGVACSILTHDIN---KEHLSFETQHFEEHSQGDPRN 84
Tomato-AAC49942               RWCKSFTTQQRG-RGVTSAVLTRDIN---KEMLPFENSMFEEQPTADPKA 84
Potato-P55242                 RSCKSFTTQQRG-RNVTPAVLTRDIN---KEMLPFEESMFEEQPTADPKA 87
Beet-P55233                   TESKGRNVNKP---GVAFSVLTSDFNQSVKESLKYEPALFES-PKADPKN 88
Chickpea-AF356003             IHINNLRSFNPR-NGASYSVLTSGINDFEESMTFHEGPYFDT-PKADPKS 86
Watermelon-JE0132             -NSNSSPRSTAR-KLTPGVAYSVLMSEISEVSSTLQAPIFET-PRADPKK 47
Muskmelon-AF030384            NNSDSSSSRAR-SLHPELLILFSCSEVNEETTTLQAPIFEA-PRADPKK 85
```

FIG. 1 (continued)

| | | |
|---|---|---|
| Maize_SH2-M81603 | VSAI<u>LGGGTGSQLFPLT</u>STRATPAVPVGGCYRLIDIPMSNCFNSGINK- | 132 |
| Sorghum-T03445 | VSAIILGGGTGSQLFPLTSTRATPAVPVGGCYRLIDIPMSNCFNSGINK- | 133 |
| Rice-T04156 | VSAVILGGGTGVQLFPLTSTRATPAVPVGGCYRLIDIPMSNCFNSGINK- | 134 |
| Rice-AAK27727 | VSAVILGGGTGVQLFPLTSTRATPAVPVGGCYRLIDIPMSNCFNSGINK- | 134 |
| Rice-U66041 | VSAVILGGGTGVQLFPLTRTRATPAVPVGGCYRLIDIPMSNCFNSGINKN | 135 |
| Maize_Agp1-Z38111 | VAAVILGGGTGTQLFPLTSTRATPAVPIGGCYRLIDIPMSNCFNSGINK- | 134 |
| Rice-D50317 | VAAVILGGGTGTQLFPLTSTRATPAVPIGGCYRLIDIPMSNCFNSGINK- | 135 |
| Barley-X67151 | VAAVILGGGTGTQLFPLTSTRATPAVPIGGCYRLIDIPMSNCFNSGINK- | 139 |
| Wheat-P12299 | VAAVILGGGTGTQLFPLTSTRATPAVPIGGCYRLIDIPMSNCFNSGINK- | 138 |
| Maize_Agpl1zm | VVAVILGGGAGTRLFPLTRRRAKPAVPIGGAYRLIDVPMSNCINSGINK- | 120 |
| Barley-U66876 | VVAVILGGGAGTRLFPLTKRRAKPAVPIGGAYRLIDVPMSNCINSGINK- | 118 |
| Sweet_Potato-AFL55399 | VVAIILGGGAGTRLFPLTKRRAKPAVPIGGAYRLIDVPMSNCINSGINK- | 140 |
| Tomato-T07674 | VVAIILGGGGGTRLFPLTKRRAKPAVPIGGAYRLIDVPMSNCINSGINK- | 130 |
| Potato-X76136 | VVAIILGGGAGTRLFPLTKRRAKPAVPMGGAYRLIDVPMSNCINSGINK- | 97 |
| Sweet_Potato-AFL55396 | VAAIILGGGAGTQLFPLTNRAATPAVPLGGCYRLIDIPMSNCINSGVNK- | 133 |
| Sweet_Potato-AFL55397 | VAAIILGGGAGTQLFPLTNRAATPAVPVGGCYRMIDIPMSNCINSGINK- | 131 |
| Tomato-T07682 | VAAVILGGGEGTKLFPLTSRTATPAVPVGGCYRLIDIPMSNCINSAINK- | 140 |
| Potato-X61187 | VAAVILGGGEGTKLFPLTSRTATPAVPVGGCYRLIDIPMSNCINSAINK- | 86 |
| Watermelon-JE0133 | VASIILGGGAGTHLFPLTRRSATPAVPVGGCYRLIDIPMSNCINSGINK- | 142 |
| Muskmelon-AF030383 | VASIILGGGAGTHLFPLTKRSATPAVPAGGCYRLIDIPMSNCINSGINK- | 141 |
| Citrus_sinensis-ACF77017 | VAAIILGGGAGTKLFPLTLRAATPAVPVAGCYRLIDIPMSNCINSGINK- | 143 |
| Pea-X96766 | VISIVLGGGPGTHLYPLTKRAATPAVPVGGCYRLIDIPMSNCINSGINK- | 126 |
| Fragaria_x_ananassa-AAS00542 | VASIILGGGAFTQLFPLTRRAATPAVPVGGCYRLIDIPMSNCINSNINK- | 131 |
| Sweet_Potato-AFL55398 | VASIVLGGGAGTRLFPLTRSRAKPAVPIGGCYRLIDVPMSNCINSGIRK- | 133 |
| Tomato-AAC49942 | VASVILGGGVGTRLFPLTSRRAKPAVPIGGCYRLIDVPMSNCINSGIRK- | 133 |
| Potato-P55242 | VASVILGGGVGTRLFPLTSRRAKPAVPIGGCYRLIDVPMSNCINSGIRK- | 136 |
| Beet-P55233 | VAAIVLGGGAGTRLFPLTSRRAKPAVPIGGCYRLIDVPMSNCINSGIRK- | 137 |
| Chickpea-AF356003 | VASIILGGGAGTRLFPLTSKRAKPAVPIGGCYRLIDVPMSNCINSGIRK- | 135 |
| Watermelon-JE0132 | IASIILGGGAGTRLFPLTSQRAKPAVPIGGCYRLIDIPMSNCINSGIEK- | 96 |
| Muskmelon-AF030384 | VASIILGGGAGTRLFPLTSQRAKPAVPIGGCYRLIDIPMSNCINSGIEK- | 134 |

FIG. 1 (continued)

```
Maize_SH2-M81603              IFVMSQFNSTSLNRHIHRTY-LEGGINFADGSVQVLAATQMPEEPA-GWF 180
Sorghum-T03445                IFVMTQFNSTSLNRHIHRTY-LGGEINFADGSVQVLADTQMPEEPD-GWF 181
Rice-T04156                   IFVMTQFNSASLNRHIHHTY-LGGGINFTDGSVQVLAATQMPDEPA-GWF 182
Rice-AAK27727                 IFVMTQFNSASLNRHIHHTY-LGGGINFTDGSVQVLAATQMPDEPA-GWF 182
Rice-U66041                   IFVMTQFNLTSLNRNIHHTY-LVGGINLTDGSVQVLAATQMPDEPA-GWF 183
Maize_Agp1-Z38111             IFVMTQFNSASLNRHIHRTY-LGGGINFTDGSVEVLAATQMPGEAA-GWF 182
Rice-D50317                   IFIMTQFNSASLNRHIHRTY-LGGGINFTDGSVEVLAATQMPGEAA-GWF 183
Barley-X67151                 IFVMTQFNSASLNRHIHRTY-LGGGINFTDGSVEVLAATQMPGEAA-GWF 187
Wheat-P12299                  IFVMTQFNSASLNRHIHRTY-LGGGINFTDGSVEVLAATQMPGEAA-GWF 186
Maize_Agpl1zm                 VYILTQFNSQSLNRHLSRAYDFSNGVAIGDGFVEVLAATQRPGTEGKRWF 170
Barley-U66876                 VYVLTQFNSASLNRHLFRAYNFSNGVGFGDGFVEVLAATQRPGSEGKRWF 168
Sweet_Potato-AFL55399         VYILTQFNSASLNRHLARAYNFGSGVTFGDGYVEVLAATQTPGEAGKRWF 190
Tomato-T07674                 VYILTQFNSASLNRHIARAYNFGNGVTFGDGYVEVLAATQTPGELGKRWF 180
Potato-X76136                 VYILTQFNSASLNRHIARAYNFGNGVTFESGYVEVLAATQTPGELGKRWF 147
Sweet_Potato-AFL55396         IFVLTQFNSASLNRHISRTY-FGNGVSFGDGFVEVLAATQTQGETGMKWF 182
Sweet_Potato-AFL55397         IFVLTQFNSASLNRHIARTY-FGNGVSFGDGFVEVLAATQTSGETGMKWF 180
Tomato-T07682                 IFVLTQYNSAALNRHIARTY-FGNGVSFGDGFVEVLAATQTPGEAGKKWF 189
Potato-X61187                 IFVLTQYNSAPLNRHIARTY-FGNGVSFGDGFVEVLAATQTPGEAGKKWF 135
Watermelon-JE0133             IFVLTQFNSASLNRHISRTY-FGNGVNFGEGFVEVLAATQTSGETGMHWF 191
Muskmelon-AF030383            IFVLTQFNSASLNRHISRTY-FGNGVTFKEGFVEVLAATQTSGESGMYWF 190
Citrus_sinensis-ACF77017      IFVLTQFNSASLNRHIARTY-FGNGTNFGDGFVEVLAATQTPGESGKNWF 192
Pea-X96766                    IFVLTQFNSASLNRHIARTY-FGNGVNFGDGFVEVLAATQTPGEAGKKWF 175
Fragaria_x_ananassa-AAS00542  IFVLTQFNSTSLNRHLARTY-FGNGINFGDGFVEVLAATQTSGEAGMDWF 180
Sweet_Potato-AFL55398         IFILTQFNSFSLNRHLARAYGIGNGVNFGDGFVEVLAATQTPGEAGKMWF 183
Tomato-AAC49942               IFILTQFNSFSLNRHLARTYNFGNGVGFGDGFVEVLAATQTPGDAGKMWF 183
Potato-P55242                 IFILTQFNSFSLNRHLA-TYNFGNGVGFGDGFVEVLAGTQTPGDGRKMWF 185
Beet-P55233                   IFILTQFNSFSLNRHLARTYNFGDGVNFGDGFVEVFAATQTPGESGKKWF 187
Chickpea-AF356003             IFILTQFNSFSLNRHLSRSYNFGNVSTFGEGFVEVLAATQTSGEAGKKWF 185
Watermelon-JE0132             IFVLTQFNSFSLNRHLARIYNFGNGVNFGDGFVEVLAATQTSGETGKKWF 146
Muskmelon-AF030384            ISSN-AVNSFSLNRHLARIYNFGNGVNFGDGFVEVLAATQTSGETGKKWF 183
```

FIG. 1 (continued)

```
Maize_SH2-M81603              QGTADSIRKFIWVLEDYYSHKSIDNIVILSGDQLYRMNYMELVQKHVEDD 230
Sorghum-T03445                QGTADSVRKFIWVLEDYYNHKSIEHIVILSGDQLYQMNYMELVQKHVEDN 231
Rice-T04156                   QGTADAIRKFMWILEDHYNQNNIEHVVILCGDQLYRMNYMELVQKHVDDN 232
Rice-AAK27727                 QGTADAIRKFMWILEDHYNQNNIEHVVILCGDQLYRMNYMELVQKHVDDN 232
Rice-U66041                   QGTADAIRKFMWILEDHIHKS-IDNIVILCGDQLYRMNYMELVQKHVDTN 232
Maize_Agp1-Z38111             QGTADAVRKFIWVLEDYYKHKAIEHILILSGDQLYRMDYMELVQKHVDDN 232
Rice-D50317                   QGTADAVRKFIWVLEDYYKHKAIEHILILSGDQLYRMDYMELVQKHVDDN 233
Barley-X67151                 RGTADAVRKFIWVLEDYYKHKSIEHILILSGDQLYRMDYMELVQKHVDDN 237
Wheat-P12299                  RGTADAVRKFIWVLEDYYKNKSIEHILILSGDQLYRMDYMELVQKHVDDN 236
Maize_Agpl1zm                 QGTADAVRQFDWLFDD-AKSKDIEDVLILSGDHLYRMDYMDFVQSHRQRG 219
Barley-U66876                 QGTADAVRQFAWLFDD-AKSKDIEDVLILSGDHLYRMDYMDFVQSHRQRD 217
Sweet_Potato-AFL55399         QGTADAVRQFHWLFED-PKSKDIEDVLILSGDHLYRMDYMDFVQSHRQSG 239
Tomato-T07674                 QGTADAVRQFHWLFED-ARSKDIEDVLILSGDHLYRMDYLHFVQSHRQSG 229
Potato-X76136                 QGTAHAVRQFHWLFED-ARSKDIEDVLILSGDHLYRMDYLHFVQSHRQSG 196
Sweet_Potato-AFL55396         QGTADAVRQFTWVFED-AKNKDIDNIVILSGDQLYRMDYMDLVQNHIERN 231
Sweet_Potato-AFL55397         QGPADAVRKFTWVFED-AKNKDIENILILSGDQLYRMDYMDLVQNHLDRN 229
Tomato-T07682                 QGTADAVRKFIWVFED-AKNKNIENILVLSGDHLYRMDYMELVQNHIDRN 238
Potato-X61187                 QGTADAVRKFIWVFED-AKNKNIENIVVLSGDHLYRMDYMELVQNHIDRN 184
Watermelon-JE0133             QGTADAVRQFIWVFED-AKNRNVENILILAGDHMYRMDYMDFVQNHIDRN 240
Muskmelon-AF030383            QGTADAVRQFIWVFED-AKNRNVENILILAGDHMYRMGYMDFVQNHIDRN 239
Citrus_sinensis-ACF77017      QGTADAVRQFTWVFED-AKNRNIENVAILCGDHLYRMDYMDFIQSHVDRD 241
Pea-X96766                    QGTADAVRQFTWIFED-AKNINVENVLILAGDHLYRMDYMDLLQSHVDRN 224
Fragaria_x_ananassa-AAS00542  QGTADAVRQFVWVFED-AKNRNVENILILSGDHLYRMDYMDFVQSHVDSN 229
Sweet_Potato-AFL55398         QGTADAVRQFIWVFED-AKNKNIDNILILSGDHLYRMDYMDFVQRHIDTN 232
Tomato-AAC49942               QGTADAVRQFIWVFEN-QKNKNVEHIIILSGDHLYRMNYMDFVQKHIDAN 232
Potato-P55242                 Q-AADAVREFIWVFEN-QKNKNVEHIIILSGDHLYRMNYMDFVQKHIDTN 233
Beet-P55233                   QGTADAVRQFFWAFED-SKSKDVEHIVILSGDHLYRMDYMSFWQKHIDTN 236
Chickpea-AF356003             QGTADAVRQFIWVFED-AKTKNVEHILILSGDHLYRMNYMDFVQKHIDTN 234
Watermelon-JE0132             QGTADAVRQFIWLFED-AKTKNVEHTLILSGDHLYRMDYMDFVQRHIDTN 195
Muskmelon-AF030384            QGTADAVRPFIWLFED-AQTKNVEHTLILSGDHLYRMDYMDFVQRHIDTN 232
```

FIG. 1 (continued)

```
Maize_SH2-M81603            ADITISCAPVDESRASKNGLVKIDHTGRVLQFFEKPKGADLNSMRVETNF 280
Sorghum-T03445              ADITVSCAPVDESRASNNGLVKCDHTGRVLQFFEKPKGADLNSMRVDTNF 281
Rice-T04156                 ADITISCAPIDGSRASDYGLVKFDDSGRVIQFLEKPEGADLESMKVDTSF 282
Rice-AAK27727               ADITISCAPIDGSRASDYGLVKFDDSGRVIQFLEKPEGADLESMKVDTSF 282
Rice-U66041                 ADITISCAPIDGSRASDYGLVKFDHSGRVIQFLEKPEGADLESM-VDTSF 281
Maize_Agp1-Z38111           ADITLSCAPVGESRASDYGLVKFDSSGRVIQFSEKPKGAALEEMKVDTSF 282
Rice-D50317                 ADITLSCAPVGESRASDYGLVKFDSSGRVIQFSEKPKGTDLEAMKVDTSF 283
Barley-X67151               ADITLSCAPVGESRASEYGLVKFDSSGRVIQFSEKPKGDDLEAMKVDTSF 287
Wheat-P12299                ADITLSCAPVGESRASEYGLVKFDSSGRVVQFSEKPKGDDLEAMKVDTSF 286
Maize_Agp1lzm               AGISICCLPIDGSRASDFGLMKIDDTGRVISFSEKPKGDELKAMQVDTTV 269
Barley-U66876               AGISICCLPIDDSRASDFGLMKIDDTGRVISFSEKPKGADLKAMQVDTTL 267
Sweet_Potato-AFL55399       ADITISSLPIDDRRASDFGLMKIDDKGRVLFFSEKPKGDDLKAMAVDTSV 289
Tomato-T07674               ADITISSLPIDDSRASDFGLMKIDDTGRVMSFSEKPKGDDLKAMAVDTTV 279
Potato-X76136               ADITISSLPIDDSRASDFGLMKIDDTGRVMSFSEKPKGDDLKAMAVDTTV 246
Sweet_Potato-AFL55396       SDITLSCATVGDSRASDFGLVKIDRRGRVVQFCEKPKGTDLKAMQVDTTL 281
Sweet_Potato-AFL55397       SDITLSCAPVGDSRAVDFGLVKIDRRGKVVQFQEKPKGADLEAMQVDTTR 279
Tomato-T07682               ADITLSCAPAEDSRASDFGLVKIDSRGRVVQFAEKPKGFDLKAMQVDTTL 288
Potato-X61187               ADITLSCAPAEDSRASDFGLVKIDSRGRVVQFAEKPKGFDLKAMQVDTTL 234
Watermelon-JE0133           ADISISCAAVGDSRASDYGLVKIDSRGRIIQFSEKPMGANLSAMRVDTTS 290
Muskmelon-AF030383          ADISISCAAVDDSRASDYGLVKLDSRGRIIQFSEKPKGANLNRMRVDTTS 289
Citrus_sinensis-ACF77017    ADITISCAAVGESRASDYGLVKIDNMGRIAQFAEKPSGANLKAMQVDTSL 291
Pea-X96766                  ADITVSCAAVGDNRASDYGLVKVDDRGNIIQFSEKPKGADLKAMQVDTSR 274
Fragaria_x_ananassa-AAS00542 ADITLSCAVVGDSRASDYGLVKIDSRGKIIQFAEKPRGAGLKAMQSDTTL 279
Sweet_Potato-AFL55398       ADITVSCVPMDDSRASDYGLMKIDGSGRIVHFAEKPKGPALKTMQVDTSL 282
Tomato-AAC49942             ADITVSCVPMDDGRASDFGLMKIDETGRIIQFAEKPKGPALKVMQVDTSI 282
Potato-P55242               ADITVSCVPMDDGRASDFGLMKIDETGAIIQFAEKPKGPALKAMQVDTSI 283
Beet-P55233                 ADITVSCIPMDDSRASDYGLMKIDHTGRIVHFAEKPKGSDLTAMQVDTTV 286
Chickpea-AF356003           ADITVSCIPMDDSRASDYGLLKIDGKGRIIQFAEKPKGSELKAMRVDTTL 284
Watermelon-JE0132           ADITVSCIPMDDSRASDYGLMKIDDTGRILHFAEKPKGSDLEAMKVDTTV 245
Muskmelon-AF030384          ADITVSCIPMDDSRASDYGLMKIDDTGRIIHFSEKPKGSDLEEMQVDTAV 282
```

FIG. 1 (continued)

```
Maize_SH2-M81603              LSYAIDDAQKYPYLASMG-IYVFKKDALLDLLKSKYTQLHDFGSEILPRA 329
Sorghum-T03445                LSYAIGDAQKYQYIASMG-IYVFKKDALLDLLKSKYTQLHDFGSEILPRA 330
Rice-T04156                   LSYAIDDKQKYPYIASMG-IYVLKKDVLLDILKSKYAHLQDFGSEILPRA 331
Rice-AAK27727                 LSYAIDDKQKYPYIASMG-IYVLKKDVLLDILKSKYAHLQDFGSEILPRA 331
Rice-U66041                   LSYAIDDKQKYPYIASMG-IYVLKKDVLLDILKSKYAHLQDFGSEILPRA 330
Maize_Agp1-Z38111             LNFAIDSPAEYPYIASMG-VYVFKRDVLLDLLKSRYAELHDFGSEILPKA 331
Rice-D50317                   LNFAIDDPTKFPYIASMG-VYVFKRDVLLNLLKSRYAELHDFGSEILPRA 332
Barley-X67151                 LNFAIDDPAKYPYIASMG-VYVFKRDVLLNLLKSRYAELHDFGSEILPRA 336
Wheat-P12299                  LNFAIDDPAKYPYIASMG-VYVFKRDVLLNLLKSRYAELHDFGSEILPRA 335
Maize_Agp1lzm                 LGLSKEEAENKPYIASMG-IYIFKKDILLNLLRWRFPTANDFGSEIIPAS 318
Barley-U66876                 LGLPKEEAEKKPYIASMG-VYIFKKEILLNLLRWRFPTANDFGSEIIPAA 316
Sweet_Potato-AFL55399         LGLSPEEAKQKPYIASMG-VYVFKKEILLNLLRWRFPTANDFGSEIIPAS 338
Tomato-T07674                 LGLSPEEAKEKPYIASMG-VYVFKKDILLNLLRWRFPTVNDFGSEIIPAS 328
Potato-X76136                 LGLSPEEAKEKPYIASIGKVYVFKKDILLNLLRWRFPTANDFGSEIIPAS 296
Sweet_Potato-AFL55396         LGLPPQDARLNPYIASMG-VYVFKTDVLLRLLRWRYPTSNDFGSEILPAA 330
Sweet_Potato-AFL55397         LGLSPEDAKRNPYIASMG-LYVFRRDLLLNLLRWIYPTANDFGSEIIPAV 328
Tomato-T07682                 VGLSPQDAKKSPYIASMG-VYVFKTDVLLKLLKWSYPTSNDFGSEIIPAA 337
Potato-X61187                 VGLSPQDAKKSPYIASMG-VYVFKTDVLLKLLKWSYPTSNDFGSEIIPAA 283
Watermelon-JE0133             FGLSREESLKSPYIASMG-VYVFKTDILLNLLKWRYPTSNDFGSEIIPAA 339
Muskmelon-AF030383            FGLSREESLKSPYIGSMG-VYVFKTDVLLNLLKWRYPSSNDFGSEIIPAA 338
Citrus_sinensis-ACF77017      LGFSPQEARKCPYVASMG-VYVFKKDVLLKLLRWRYPTSNDFGSEIIPAA 340
Pea-X96766                    LGLSPQDALKSPYIASMG-VYVFKKDVLLKLLKWRYPTSNDFGSEIIPSA 323
Fragaria_x_ananassa-AAS00542  LGFSPQDALKSPYVASMG-VYVFKTDILLELLKKSYPNSNDFGSEIIPAA 328
Sweet_Potato-AFL55398         LGLSENEAKKYPYIASMG-VYVFRTEVLLNLLRSQYPSCNDFGSEIIPAA 331
Tomato-AAC49942               LGLSEQEASNFPYIASMG-VYVFKTDVLLKLLKSAYPSCNDFGSEIIPSA 331
Potato-P55242                 LGLSEQEASNFPYIASMG-VYVFKTDVLLNLLKSAYPSCNDFGSEIIPSA 332
Beet-P55233                   LGLSDLEAMSNPYIASMG-VYVFRTDVLMELLNRKYPSSNDFGSEIIPSA 335
Chickpea-AF356003             LGLSPEEAKKQPYIASMG-VYVFRTETLLKLLRSNCSTCNDFGSEIIPSA 333
Watermelon-JE0132             LGLSNQDARKNPYIASMG-VYIFRTDLLLKLLTWSYPSCNDFGSEIIPSA 294
Muskmelon-AF030384            LGLSDEDARKNPYIASMG-VYIFRTDLLLKLLTWSYPACNDFGSEIIPAA 331
```

FIG. 1 (continued)

| | | |
|---|---|---|
| Maize_SH2-M81603 | VLD-HSVQ-ACIFTGYWEDVGTIKSFFDANLALTEQPSKFDFYDPKTPFF | 377 |
| Sorghum-T03445 | VLE-HNVQ-TCIFMGYWEDVGTIKSFFDANLALTEQPSKFDFYDPKTPFF | 378 |
| Rice-T04156 | VLE-HNVK-ACVFTEYWEDIGTIKSFFDANLALTEQPPKFEFYDPKTPFF | 379 |
| Rice-AAK27727 | VLE-HNVK-ACVFTEYWEDIGTIKSFFDANLALTEQPPKFEFYDPKTPFF | 379 |
| Rice-U66041 | LLE-HNVKVACVFTEYWEDIGTIKSFFDANLALTEQPPKFEFYDPKTPFF | 379 |
| Maize_Agp1-Z38111 | LHE-HNVQ-AYVFTDYWEDIGTIRSFFDANMALCEQPPKFEFYDPKTPFF | 379 |
| Rice-D50317 | LHE-HNVQ-AYVFADYWEDIGTIRSFFDANMALCEQPPKFEFYDPKTPFF | 380 |
| Barley-X67151 | LHD-HNVQ-AYVFTDYWEDIGTIRSFFDANMALCEQPPKFEFYDPKTPFF | 384 |
| Wheat-P12299 | LHD-HNVQ-AYVFTDYWEDIGTIRSFFDANMALCEQPPKFEFYDPKTPFF | 383 |
| Maize_Agp1lzm | AKE-IDVKAY-LFNDYWEDIGTIKSFFEANLALAEQPPRFSFYDADKPMY | 366 |
| Barley-U66876 | ARE-INVKAY-LFNDYWEDIGTIKSFFEANLALAEQPSKFSFYDASKPMY | 364 |
| Sweet_Potato-AFL55399 | ARE-FYIQAY-LFNDYWEDIGTIRSFFEANLALTEHPPRFSFYDATKPIY | 386 |
| Tomato-T07674 | TKE-FCVKAYYLFNDYWEDIGTIRSFFEANLALTEHPPRFSFYDATKPIY | 377 |
| Potato-X76136 | TKE-FCVKAY-LFNDYWEDIGTIRSFFRANLALTEHPPRFSFYDATKPIY | 344 |
| Sweet_Potato-AFL55396 | VME-HNVQAY-IFRDYWEDIGTIKSFYDANLALTEEFPKFEFYDPKTPFY | 378 |
| Sweet_Potato-AFL55397 | ITE-HNVQAY-FFKDYWEDIGTIKTFYDANLALAEEFPKFEFYDPKTPFY | 376 |
| Tomato-T07682 | IDD-YNVQAY-IFKDYWEDIGTIKSFYNASLALTQEFPEFQFYDPKTPFY | 385 |
| Potato-X61187 | IDD-YNVQAY-IFKDYWEDIGTIKSFYNASLALTQEFPEFQFYDPKTPFY | 331 |
| Watermelon-JE0133 | VKE-HNVQAY-IFRDYWEDIGSIKTFYDANLALTEEFPKFEFYDPKTPIY | 387 |
| Muskmelon-AF030383 | IKD-HNVQAF-MFRDYWEDIGTIKTFYDANLALHGNVSKFEFYDPKTPFY | 386 |
| Citrus_sinensis-ACF77017 | IME-HDVQAY-IFRDYWEDIGTIKSFYEANMALTKESPAFHFYDPKTPFY | 388 |
| Pea-X96766 | IRE-HNVQAY-FFGDYWEDIGTIKSFYDANLALTEESPKFEFYDPKTPIF | 371 |
| Fragaria_x_ananassa-AAS00542 | VEE-RNVQAY-IFIDYWEDIGTIQSFYDANLALTEEFPKFQFYDPKTPFF | 376 |
| Sweet_Potato-AFL55398 | VKD-HNVQAY-LFSDYWEDIGTVKSFFDANLALTEQPPMFDFNDPKTPFY | 379 |
| Tomato-AAC49942 | VKD-HNVQAY-LFNDYWEDIGTVKSFFDANLALTKQPPKFDFNDPKTPFY | 379 |
| Potato-P55242 | VKD-HNVQAY-LFNDYWEDIGTVKSFFDANLALTKQPPKFDFNDPKTPFY | 380 |
| Beet-P55233 | VGE-SNVQAY-LFNDYWEDIGTIKSFFDSNLALTQQPPKFEFYDPKTPFY | 383 |
| Chickpea-AF356003 | VNDDHNVQAY-LFNDYWEDIGTIKSFFDANLALTDQPPKFQFYDPNTPFY | 382 |
| Watermelon-JE0132 | VKD-YKVQAY-LFNDYWEDIGTVKSFFDANLALTEQPPKFEFYDPKTPFY | 342 |
| Muskmelon-AF030384 | VKD-YKVQAY-LFNDYWEDIGTVKSFFDANLALTEQPPKFEFYDPKTPFY | 379 |

FIG. 1 (continued)

```
Maize_SH2-M81603              TAPRCLPPTQLDKCK--MKYAFISDGCLLRECNIEHSVIGVCSRVSSGCE 425
Sorghum-T03445                TAPRYLPPTQLDKCK--IKDASISDGCLLRECSIEHSVIGVCSRVSYGCE 426
Rice-T04156                   TSPRYLPPARLEKCK--IKDAIISDGCSFSECTIEHSVIGISSRVSIGCE 427
Rice-AAK27727                 TSPRYLPPARLEKCK--IKDAIISDGCSFSECTIEHSVIGISSRVSIGCE 427
Rice-U66041                   TSPRYLPPARLDKCKCKIKDAIISDGCSFSECTIEHSVIGISSRVSSGCE 429
Maize_Agp1-Z38111             TSPRYLPPTKSDKCR--IKDAIISHGCFLRECAIEHSIVGVRSRLNSGCE 427
Rice-D50317                   TSPRYLPPTKSDKCR--IKDAIISHGCLLRECTIGHSIVGVRSRLNSACE 428
Barley-X67151                 TSPRYLPPTKSDKCR--IKEAIISHGCFLRECKIEHSIIGVRSRLNSGSE 432
Wheat-P12299                  TSPRYLPPTKSDKCR--IKEAIISHGCFLRECKIEHSIIGVRSRLNSGSE 431
Maize_Agp1lzm                 TSRRNLPPSMVNNSK--ITDSIISHGCFLDNCRIEHSVVGVRSRIGSNVH 414
Barley-U66876                 TSRRNLPPSMISGSK--ITDSIISHGCFLDKCRVEHSVVGIRSRIGSNVH 412
Sweet_Potato-AFL55399         TSRRNLPPSAITNSK--IVDSIISHGSFLSDCFVEHSVVGIRSRINSNVH 434
Tomato-T07674                 TSRRNLPPSAIDNSK--IVDSIVSHGSFLTNCFVEHSVVGIRSRIGTNVH 425
Potato-X76136                 TSRRNLPPSAIDNSK--IVDSIVSHGIFLTNCFVEHSVVGIRSRIGTNVH 392
Sweet_Potato-AFL55396         TSPRFLPPTKIDNCK--IKDAIISHGCFLRECTVEHSIIGERSRLDCGVE 426
Sweet_Potato-AFL55397         TSPRFLPPTKIDNCK--IKDAIISHGCFLRECIVEHSIVGERSRLDFGVE 424
Tomato-T07682                 TSPRFLPPTKIDNCK--IKDAIISHGCFLRDCTVEHSIVGERSRLDCGVE 433
Potato-X61187                 TSPRFLPPTKIDNCK--IKDAIISHGCFLRDCSVEHSIVGERSRLDCGVE 379
Watermelon-JE0133             TSPRFLPPTKIDKCQ--IVDAIISHGCFLRECSVQHSIVGERSRLDYGVE 435
Muskmelon-AF030383            TSPRFLPPTKIDRCQ--IVDAIISHGCFLRECSIQHSIVGERSRLDYGVE 434
Citrus_sinensis-ACF77017      TSPRFLPPTKIDNCR--MKDAIISHGCFLRECTVEHSIVGERSRIDYGVE 436
Pea-X96766                    TSPGFLPPTKIDNSR--VVDAIISHGCFLRDCTIQHSIVGERSRLDYGVE 419
Fragaria_x_ananassa-AAS00542  TSPRFLPPTKIDNSR--VVDAIISHGCFLQECFVQSSIVGERSRLDYGVE 424
Sweet_Potato-AFL55398         TSPRFLPPTKVDKCK--IVDAIISHGCFLRECSVKHSIVGIRSRLDYGVE 427
Tomato-AAC49942               TSARFLPPTKVDKSR--IVDAIISHGGFLRECNIQHSIVGVRSRLDYGVE 427
Potato-P55242                 TSARFLPPTKVDKSR--IVDAIISHGCFLRECNIQHSIVGVRSRLDYGVE 428
Beet-P55233                   TSARFLPPTKVDRCK--IVDSIVSHGCFLQESSIQHSIVGVRSRLESGVE 431
Chickpea-AF356003             TFPRFLPPTKVEKCK--IVDAIISHGCFLRECSVQHSIVGIRSRLESGVE 430
Watermelon-JE0132             TSPRFLPPSKVEKCR--IVDAIISHGCFLRECSVEHSIVGVRSRLEYGVE 390
Muskmelon-AF030384            TSPRSCPPSKVEKCR--IVDAIISHGCFLRECTVEPLIVGVRSRLEYGVE 427
```

FIG. 1 (continued)

| | | |
|---|---|---|
| Maize_SH2-M81603 | LKDSVMMGADIYETEEEASKLLLAGKVPIGIGRNTKIRNCIIDMNARIGK | 475 |
| Sorghum-T03445 | LKDCVMMGADIYETEEEASKLLLAGEVPVGIGGNTKIRNCIIDINARIGK | 476 |
| Rice-T04156 | LKDTMMMGADQYETEEETSKLLFEGKVPIGIGENTKIRNCIIDMNARIGR | 477 |
| Rice-AAK27727 | LKDTMMMGADQYETEEETSKLLFEGKVPIGIGENTKIRNCIIDMNARIGR | 477 |
| Rice-U66041 | LK--------IYETEEETSKLLFEGKVPIGIGQNTKIRNCIIDMNARIGR | 471 |
| Maize_Agp1-Z38111 | LKNTMMMGADLYETEDEISRLLAEGKVPIGVGENTKISNCIIDMNARVGR | 477 |
| Rice-D50317 | LKNTMMMGADLYETEDEISRLLSEGKVPIGVGENTKINNCIIDMNARVGR | 478 |
| Barley-X67151 | LKNAMMMGADSYETEDEISRLMSEGKVPIGVGENTKISNCIIDMNARIGR | 482 |
| Wheat-P12299 | LKNAMMMGADSYETEDEISRLMSEGKVPIGVGENTKISNCIIDMNARIGR | 481 |
| Maize_Agp1lzm | LKDTVMLGADYYETAVERGELLAEGKVPIGIGENTTIQKCIIDKNARIGK | 464 |
| Barley-U66876 | LKDTVMLGADFYETDAERGDQLAEGKVPIGIGENTSIQNCIIDKNARIGK | 462 |
| Sweet_Potato-AFL55399 | LKDTVMLGADYYETGAEIASLLTEGGVPIGIGENSRIKECIIDKNARIGK | 484 |
| Tomato-T07674 | LKDTVMLGADYYETDAEIASQLAEGKVPLGIGENTRIKECIIDKNARIGK | 475 |
| Potato-X76136 | LKDTVMLGADYYETDAEIRSQLAEGKVPLGIGENTRIKDCIIDKNARIGK | 442 |
| Sweet_Potato-AFL55396 | LKDTLMMGADNYETESEIASLLADGKVPIGVGENTKIRNAIIDKNVRIGK | 476 |
| Sweet_Potato-AFL55397 | LKDTLMMGADYYETESEIASLLADGKVPIGIGHNTKISNCIIDKNVRIGK | 474 |
| Tomato-T07682 | LKDTFMMGADYYQTESEIASLLAEGKVPIGIGENTKIRKCIIDKNAKIGK | 483 |
| Potato-X61187 | LKDTFMMGADYYQTESEIASLLAEGKVPIGIGENTKIRKCIIDKNAKIGK | 429 |
| Watermelon-JE0133 | LKDTIMMGADTYQTEPEIAGLLAEGKVPIGIGRNTKIRNCIIDKNAKIGK | 485 |
| Muskmelon-AF030383 | LKDTIMMGADNYQTESEITGLLAEGKVPVGIGPNTKIRKCIIDKNAKIGK | 484 |
| Citrus_sinensis-ACF77017 | LKDTVMLGADYYQTESEIASLLAEGKVPIGVGRNTKIRNCIIDKNVKIGK | 486 |
| Pea-X96766 | LQDTVMMGADYYQTESEIASLLAEGKVPIGIGRNTKIKNCIIDKNAKIGK | 469 |
| Fragaria_x_ananassa-AAS00542 | LKDSIMMGADSYQTESEIAALLARGKVPIGIGRNTKIRLCIVDLNAKIGK | 474 |
| Sweet_Potato-AFL55398 | LEDTMVMGADYYQTESEIASLLATGKVPIGIGTNTKIRNCIIDKNARIGK | 477 |
| Tomato-AAC49942 | FKDTMMMGADYYQTESEIASLLAEGKVPIGVGPNTKIQKCIIDKNAKIGK | 477 |
| Potato-P55242 | FKDTMMMGADYYQTECEIASLLAEGKVPIGVGPNTKIQNCIIDKNAKIGK | 478 |
| Beet-P55233 | FQDTMMMGADYYQTESEIASLLAEGKVPVGVGQNTKIKNCIIDKNAKIGK | 481 |
| Chickpea-AF356003 | LQDTMMMGADYYQTESEIASLLAEGKVPVGVGENTKIRNCIIDKNARIGR | 480 |
| Watermelon-JE0132 | LKDTMMMGADYYQTESEIASLLAEGKIPIGIGENTKIRNCIIDKNARIGR | 440 |
| Muskmelon-AF030384 | LKDTMMMGAYYYQTESEIASLLAEGKIPIGIGENTKIRNCIIDKNAKIGR | 477 |

FIG. 1 (continued)

```
Maize_SH2-M81603             NVVITNSKGIQEADHPEEGYYIRSGIVVILKNAT---INDGSVI 516
Sorghum-T03445               NVVITNSKGIQEADHPEEGYYIKSGIVVILKNAT---IKDGSVI 517
Rice-T04156                  NVIIANTQGVQESDHPEEGYYIRSGIVVILKNAT---IKDGTVI 518
Rice-AAK27727                NVIIANTQGVQESDHPEEGYYIRSGIVVILKNAT---IKHGPII 518
Rice-U66041                  NAIIANTQGVQESDHPEEG-YIRSGIVVILKNATNATIKHGTVI 514
Maize_Agp1-Z38111            NVSITNKEGVQEADRPDEGYYIRSGIVVVLKNAT---IKDGTVI 518
Rice-D50317                  NVVITNSEGVQESDRPEEGYYIRSGIVVILKNAT---IKDGKVI 519
Barley-X67151                DVVISNKEGVQEADRPEEGYYIRSGIVVIQKNAT---IKDGTVV 523
Wheat-P12299                 DVVISNKEGVQEADRPEEGYYIRSGIVVIQKNAT---IKDGTVV 522
Maize_Agpl1zm                KVVISNSEGVDEADRTSEGFYIRSGITVVLKNAI---IADGLVI 505
Barley-U66876                NVTIANTEGVQESDRTSEGFHIRSGITVVLKNSV---IADGLVI 503
Sweet_Potato-AFL55399        NVVIANSEGIQEADRTSEGFYIRSGVTVILKNST---IPDGLVI 525
Tomato-T07674                NVVIANSEGVQEADRSSEGFYIRSGITVILKNST---IPDGTVI 516
Potato-X76136                NVVIANSEGVQEADRSSEGFYMASGITVISKNST---IPDGTVI 483
Sweet_Potato-AFL55396        DVVITNKDGVQESDRPDEGFYIRSGITIIMEKAT---IRDGTVI 517
Sweet_Potato-AFL55397        DVIIANKDGVEEADRPEEGFYIRSGIPVIMEKAV---IKDGTVI 515
Tomato-T07682                NVSIINKDGVQEADRPEEGFYIRSGIIIIAEKAT---IRDGTVI 524
Potato-X61187                NVSIINKDGVQEADRPEEGFYIRSGIIIILEKAT---IRDGTVI 470
Watermelon-JE0133            DVVIMNKEGVQEADRPEQGFYIRSGITIILEKAT---IEDGTVI 526
Muskmelon-AF030383           DVIIMNKDGVQEADRPEQGFYIRSGITIVMEKAT---IEDGTVI 525
Citrus_sinensis-ACF77017     DVVIVNKDGVQEADRPELGFYIRSGITIIMEKAT---IEDGMVI 527
Pea-X96766                   EVVIANKEGVQEADRSEDGFYIRSGITIIMEKAT---IEDGTVI 510
Fragaria_x_ananassa-AAS00542 DVIIMNKDGIQEADRPEEGFYIREESLSLWRRE----------- 507
Sweet_Potato-AFL55398        DVVIANKDGVDEADRADEGFYIRSGITIVLKNAT---IRDGTVI 518
Tomato-AAC49942              DVVILNKQGVEEADRSAEGFYIRSGITVIMKNAT---IKDGTVI 518
Potato-P55242                DVVILNKEGVEEADRSAEGFYIRSGITVIMKNAT---IKDGTVI 519
Beet-P55233                  DVVIANTDGVEEADRPNEGFYIRSGITIILKNAT---IQDGLVI 522
Chickpea-AF356003            NVIITNADGVEEADRTKEGFYIRSGITAILKNAT---IKDGTVI 521
Watermelon-JE0132            NVVIANSDDVQEADRPEDGFYIRSGITVTLKNAT---IKDGTII 481
Muskmelon-AF030384           NVVIANTDDVQEADRPEEGFYIRSGITVTLKNAT---IKDGTII 518
```

FIG. 1 (continued)

METHODS FOR INCREASING GRAIN YIELD

REFERENCE TO RELATED APPLICATIONS

This application claims the benefit of U.S. Provisional Application No. 62/000,173 filed May 19, 2014, which is incorporated herein by reference in its entirety.

STATEMENT OF GOVERNMENT SUPPORT

This invention was made with Government support under USDA/NIFA 2010-04228 awarded by the U.S. Department of Agriculture. The Government has certain rights in the invention.

INCORPORATION OF THE SEQUENCE LISTING

The sequence listing that is contained in the file named "UFFL048US_ST25.txt", which is 151 kilobytes (as measured in Microsoft Windows®) and was created on May 8, 2015, is filed herewith by electronic submission and is incorporated by reference herein.

FIELD OF THE INVENTION

The invention provides compositions and methods for increasing grain yield in cereal crops. More specifically, the invention is related to temperature-stable mutants of maize endosperm ADP-glucose pyrophosphorylase (AGPase), and methods for use thereof for increasing grain yield.

BACKGROUND OF THE INVENTION

ADP-glucose pyrophosphorylase (AGPase) is a highly regulated enzyme in the starch biosynthesis pathway. In planta the enzyme has a complex structure, an $\alpha 2\beta 2$ heterotetramer, that when expressed in the endosperm of seeds is heat labile. The heat lability of AGPase is often linked to grain loss during hot weather, and therefore increasing the thermo-stability of this enzyme is of great agronomical importance. Previously, heat stabile variants of this enzyme have been transformed into maize, potato, wheat, and rice and yield increases in seed number or weight were obtained. Conventional directed evolution methods for enhancing protein thermo-stabilities rely on collections of random mutations spread across the entire linear sequence of amino acids. In principle, such a strategy offers the chance to explore the complete sequence space of a given protein and thereby provide the globally optimal solution. In practice, however, the number of sequence variants at the DNA level ($64^{517}$ for the maize endosperm large subunit) means that the required library sizes vastly outstrip the ability of molecular biology to provide them and practical screening methods to evaluate them. This necessarily means that sequence space exploration will be only partial.

SUMMARY OF THE INVENTION

In one aspect, the present invention provides a polynucleotide comprising a sequence encoding a variant plant AGPase large subunit polypeptide, said polypeptide comprising a mutation at a position homologous or corresponding to amino acid 96, 161, or 443 of SEQ ID NO: 20 relative to a wild type plant AGPase large subunit polypeptide. In some embodiments, the variant plant AGPase large subunit polypeptide comprises a conserved motif having SEQ ID NO: 21, SEQ ID NO: 22, or SEQ ID NO: 23. In other embodiments, the variant plant AGPase large subunit polypeptide comprises at least 70% identity to SEQ ID NO:70. In further embodiments, the variant plant AGPase large subunit polypeptide comprises mutations in at least two positions homologous to amino acid 96, 161, or 443 of SEQ ID NO: 20 relative to a wild type plant AGPase large subunit polypeptide, or in each position homologous to amino acid 96, 161, and 443 of SEQ ID NO: 20 relative to a wild type plant AGPase large subunit polypeptide.

In some embodiments, the variant plant AGPase large subunit polypeptide of the invention comprises at least one mutation selected from the group consisting of a glycine or a glutamine at said position 161, an arginine or a glycine at said position 96, and an arginine at said position 443. The variant plant AGPase large subunit polypeptide of the invention may be operably linked to a heterologous promoter functional in plants. In yet other embodiments, the variant plant AGPase large subunit polypeptide comprising said mutation relative to a wild type plant AGPase large subunit polypeptide shown in FIG. 1.

In another aspect, the present invention provides a recombinant construct comprising a polynucleotide comprising a sequence encoding a variant plant AGPase large subunit polypeptide, said polypeptide comprising a mutation at a position homologous to amino acid 96, 161, or 443 of SEQ ID NO: 20 relative to a wild type plant AGPase large subunit polypeptide. In some embodiments, the invention provides a polypeptide encoded by said polynucleotide. In other embodiments, the invention provides a plant, seed, cell, or plant part comprising said polynucleotide. In further embodiments, the plant, seed, cell, or plant part comprising said polynucleotide is a monocotyledonous or dicotyledonous plant, seed, cell, or plant part. In yet further embodiments, the plant, seed, cell, or plant part is from a plant selected from the group consisting of rice, wheat, barley, oats, rye, sorghum, maize, sugarcane, pineapple, onion, bananas, coconut, lilies, millet, tomato, potato, sweet potato, pea, strawberry, beet, chickpea, watermelon, muskmelon, cassava, taro, sunflower, flax, and beans.

In another aspect, the invention provides a method of increasing the resistance or tolerance of a plant to heat stress conditions or increasing starch biosynthesis of a plant comprising expressing in the plant a polynucleotide comprising a sequence encoding a variant plant AGPase large subunit polypeptide, said polypeptide comprising a mutation at a position homologous to amino acid 96, 161, or 443 of SEQ ID NO: 20 relative to a wild type plant AGPase large subunit polypeptide. In some embodiments, the plant is a monocotyledonous or a dicotyledonous plant. In further embodiments, the plant is a plant selected from the group consisting of rice, wheat, barley, oats, rye, sorghum, maize, sugarcane, pineapple, onion, bananas, coconut, lilies, millet, tomato, potato, sweet potato, pea, strawberry, beet, chickpea, watermelon, muskmelon, cassava, taro, sunflower, flax, and beans. In other embodiments, the invention provides a method comprising transforming a plant with a polynucleotide comprising a sequence encoding a variant plant AGPase large subunit polypeptide, said polypeptide comprising a mutation at a position homologous to amino acid 96, 161, or 443 of SEQ ID NO: 20 relative to a wild type plant AGPase large subunit polypeptide, and regenerating a plant therefrom. In a further embodiment, the method comprises crossing a parent plant comprising said polynucleotide with itself or a second plant to obtain the plant in which resistance of a plant to heat stress conditions or starch biosynthesis is increased.

BRIEF DESCRIPTION OF THE DRAWINGS

FIG. 1: Shows an alignment of plant AGPase large subunit sequences. The alignment includes AGPase sequences from *Zea mays*, Genbank Accession No. M81603 (SEQ ID NO: 40); *Zea mays*, Genbank Accession No. Z38111 (SEQ ID NO: 41); *Zea mays*, Genbank Accession No. NP_001106017 (SEQ ID NO: 42); *Hordeum vulgare*, Genbank Accession No. X67151 (SEQ ID NO: 43); *Hordeum vulgare*, Genbank Accession No. U66876 (SEQ ID NO: 44); *Sorghum bicolor*, Genbank Accession No. T03445 (SEQ ID NO: 45); *Oryza sativa*, Genbank Accession No. T04156 (SEQ ID NO: 46); *Oryza sativa*, Genbank Accession No. AAK27727 (SEQ ID NO: 47); *Oryza sativa*, Genbank Accession No. U66041 (SEQ ID NO: 48); *Oryza sativa*, Genbank Accession No. D50317 (SEQ ID NO: 49); *Triticum aestivum*, Genbank Accession No. P12299 (SEQ ID NO: 50); *Lycopersicon esculentum*, Genbank Accession No. T07674 (SEQ ID NO: 51); *Lycopersicon esculentum*, Genbank Accession No. T07682 (SEQ ID NO: 52); *Lycopersicon esculentum*, Genbank Accession No. AAC49942 (SEQ ID NO: 53); *Solanum tuberosum*, Genbank Accession No. X76136 (SEQ ID NO: 54); *Solanum tuberosum*, Genbank Accession No. X61187 (SEQ ID NO: 55); *Solanum tuberosum*, Genbank Accession No. P55242 (SEQ ID NO: 56); *Ipomoea batatas*, Genbank Accession No. AFL55396 (SEQ ID NO: 57); *Ipomoea batatas*, Genbank Accession No. AFL55397 (SEQ ID NO: 58); *Ipomoea batatas*, Genbank Accession No. AFL55398 (SEQ ID NO: 59); *Ipomoea batatas*, Genbank Accession No. AFL55399 (SEQ ID NO: 60); *Citrus sinensis*, Genbank Accession No. ACF77017 (SEQ ID NO: 61); *Pisum sativum*, Genbank Accession No. X96766 (SEQ ID NO: 62); *Fragaria×ananassa*, Genbank Accession No. AAS00542 (SEQ ID NO: 63); *Beta vulgaris*, Genbank Accession No. P55233 (SEQ ID NO: 64); *Cicer arietinum*, Genbank Accession No. AF356003 (SEQ ID NO: 65); *Citrullus lanatus*, Genbank Accession No. JE0132 (SEQ ID NO: 66); *Citrullus lanatus*, Genbank Accession No. JE0133 (SEQ ID NO: 67); *Cucumis melo*, Genbank Accession No. AF030383 (SEQ ID NO: 68); *Cucumis melo*, Genbank Accession No. AF030384 (SEQ ID NO: 69). Conserved motifs surrounding mutated amino acids are underlined (SEQ ID NOs: 21-23), and amino acid positions mutated according to the present invention are highlighted.

DETAILED DESCRIPTION

The present invention describes novel ADP-glucose pyrophosphorylase (AGPase) polypeptides. AGPase enzymes may also be referred to as glucose-1-phosphate adenylyltransferase enzymes. As used herein, "AGPase" refers to an enzyme that catalyzes the conversion of a glucose-1-phosphate molecule and an ATP molecule to produce an ADP-glucose molecule and a diphosphate molecule. In many organisms, functional AGPase enzymes exist as multimers of multiple AGPase subunits. As used herein, "AGPase subunit" refers to a polypeptide that interacts with at least one additional polypeptide to form a functional AGPase enzyme. In many microorganisms, AGPase enzymes exist as a homotetramer of four identical AGPase subunits. In many higher plants, AGPase enzymes exist as a heterotetramer containing two large subunits and two small subunits. As used herein, "AGPase large subunit" refers to a polypeptide that can interact with other AGPase subunits to form a functional AGPase enzyme and that has a higher molecular weight than one or more of the other subunits that interact to form the AGPase enzyme. In a preferred embodiment, the modified AGPase large subunit of the invention possesses at least 70% identity to SEQ ID NO: 70. In other embodiments, the modified AGPase large subunit of the invention possesses at least 75, 80, 85, 90, 91, 92, 93, 94, 95, 96, 97, 98, or 99% identity to SEQ ID NO: 70.

Maize endosperm AGPase is highly regulated and temperature sensitive. Thermo-sensitivity of this enzyme is linked to grain loss in a variety of cereal crops. The present invention surprisingly provides variants of AGPase that increase the thermal stability of this heat labile enzyme. Nine amino acid positions in the AGPase large subunit were targeted for mutagenesis based on their conformational mobility. These mutagenic positions were selected using crystal structure atomic displacement parameters (B-factors) obtained from the potato small subunit homotetramer crystal structure. After each round of mutagenesis, iodine staining and antibody capture activity assays at varying temperatures were used to select the best position and amino acid change. Following 3 iterations, the initial detection method of iodine staining was saturated and a heat stable AGPase mutant was obtained. Kinetic studies on the heat stable mutant showed that it also exhibited an increased affinity for the activator, 3-PGA. Both temperature stability and allosteric regulation are of great importance in increasing grain yield.

The present invention therefore provides methods for improving the thermal stability of AGPase based on identification of conformationally mobile residues. Conformationally mobile residues are possible sites for initiating global protein unfolding. Since unfolding is highly cooperative, eliminating these motions can make a protein less susceptible to denaturation. Surprisingly, the present invention shows that mutagenesis of residues chosen based on a B-factor analysis of a different subunit from a protein made by a different organism resulted in improved properties of temperature stability in maize AGPase.

The present invention further provides methods which take advantage of the observation that thermo-stabilizing mutations are additive, allowing variations at individual codons to be examined sequentially, rather than simultaneously. Once improved variants at each position have been identified using the methods of the present invention, they can be combined to yield mutants with even better thermal stabilities. The invention further provides AGPase mutants in which not all of the mutations contribute directly to enhanced thermo-stability, but the combination of several mutations providing modest improvements leads to a significant overall change. The effect of several mutations of the present invention on thermal stability of the mutant enzyme may also be additive or synergistic.

The present invention therefore provides novel heat stable variants of AGPase, including variants with from one to three changes to the coding sequence. The heat stable variants of the present invention, including D161G, surprisingly link heat stability with allosteric regulation. This phenomenon was also observed for a T142F variant that exhibits increased heat stability and a decreased $K_a$ for 3-PGA such that activity was found in the absence of 3-PGA.

The invention therefore permits increases in crop performance, particularly under high heat growing conditions. In view of increasing concerns regarding rising global temperatures due to climate change, this represents a significant advance to agriculture and the art in general.

I. Nucleic Acids and Proteins

As used herein, the term "nucleic acid" or "polynucleotide" refers to a single or double-stranded polymer of deoxyribonucleotide bases or ribonucleotide bases read from the 5' to the 3' end. A nucleic acid or polynucleotide may also optionally contain non-naturally occurring or altered nucleotide bases that permit correct read through by a polymerase and do not reduce expression of a polypeptide encoded by that nucleic acid. The terms "nucleotide sequence" or "nucleic acid sequence" refer to both the sense and antisense strands of a nucleic acid as either individual single strands or in the duplex. The term "ribonucleic acid" (RNA) is inclusive of RNAi (inhibitory RNA), dsRNA (double stranded RNA), siRNA (small interfering RNA), mRNA (messenger RNA), miRNA (micro-RNA), tRNA (transfer RNA, whether charged or discharged with a corresponding acylated amino acid), and cRNA (complementary RNA). The words "nucleic acid fragment," "nucleotide sequence fragment", or more generally "fragment" will be understood by those in the art as a functional term that includes genomic sequences, ribosomal RNA sequences, transfer RNA sequences, messenger RNA sequences, operon sequences, and smaller engineered nucleotide sequences that express or may be adapted to express, proteins, polypeptides or peptides. The nomenclature used herein is that required by Title 37 of the United States Code of Federal Regulations §1.822 and set forth in the tables in WIPO Standard ST.25 (1998), Appendix 2, Tables 1 and 3.

As used herein, the terms "nucleic acid" and "polynucleotide" refer to a deoxyribonucleotide, ribonucleotide, or a mixed deoxyribonucleotide and ribonucleotide polymer in either single- or double-stranded form, and unless otherwise limited, would encompass known analogs of natural nucleotides that can function in a similar manner as naturally-occurring nucleotides. The polynucleotide sequences include the DNA strand sequence that is transcribed into RNA and the strand sequence that is complementary to the DNA strand that is transcribed. The polynucleotide sequences also include both full-length sequences as well as shorter sequences derived from the full-length sequences. Allelic variations of the exemplified sequences also fall within the scope of the subject invention. The polynucleotide sequence includes both the sense and antisense strands either as individual strands or in the duplex.

As used herein, the term "recombinant nucleic acid," "recombinant polynucleotide" or "recombinant DNA molecule" refers to a polynucleotide that has been altered from its native state, such as by linkage to one or more other polynucleotide sequences to which the recombinant polynucleotide molecule is not normally linked to in nature. Such molecules may or may not be present, for example, in a host genome or chromosome.

The present invention further provides polynucleotides that are complementary in sequence to the polynucleotides disclosed herein. Polynucleotides and polypeptides of the invention can be provided in purified or isolated form.

The subject invention also concerns oligonucleotide probes and primers, such as polymerase chain reaction (PCR) primers, that can hybridize to a coding or non-coding sequence of a polynucleotide of the present invention. Oligonucleotide probes of the invention can be used in methods for detecting and quantitating nucleic acid sequences encoding a mutant AGPase large subunit polypeptide of the invention. Oligonucleotide primers of the invention can be used in PCR methods and other methods involving nucleic acid amplification. In a preferred embodiment, a probe or primer of the invention can hybridize to a polynucleotide of the invention under stringent conditions. Probes and primers of the invention can optionally comprise a detectable label or reporter molecule, such as fluorescent molecules, enzymes, radioactive moiety (e.g., $^{3}$H, $^{35}$S $^{125}$I, etc.), and the like. Probes and primers of the invention can be of any suitable length for the method or assay in which they are being employed. Typically, probes and primers of the invention will be 10 to 500 or more nucleotides in length. Probes and primers that are 10 to 20, 21 to 30, 31 to 40, 41 to 50, 51 to 60, 61 to 70, 71 to 80, 81 to 90, 91 to 100 or more nucleotides in length are contemplated within the scope of the invention. Probes and primers of the invention can have complete (100%) nucleotide sequence identity with the polynucleotide sequence, or the sequence identity can be less than 100%. For example, sequence identity between a probe or primer and a sequence can be 99%, 98%, 97%, 96%, 95%, 90%, 85%, 80%, 75%, 70% or any other percentage sequence identity allowing the probe or primer to hybridize under stringent conditions to a nucleotide sequence of a polynucleotide of the invention. In one embodiment, a probe or primer of the invention has 70% or greater, 75% or greater, 80% or greater, 85% or greater, 90% or greater, or 95% to 100% sequence identity with a nucleotide sequence provided herein, including the complement thereof.

Because of the degeneracy of the genetic code, a variety of different polynucleotide sequences can encode polypeptides or mutant polypeptides disclosed herein. A table showing all possible triplet codons (and where U also replaces T) and the amino acid encoded by each codon is described in Lewin (1985). In addition, it is well within the capability of one of skill in the art to create alternative polynucleotide sequences encoding the same, or essentially the same, mutant polypeptides of the subject invention. These variant or alternative polynucleotide sequences are within the scope of the subject invention. As used herein, references to "essentially the same" sequence refers to sequences which encode amino acid substitutions, deletions, additions, or insertions which do not materially alter the functional activity of the polypeptide encoded by the polynucleotides of the present invention. Allelic variants of the nucleotide sequences encoding a wild type or mutant polypeptide of the invention are also encompassed within the scope of the invention.

Amino acids can be generally categorized in the following classes: non-polar, uncharged polar, basic, and acidic. Conservative substitutions whereby a mutant AGPase small or large subunit polypeptide of the present invention and/or a wild type or mutant AGPase small or large subunit polypeptide having an amino acid of one class is replaced with another amino acid of the same class fall within the scope of the subject invention so long as the polypeptide having the substitution still retains substantially the same functional activity (e.g., enzymatic and/or increased heat stability of an AGPase enzyme) as the polypeptide that does not have the substitution. Functional activity may be determined according to the methods of Giroux et al 1996 *Proc Natl Acad Sci USA* 93: 5824-5829 or as set forth in the Experimental section below. Polynucleotides encoding a mutant AGPase small subunit polypeptide and/or a wild type or mutant AGPase large subunit polypeptide having one or more amino acid substitutions in the sequence are contemplated within the scope of the present invention.

Table 1 provides a listing of examples of amino acids belonging to each class.

TABLE 1

Classes of Amino Acid

| | |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

Substitution of amino acids other than those specifically exemplified or naturally present in a wild type or mutant polypeptide and/or AGPase enzyme of the invention are also contemplated within the scope of the present invention. For example, non-natural amino acids can be substituted for the amino acids of a mutant AGPase small or large subunit polypeptide, so long as the mutant polypeptide having the substituted amino acids retains substantially the same functional activity as the mutant polypeptide in which amino acids have not been substituted. Examples of non-natural amino acids include, but are not limited to, ornithine, citrulline, hydroxyproline, homoserine, phenylglycine, taurine, iodotyrosine, 2,4-diaminobutyric acid, a-amino isobutyric acid, 4-aminobutyric acid, 2-amino butyric acid, γ-amino butyric acid, e-amino hexanoic acid, 6-amino hexanoic acid, 2-amino isobutyric acid, 3-amino propionic acid, norleucine, norvaline, sarcosine, homocitrulline, cysteic acid, t-butylglycine, t-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form. Allelic variants of a protein sequence of a wild type or mutant AGPase small or large subunit polypeptide of the present invention are also encompassed within the scope of the invention.

II. Methods of Modifying Nucleic Acids and Proteins

The subject invention also concerns variants of the polynucleotides of the present invention that encode functional wild type or mutant AGPase small or large subunit polypeptides of the invention. Variant sequences include those sequences wherein one or more nucleotides of the sequence have been substituted, deleted, and/or inserted. The nucleotides that can be substituted for natural nucleotides of DNA have a base moiety that can include, but is not limited to, inosine, 5-fluorouracil, 5-bromouracil, hypoxanthine, 1-methylguanine, 5-methylcytosine, and tritylated bases. The sugar moiety of the nucleotide in a sequence can also be modified and includes, but is not limited to, arabinose, xylulose, and hexose. In addition, the adenine, cytosine, guanine, thymine, and uracil bases of the nucleotides can be modified with acetyl, methyl, and/or thio groups. Sequences containing nucleotide substitutions, deletions, and/or insertions can be prepared and tested using standard techniques known in the art.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., Burlington, Mass.). Polynucleotides and polypeptides contemplated within the scope of the subject invention can also be defined in terms of identity and/or similarity ranges with those sequences of the invention specifically exemplified herein. In certain embodiments, the invention provides polypeptide sequences having at least about 70, 80, 85, 90, 95, 99, or 99.5 percent identity to a polypeptide sequence provided herein. In certain embodiments, the invention provides polynucleotide sequences having at least about 70, 80, 85, 90, 95, 99, or 99.5 percent identity to a polynucleotide sequence provided herein, including SEQ ID NO: 19.

In certain embodiments, the invention provides polynucleotides encoding polypeptides comprising the amino acid sequence provided herein, or a fragment or variant thereof. In certain embodiments, the polynucleotides encode polypeptides comprising a variant of the amino acid sequence provided herein wherein the amino acid homologous or corresponding to position 161 has been mutated, wherein the amino acid at position 96 has been mutated, wherein the amino acid at position 443 has been mutated, or combinations, fragments, or variants thereof. As used herein, an amino acid homologous or corresponding to position 96, 161, or 443 is an amino acid that is aligned with positions 96, 161, or 443 of SEQ ID NO: 20 when using the methods to align polypeptides that are described herein. For example, see FIG. 1. In certain embodiments, the polynucleotides of the invention encode one or more polypeptides comprising a variant wherein the amino acids at positions 161 and 96 have been mutated, wherein the amino acids at positions 96 and 443 have been mutated, or wherein the amino acids at positions 161 and 443 have been mutated, or combinations, fragments, or variants thereof. In certain embodiments, the polynucleotides introduced into the plant encode one or more polypeptides comprising a variant wherein the amino acids at positions 161, 96, and 443 have been mutated, or fragments or variants thereof. The invention further provides polynucleotides encoding polypeptides comprising a variant of the amino acid sequences provided herein wherein the amino acid corresponding to position 161 has been mutated to be a G or Q, wherein the amino acid at position 96 has been mutated to be a G or R, or wherein the amino acid at position 443 has been mutated to be an R, or combinations thereof.

In certain embodiments, the invention provides polynucleotides encoding a polypeptide comprising a fragment or variant of the amino acid sequence provided herein and comprising a conserved motif, for example, such as SEQ ID NO: 21. In other embodiments, polynucleotides of the invention encode a fragment or variant of the amino acid sequences provided herein and comprising a conserved motif having SEQ ID NO: 21, wherein position 3 of SEQ ID NO: 21 is an uncharged polar amino acid. In yet other embodiments, the polynucleotides of the invention encode a fragment or variant comprising a conserved motif having SEQ ID NO: 21, wherein position 3 of SEQ ID NO: 21 is G or Q. In certain embodiments, the invention provides polynucleotides encoding a polypeptide comprising a fragment or variant comprising a conserved motif having SEQ ID NO: 22. In other embodiments, polynucleotides of the invention encode a fragment or variant comprising a conserved motif having SEQ ID NO: 22, wherein position 8 of the motif is an uncharged polar amino acid or a basic amino acid. In yet other embodiments, the polynucleotides of the invention encode a fragment or variant comprising a conserved motif having SEQ ID NO: 22, wherein position 8 of the motif is a G or R.

In yet other embodiments, the invention provides polynucleotides encoding a polypeptide comprising conserved motif having SEQ ID NO: 23. In other embodiments, in the conserved motif having SEQ ID NO: 23, position 7 of the motif is a basic amino acid. In further embodiments, position 7 is an R.

Fragments and variants of a mutant polypeptide of the present invention can be generated as described herein and tested for the presence of enzymatic and heat stable function using standard techniques known in the art. Thus, an ordinarily skilled artisan can readily prepare and test fragments and variants of a mutant polypeptide of the invention and determine whether the fragment or variant retains functional activity relative to full-length or a non-variant mutant polypeptide. Fragments and variants of mutant polypeptides can be tested for AGPase activity, for example using methods disclosed herein or by other methods well-known in the art.

The subject invention also concerns isolated mutant AGPase small or large subunit polypeptides. In one embodiment, the mutant AGPase small or large subunit polypeptide is an AGPase small or large subunit polypeptide of Zea mays. In a specific embodiment, an AGPase large subunit polypeptide of the invention has an amino acid sequence as shown in the sequence listing or drawings, or functional fragment or variant thereof. An AGPase small or large subunit polypeptide or enzyme of the invention can be purified using standard techniques known in the art. In one embodiment, a polynucleotide of the invention encoding an AGPase small or large subunit polypeptide is incorporated into a microorganism, such as E. coli, and the AGPase small or large subunit polypeptide expressed in the microorganism and then isolated therefrom.

In certain embodiments, polypeptides of the invention, and functional peptide fragments thereof, can be used to generate antibodies that bind specifically to a polypeptide of the invention, and such antibodies are contemplated within the scope of the invention. The antibodies of the invention can be polyclonal or monoclonal and can be produced and isolated using standard methods known in the art.

Polypeptide fragments according to the invention typically comprise a contiguous span of at least about 25 and about 515 amino acids of a sequence disclosed herein, including SEQ ID NO: 70. In certain embodiments, polypeptide fragments comprise 25, 50, 95, 150, or 500 amino acids of a sequence provided herein.

Fragments of a mutant AGPase small or large subunit polypeptide of the invention or an AGPase large subunit polypeptide, as described herein, can be obtained by cleaving the polypeptides of the invention with a proteolytic enzyme (such as trypsin, chymotrypsin, or collagenase) or with a chemical reagent, such as cyanogen bromide (CNBr). Alternatively, polypeptide fragments can be generated in a highly acidic environment, for example at pH 2.5. Polypeptide fragments can also be prepared by chemical synthesis or using host cells transformed with an expression vector comprising a polynucleotide encoding a fragment of an AGPase large subunit polypeptide or a fragment of a mutant AGPase small subunit polypeptide of the invention, for example, a mutant polypeptide that is a fragment of an amino acid sequence provided herein. Fragments of a mutant large or small subunit AGPase polypeptide of the invention also contemplated herein include fragments of the polypeptide wherein all or a part of a transit or signal sequence of the polypeptide is removed.

III. Expression Constructs

Polynucleotides useful in the present invention can be provided in an expression construct. Expression constructs of the invention generally include regulatory elements that are functional in the intended host cell in which the expression construct is to be expressed. Thus, a person of ordinary skill in the art can select regulatory elements for use in bacterial host cells, yeast host cells, plant host cells, insect host cells, mammalian host cells, and human host cells. Regulatory elements include promoters, transcription termination sequences, translation termination sequences, enhancers, and polyadenylation elements. As used herein, the term "expression construct" refers to a combination of nucleic acid sequences that provides for transcription of an operably linked nucleic acid sequence. As used herein, the term "operably linked" refers to a juxtaposition of the components described wherein the components are in a relationship that permits them to function in their intended manner. In general, operably linked components are in contiguous relation.

An expression construct of the invention can comprise a promoter sequence operably linked to a polynucleotide sequence encoding a mutant polypeptide of the invention. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site in the expression construct as it is from the transcription start site in its natural genetic environment. Some variation in this distance is permitted without substantial decrease in promoter activity. A transcription start site is typically included in the expression construct.

If the expression construct is to be provided in or introduced into a plant cell, then plant viral promoters, such as, for example, a cauliflower mosaic virus (CaMV) 35S (including the enhanced CaMV 35S promoter (see, for example U.S. Pat. No. 5,106,739)) or a CaMV 19S promoter or a cassava vein mosaic can be used. Other promoters that can be used for expression constructs in plants include, for example, zein promoters including maize zein promoters, prolifera promoter, Ap3 promoter, heat shock promoters, T-DNA 1'- or 2'-promoter of A. tumefaciens, polygalacturonase promoter, chalcone synthase A (CHS-A) promoter from petunia, tobacco PR-1a promoter, ubiquitin promoter, actin promoter, alcA gene promoter, pin2 promoter (Xu et al., 1993), maize WipI promoter, maize trpA gene promoter (U.S. Pat. No. 5,625,136), maize CDPK gene promoter, and RUBISCO SSU promoter (U.S. Pat. No. 5,034,322) can also be used. Tissue-specific promoters, for example fruit-specific promoters, such as the E8 promoter of tomato (accession number: AF515784; Good et al. (1994)) can be used. Fruit-specific promoters such as flower organ-specific promoters can be used with an expression construct of the present invention for expressing a polynucleotide of the invention in the flower organ of a plant. Examples of flower organ-specific promoters include any of the promoter sequences described in U.S. Pat. Nos. 6,462,185; 5,639,948; and 5,589,610. Seed-specific promoters such as the promoter from a β-phaseolin gene (for example, of kidney bean) or a glycinin gene (for example, of soybean), and others, can also be used. Endosperm-specific promoters include, but are not limited to, MEG1 (EPO application No. EP1528104) and those described by Wu et al. (1998), Furtado et al. (2001), and Hwang et al. (2002). Root-specific promoters, such as any of the promoter sequences described in U.S. Pat. No. 6,455,760 or U.S. Pat. No. 6,696,623, or in published U.S. patent application Nos. 2004/0078841; 2004/0067506; 2004/0019934; 2003/0177536; 2003/0084486; or 2004/0123349, can be used with an expression construct of the invention. Constitutive promoters (such as the CaMV, ubiquitin, actin, or NOS promoter), developmentally-regulated promoters, and inducible promoters (such as those promoters than can be induced by heat, light, hormones, or chemicals) are also contemplated for use with polynucleotide expression constructs of the invention.

Expression constructs of the invention may optionally contain a transcription termination sequence, a translation termination sequence, a sequence encoding a signal peptide, and/or enhancer elements. Transcription termination regions can typically be obtained from the 3' untranslated region of a eukaryotic or viral gene sequence. Transcription termination sequences can be positioned downstream of a coding sequence to provide for efficient termination. A signal peptide sequence is a short amino acid sequence typically present at the amino terminus of a protein that is responsible for the relocation of an operably linked mature polypeptide to a wide range of post-translational cellular destinations, ranging from a specific organelle compartment to sites of protein action and the extracellular environment. Targeting gene products to an intended cellular and/or extracellular destination through the use of an operably linked signal peptide sequence is contemplated for use with the polypeptides of the invention. Classical enhancers are cis-acting elements that increase gene transcription and can also be included in the expression construct. Classical enhancer elements are known in the art, and include, but are not limited to, the CaMV 35S enhancer element, cytomegalovirus (CMV) early promoter enhancer element, and the SV40 enhancer element. Intron-mediated enhancer elements that enhance gene expression are also known in the art. These elements must be present within the transcribed region and are orientation dependent. Examples include the maize shrunken-1 enhancer element (Clancy and Hannah, 2002).

DNA sequences which direct polyadenylation of mRNA transcribed from the expression construct can also be included in the expression construct, and include, but are not limited to, an octopine synthase or nopaline synthase signal. The expression constructs of the invention can also include a polynucleotide sequence that directs transposition of other genes, i.e., a transposon.

IV. AGPase Subunit Expression in Plant Cells

The subject invention also concerns cells transformed with a polynucleotide of the present invention encoding a mutant AGPase small or large subunit polypeptide of the invention. In one embodiment, the cell is transformed with a polynucleotide sequence comprising a sequence encoding the amino acid sequences provided herein, or a functional fragment or variant thereof, or a fragment or variant thereof having AGPase activity. In a specific embodiment, the cell is transformed with a polynucleotide sequence encoding a variant provided herein. In one embodiment, the polynucleotide sequence is provided in an expression construct of the invention. The transformed cell can be a prokaryotic cell, for example, a bacterial cell such as *E. coli* or *B. subtilis*, or the transformed cell can be a eukaryotic cell, for example, a plant cell, and a yeast cell. Plant cells include, but are not limited to, dicotyledonous and monocotyledonous cells. Plant cells may be cells from rice, wheat, barley, oats, rye, sorghum, maize, sugarcane, pineapple, onion, bananas, coconut, lilies, millet, tomato, potato, sweet potato, pea, strawberry, beet, chickpea, watermelon, muskmelon, cassava, taro, sunflower, flax, and beans. In one embodiment, the plant cell is a cell from a *Zea mays* plant.

Techniques for transforming plant cells with a gene are known in the art and include, for example, *Agrobacterium* infection, biolistic methods, electroporation, calcium chloride treatment, PEG-mediated transformation, etc. Transformed cells can be selected, redifferentiated, and grown into plants that contain and express a polynucleotide of the invention using standard methods known in the art. The seeds and other plant tissue and progeny of any transformed or transgenic plant cells or plants of the invention are also included within the scope of the present invention.

The subject invention also concerns methods for expressing the polynucleotides of the invention in plant cells. These methods may include methods that alter the native polynucleotides present in the genome of the plant cells of interest. Methods to alter the polynucleotides of a genome of interest are known in the art and include meganucleases designed against the plant genomic sequence of interest (D'Halluin et al 2013 *Plant Biotechnol J* 11: 933-941); CRISPR-Cas9, TALENs, and other technologies for precise editing of genomes (Feng, et al. *Cell Research* 23:1229-1232, 2013, Podevin, et al. 2013 *Trends Biotechnology* 31: 375-383, Wei et al., 2013 *J Gen Genomics* 40: 281-289, Zhang et al 2013, WO 2013/026740); Cre-lox site-specific recombination (Dale et al. (1995) *Plant J* 7:649-659; Lyznik, et al. (2007) *Transgenic Plant J* 1:1-9; FLP-FRT recombination (Li et al. (2009) *Plant Physiol* 151:1087-1095); Bxb1-mediated integration (Yau et al. *Plant J* (2011) 701: 147-166); zinc-finger mediated integration (Wright et al. (2005) *Plant J* 44:693-705); Cai et al. (2009) *Plant Mol Biol* 69:699-709); and homologous recombination (Lieberman-Lazarovich and Levy (2011) *Methods Mol Biol* 701: 51-65); Puchta, H. (2002) *Plant Mol Biol* 48:173-182). These and other similar techniques may be used to precisely edit the genome of a plant cell to produce a modified polynucleotide encoding an AGPase subunit polypeptide that contains a mutation of the present invention. Alternatively, random genomic mutations may be induced through the application of appropriate treatments including ethyl methanesulfonate (EMS) treatment (Qu et al 2014 Methods Mol Biol 1062: 225-239) to plant cells, sodium azide or methylnitrosourea (MNU) treatment (Sikora et al 2011 *Int J Plant Genomics* 2011 doi:10.1155/2011/314829) to plant cells, or exposure of plant cells to gamma rays or to fast neutron irradiation (Kodym and Afza 2003 *Methods Mol Biol* 236: 189-204) followed by the use of molecular methods to identify plant cells containing the appropriate mutations such that a variant AGPase subunit of the present invention is encoded by the genome of the plant cell.

The subject invention also concerns methods for producing a plant that exhibits increased heat stability relative to a wild type plant, wherein a polynucleotide encoding a mutant AGPase small or large subunit polypeptide of the present invention is introduced into a plant cell and the polypeptide(s) encoded by the polynucleotide(s) is expressed. In one embodiment, the plant cell comprises non-mutant genes encoding a wild type AGPase small or large subunit polypeptide. In another embodiment, the plant cell comprises at least one polynucleotide encoding a mutant AGPase large subunit polypeptide. In a further embodiment, a polynucleotide encoding a mutant AGPase large subunit polypeptide is also introduced into a plant cell along with the polynucleotide encoding the mutant AGPase small subunit polypeptide. In one embodiment, the polynucleotide or polynucleotides is incorporated into the genome of the plant cell and a plant is grown from the plant cell. In a preferred embodiment, the plant grown from the plant cell stably expresses the incorporated polynucleotide or polynucleotides. In another embodiment, the polynucleotide or polynucleotides are expressed from self-replicating vectors derived from plant viruses. These vectors contain the sequences necessary for the vector to replicate within a plant cell as well as the sequences necessary to provide expression of the polynucleotides of interest. Vectors derived from plant viruses have been described, for example in Jung et al 2014 *Biotechnol Prog* 30: 905-915; Pflieger et al 2014 *BMC Plant Biol* 14: 232; Gu et al 2014 *Plant Biotechnol J* 12: 638-649; Huang et al 2010 *Plant Biotechnol J* 8: 783-795; Gleba et al 2014 *Curr Top Microbiol Immunol* 375: 155-192; and Lindbo 2007 *Plant Physiol* 145: 1232-1240. Self-replicating vectors derived from plant viruses may contain polynucleotides designed to upregulate or to downregulate an endogenous plant gene in the plant of interest, or may be used to express a novel heterologous gene. Expression from these vectors may be confined to the cells that were initially infected, or may be systemic throughout the infected plant. In a preferred embodiment, a polynucleotide encoding the variant AGPase subunit of the invention may be expressed from a virally-derived vector.

The subject invention also concerns methods for increasing starch synthesis in a plant or plant tissue (such as a plant seed or endosperm tissue). In one embodiment, a method of the invention comprises introducing one or more polynucleotides of the present invention into a plant. In certain embodiments, the polynucleotides introduced into the plant encode one or more polypeptides comprising the amino acid sequences provided herein, or a fragment or variant thereof. In certain embodiments, the polynucleotides introduced into the plant encode one or more polypeptides comprising the amino acid sequence of SEQ ID NO: 20 wherein the amino acid at position 161 has been mutated, wherein the amino acid at position 96 has been mutated, wherein the amino acid at position 443 has been mutated, or combinations, fragments, or variants thereof. In certain embodiments, the amino acids at positions 161 and 96 have been mutated, the amino acids at positions 96 and 443 have been mutated, or the amino acids at positions 161 and 443 have been mutated, or the amino acids at positions 161, 96, and 443 have been mutated, or fragments or variants thereof. In some embodiments, the amino acid at position 161 has been mutated to be a G or Q, the amino acid at position 96 has been mutated to be a G or R, or the amino acid at position 443 has been mutated to be an R, including all possible combinations thereof.

In certain embodiments, the polynucleotides introduced into the plant encode one or more polypeptides comprising a fragment or variant comprising a conserved motif having SEQ ID NO: 21. In other embodiments, position 3 of SEQ ID NO: 21 is an uncharged polar amino acid. In yet other embodiments, position 3 is G or Q.

In certain embodiments, the polynucleotides introduced into the plant encode one or more polypeptides provided herein and comprising a conserved motif having SEQ ID NO: 22. In other embodiments, position 8 of the motif is an uncharged polar amino acid or a basic amino acid. In yet other embodiments, position 8 of the motif is a G or R.

In yet other embodiments, the polynucleotides introduced into the plant encode one or more polypeptides comprising a conserved motif having SEQ ID NO: 23. In other embodiments, position 7 of the motif is a basic amino acid. In further embodiments, position 7 of the motif is an R.

In one embodiment, the polynucleotide is stably incorporated into the genome of the plant or plant tissue. The polynucleotide can comprise regulatory elements, such as a promoter and/or enhancer sequences, that provide for increased expression of the polynucleotide and/or the polypeptide encoded thereby. In a specific embodiment, the promoter sequence is one that provides for constitutive or tissue-specific (e.g., endosperm) expression. Plants or plant tissues containing the polynucleotide, or progeny of the plants, optionally can be screened for increased expression of a polynucleotide or polypeptide of the invention. In one embodiment, multiple copies of one or more polynucleotides of the invention are introduced into a plant or plant tissue and stably incorporated into the genome of the plant. In one embodiment, a polynucleotide of the invention is provided in an expression construct as described herein.

The invention further provides plants comprising the polynucleotides, polypeptides, and expression constructs disclosed herein. Plants of the present invention may be monocots or dicots, and may include, for example, rice, wheat, barley, oats, rye, sorghum, maize, sugarcane, pineapple, onion, bananas, coconut, lily, turf grasses, and millet plants.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE 1

V. Plasmid Preparation

The small and large subunit plasmids of maize endosperm AGPase (pMONcBt2 and pMONcSh2, respectively) (Giroux et al., 1996) were expressed in *E. coli* AC70R1-504 cells (Iglesias et al., 1993) as previously described (Boehlein et al., 2008).

B-Factor Analysis of the Potato Small Subunit Homotetramer x-Ray Crystal Structure The coordinate file for 1YP2 was manually edited to create four separate files, one for each of the four monomer chains. Each was analyzed individually by the B-FITTER program, which ranked the residues in decreasing order of average B-factor (calculated as a mean value for each residue). To avoid artifacts caused by crystal packing forces, a residue was considered to have an abnormally high B-factor only if the value was ≥55 in each of the four monomers. These criteria yielded nine residues in the structure of 1YB2. The corresponding amino acids in both the small and large subunit of maize endosperm AGPase were determined by using the previously-published alignment and the residues are shown in Table 3.

The ISM (Iterative Saturation Mutagenesis) mutants were prepared by QuikChange site-directed mutagenesis (Agilent) using pMONcSh2 as template in the first iteration. pMONcSh2Q96G, pMONcSh2Q96R, pMONcSh2Q96G; D161G, pMONcSh2Q96R;D161G, pMONcSh2Q96G; D161G:A443R, and pMONcSh2Q96R;D161G:A443R were used as templates in subsequent mutagenesis reactions.

VI. Library Screening

AC70R1-504 transformants were grown overnight in 96-deepwell plates, then 3 µL aliquots of each culture were plated on square Petri dishes containing 2% (w/v) glucose (48 clones/plate, which includes one wild-type (Bt2/Sh2) and MP-TI/Sh2 control per plate). One plate was incubated at 37°, the other at 42° C. for 7.5 hr. Plates were cooled to room temperature before being placed into a glass chamber containing iodine crystals. After staining, plates were immediately photographed on a light table (to ensure even illumination) and the color intensity of each colony (integrated over its entire surface) was evaluated using the ImageJ program. Staining was calculated as a percentage relative to the wild type control on that particular plate and positives were defined as colonies with more intense color than wild-type.

After the initial screening and selection of the first mutant, subsequent iterations used the selected mutant as template in individual QuikChange site-directed mutagenesis reactions. The resulting DNAs from mutagenesis at each site were pooled, used to transform AC70R1-504 cells already containing the pMONcBt2 plasmid and grown on LB+2% glucose+50 µg/ml Kan+75 µg/ml Spec plates at 42° C. overnight. Darkest staining colonies on each plate were selected. The selections were respotted on two identical LB+Kan+Spec plates. One of these plates was incubated at 37° C. and the other at 42° C. overnight. The resulting colony spots were exposed to iodine vapors. DNA was prepared for the darkest staining 42° C. grown selections and sequencing was performed.

VII. Plate Capture Assay

Following the first iteration, dark staining colonies were screened for heat stability using a plate capture assay. This assay utilized a monoclonal antibody specific for the large subunit of AGPase that pulled down both AGPase subunits and retained activity. Thus, large samples of clarified lysates could be analyzed for AGPase activity in this manner. Initial heat stability was assessed by growing each mutant enzyme at 37° C. in 25 ml cultures to an OD of 0.7-1.0 and induced for 2-4 hours at room temperature. Cultures were then pelleted and stored at −80° C. Pellets were resuspended in 1 ml of glycerol buffer (0.1M HEPES pH 7.4, 5 mM $MgCl_2$, 10 mM $KH_2PO_4^-$, 5 mM EDTA, 5% glycerol) and disrupted by sonication. Cell debris was removed by centrifugation at 14000 rpm for 10 minutes. Protein was adjusted to 2.5 mg/ml (Biorad protein reagent) and stored at −80° C. until use. Preparations made in this way were stable for several days.

A high binding 96 well plate (96 well EIA/RIA plate, Costar) was prepared for the plate capture assay by coating the appropriate number of wells with 200 µl of Antibody Ab 12.1 (diluted 1:1000 in 1× phosphate buffered saline, PBS). The plate was incubated at 4° C. with shaking overnight then washed three times with PBST (1×PBS with 0.05% Tween20) and once with 1×PBS. Clarified lysates (200 µl of 5 mg/ml) were loaded on the Ab coated plate and incubated for 1 hour at 4° C. with shaking. After 1 hour the plate was washed 4× with cold glycerol buffer and placed on ice. Assay mix (250 µl) was added to each well of the plate and incubated at 55° C. for 0, 10 and 60 min. Reactions were terminated by removing 200 µl of assay mix from plate at the appropriate time and placed in cuvettes. Development mix (300 µl) was added to the cuvettes and then measured A340. Activity was determined by calculating the activity between 10 and 60 min. Initial rates (0-10 min) were discarded, as the reaction mixes needed time to reach 55° C. Reaction rates between 10-60 min were shown to be linear with time.

VIII. Determination of Apparent Kinetic Constants, $K_m$, $K_{cat}$ and $K_a$ An endpoint assay was used to determine the rate of the AGPase reaction by coupling the formation of PPi to a decrease in NADH concentration (Boehlein et al., 2008). Reaction mixtures (300 µl) contained the following components when saturating: 50 mM HEPES pH 7.4, 15 mM $MgCl_2$, 2.0 mM ATP, and 2.0 mM G-1-P and 5 mM 3-PGA. The Michaelis constants ($K_m$) were obtained by varying one substrate in the presence of saturating concentrations of the second substrate. The activation constants were obtained by varying the activator at fixed levels of both substrates. All reactions were performed at 37° C. and mixes were pre-warmed before starting the reaction with enzyme. Reactions were terminated by boiling the reaction mixes for 2 minutes followed by development with 200 µl of coupling reagent (25 mM imidazole pH 7.4, 4 mM $MgCl_2$, 1 mM EDTA, 0.2 mM NADH, 0.725 U aldolase, 0.4 U triose phosphate isomerase, 0.6 U glycerophosphate dehydrogenase, 1 mM fructose 6-phosphate and 0.8 µg purified PPi-PFK per reaction). The absorbance at 340 nm was monitored after 30 min and the amount of PPi produced was determined from a standard curve using PPi in complete reaction mixtures lacking AGPase. Blank samples contained complete reaction mixtures without enzyme and the change in absorbance between the blank and the reaction was used to calculate the amount of PPi produced. Reactions were linear with time and enzyme concentration.

IX. Activity at 55° C.

Activity measurements at increased temperature were performed by looking at the rate of the reaction over a period of 10 minutes. Each time course contained an assay mix (saturating substrates and activator) of 1300 µl and was started with the addition of enzyme. At appropriate times, 300 µl of the reaction was removed and boiled for 2 minutes followed by development (see above). A rate at 55° C. was calculated for those enzymes that were linear with time from 2.5-10 minutes.

X. Thermodynamic Stability of Purified Maize AGPase and ISM Mutants

Thermodynamic stability of the purified AGPase and ISM mutants was assessed by pre-treating 10 µl of the enzyme preparation (36 ng of enzyme with 0.5 mg/ml BSA) at 37° C. for 0-7.5 min and then returning them to ice. The activity of the enzyme was then determined at 37° C., in the presence of saturating concentrations of substrates and activator, as described above. The percentage of activity remaining was calculated by dividing the activity of the treated sample from the untreated sample. The ½ time of inactivation ($T_{1/2}$) was calculated from plots of logarithmic plots of % activity versus time whereby the slope was equal to −k/(2.3). $T_{1/2}$ was calculated from the equation $k=0.693/t_{1/2}$.

XI. Determination of Kinetic Constants in the Absence of 3-PGA

In the absence of 3-PGA, the ATP and G-1-P $K_m$'s were determined by varying ATP from 0.25-7.5 mM at fixed concentrations of G-1-P, (5.0-30 mM). Reactions were performed for 10 min and terminated by boiling. Blank mixtures contained everything except ATP.

XII. Pi Inhibition of GGR

TABLE 2

PPi inhibition as carried out in the presence or absence of 3-PGA.

| Varying substrate | Activator (3-PGA) 5 mM | 3-PGA Concentration when varied | Pi concentration when varied | Pi Concentration when held constant |
|---|---|---|---|---|
| ATP | − | [a]0.1-3 | 10-30 | 0.4 |
| G-1-P | − | 5-30 | 5-50 | 0.2 |
| ATP | + | 0.025-1.5 | 0.5-25 | 0.25 |
| G-1-P | + | 0.025-1.5 | 1-25 | 5 |

[a]all units are in mM

XIII. Data Analysis

The apparent Michaelis constant and maximum velocity of each reaction was calculated from a V vs. S plots using nonlinear regression analysis and the following equation, $v = V_{max}S/(K_m+S)$, where v is the measured velocity, $V_{max}$ is the maximum velocity, S is the substrate concentration. The activation constant ($K_a$) was obtained using the following equation: $V = V_{min} + V_{max}*(X)/(K_a+X)$, where $V_{min}$ is the velocity in the absence of activator and $V_{max}$ is the change in activity from $V_{min}$ to the total velocity. X is the activator concentration, $K_a$ is the activation constant. All linear regression was carried out using the software program Prism (Graph Pad, San Diego Calif.).

Kinetic data for the determination of the $K_m$ value in the absence of 3-PGA for D161G and GGR and were fitted to equations using the nonlinear equations using GraphPad Prism 4.0c. Initial velocity data were fit to Eq. (1), which describes a sequential mechanism where v is the measured reaction velocity, V is the maximal velocity, A and B are the concentrations of substrates (ATP and G-1-P), $K_a$, and $K_b$ are the corresponding Michaelis-Menten constants, and $K_{ia}$ is the dissociation constant for substrate A. The concentration of ATP was varied from 0.25-7.5 for ATP and 5.0-30 mM for G-1-P.

$$v = VAB/(K_{ia}K_{mb}+K_{mb}A+K_{ma}B+AB) \quad (1)$$

XIV. Pi Inhibition Data

Phosphate inhibition data were fitted to equations 1 and 2, which correspond to noncompetitive inhibition (NC; Eq. 2) or linear mixed type inhibition (L-MT; Eq. 3) using GraphPad Prism software. v is the measured velocity, $V_m$ is the maximum velocity, S is the substrate concentration, $K_i$ is the inhibition constant, $K_s$ is the dissociation constant for the ES complex, I is the inhibitor concentration, cc is the factor by which $K_i$ changes when the inhibitor is present.

$$v = V_m(S/K_s)/(1+S/K_s+I/K_i+SI/K_iK_s) \quad NC \quad (2)$$

$$v = V_m(S/K_s)/(1+S/K_s+I/K_i+SI/\alpha K_iK_s) \quad L\text{-}MT \quad (3)$$

EXAMPLE 2

B-Factor Analysis

Crystallographic B-factors indicate uncertainties in atomic positions, which often correlate with conformational disorder. Since no three-dimensional structure of a heterotetrameric plant AGPase is currently available, the potato small subunit homotetramer crystal structure (Jin et al., 2005) was used in the methods of the present invention. One monomer of this homotetramer is illustrated in Boehlein et al 2015 *Arch Biochem Biophys* 568: 28-37 with the relative B-factors indicated both by chain width (wider=higher B-factor) and color (red=highest B-factor). B-FITTER (Reetz et al., 2007) was used to rank each residue on the basis of their average B-factor in each of the four homotetramer chains. To identify those residues most likely to affect protein structure, those residues with B-factors ≥55 in each of the four monomers were selected. The positions of these residues in the potato homotetramer crystal structure are shown with their counterparts in the maize large subunits in Table 3.

TABLE 3

Maize endosperm AGPase residues suspected to have unusually high relative B-factors by analogy with the potato small subunit homotetramer x-ray crystal structure (Jin et al. 2005) and results of site-saturation mutagenesis libraries at these positions.

| Potato ss residue | Residue mean B-factor[a] | Maize ls equivalent | $Q_{codon}$ value; Predicted number of amino acids | Number of positives at 37° C./42° C. |
|---|---|---|---|---|
| Arg 33 | 62.36 | Gln 96 | 0.85; 18-19 | 9/4 |
| Glu 99 | 74.38 | Asp 161 | 0.80; 17-18 | 2/9 |
| Asp 218 | 71.25 | Ile 285 | 0.80; 17-18 | 2/0 |
| Lys 222 | 68.41 | Gln 289 | 0.81; 17-18 | 1/3 |
| Arg 307 | 65.10 | Pro 372 | 0.83; 18-19 | 2/12 |
| Asp 375 | 74.12 | Glu 440 | 0.87; 19-20 | 10/2 |
| Arg 378 | 67.55 | Ala 443 | 0.85; 18-19 | 2/2 |
| Lys 379 | 67.03 | Ser 444 | 0.87; 19-20 | 9/8 |
| Leu 380 | 66.24 | Lys 445 | 0.84; 18-19 | 9/4 |

[a]The average mean B-factor for all residues in the potato small subunit homotetramer was 34.1.

All nine of the conformationally disordered residues in the potato small subunit occurred on surface loops. Given the high degree of sequence conservation between the potato and maize AGPase sequences, it is likely that the overall structures are highly similar. Conformationally mobile residues in the potato structure were therefore evaluated in the maize counterpart as being possibly disordered.

EXAMPLE 3

Site-Saturation Library Construction and Evaluation

Nine random replacement libraries were constructed for the maize large subunit residues identified by B-factor analysis. A polymerase chain reaction (PCR)-based methodology was used (Sullivan et al., 2013) to provide high-quality libraries with little contamination by the parent sequence and undetectable levels of concatameric primer inserts which would otherwise dilute the library and add to the screening burden. An offset primer design strategy made the PCR amplifications exponential, which enhanced transformation yield. This contrasts with conventional primer design methods using primers that overlap completely and result in linear, rather than exponential, amplifications that yield correspondingly smaller quantities of DNA for *Escherichia coli* (*E. coli*) transformation. Primer mixtures encompassed an NNK mixture of bases at the targeted codon, wherein N is an equal representation of A, C, G and T, K is an equal representation of G and T and M is an equal representation of A and C. This 32-member mixture encodes all 20 canonical amino acids as well as one stop codon, ensuring that all amino acid replacements were interrogated at the targeted positions of the AGPase large subunit. Primer sequences are shown in Table 4.

AC70R1-504 cells had previously been transformed with a second plasmid that encoded the wild-type maize endosperm AGPase small subunit, allowing expression of heterotetramers. A number of assay parameters were optimized in pre-

TABLE 4

Primers used in site-directed mutagenesis in the first iteration.

| Mutation | Direction | SEQ ID | Primer sequence |
|---|---|---|---|
| Q96X | For | 1 | GCA CTG GAT CTN NKC TCT TTC CTC TGA CAA GCA CAA GAG C |
| Q96X | Rev | 2 | AGA GGA AAG AGM NNA GAT CCA GTG CCT CCG CCC AAA ATG A |
| D161X | For | 3 | TCA ACT TTG CTN NKG GAT CTG TAC AGG TAT TAG CGG CTA C |
| D161X | Rev | 4 | TGT ACA GAT CCM NNA GCA AAG TTG ATC CCG CCT TCA AGG T |
| I285X | For | 5 | TGA GCT ATG CTN NKG ATG ATG CAC AGA AAT ATC CAT ACC T |
| I285X | Rev | 6 | TGT GCA TCA TCM NNA GCA TAG CTC AGG AAG TTG GTC TCA A |
| Q289X | For | 7 | TAG ATG ATG CAN NKA AAT ATC CAT ACC TTG CAT CAA TGG G |
| Q289X | Rev | 8 | TAT GGA TAT TTM NNT GCA TCA TCT ATA GCA TAG CTC AGG A |
| P372X | For | 9 | ATT TTT ACG ATN NKA AAA CAC CTT TCT TCA CTG CAC CCC G |
| P372X | Rev | 10 | AAA GGT GTT TTM NNA TCG TAA AAA TCA AAC TTG GAA GGC T |
| E440X | For | 11 | TCT ATG AAA CTN NKG AAG AAG CTT CAA AGC TAC TGT TAG C |
| E440X | Rev | 12 | GAA GCT TCT TCM NNA GTT TCA TAG ATG TCC GCT CCC ATC A |
| A443X | For | 13 | CTG AAG AAG AAN NKT CAA AGC TAC TGT TAG CTG GGA AGG T |
| A443X | Rev | 14 | AGT AGC TTT GAM NNT TCT TCT TCA GTT TCA TAG ATG TCC G |
| S444X | For | 15 | AAG AAG AAG CTN NKA AGC TAC TGT TAG CTG GGA AGG TCC C |
| S444X | Rev | 16 | AAC AGT AGC TTM NNA GCT TCT TCT TCA GTT TCA TAG ATG T |
| K445X | For | 17 | AAG AAG CTT CAN NKC TAC TGT TAG CTG GGA AGG TCC CAG T |
| K445X | Rev | 18 | GCT AAC AGT AGM NNT GAA GCT TCT TCT TCA GTT TCA TAG A |

N is an equal representation of A, C, G and T; K is an equal representation of G and T; M is an equal representation of A and C.

The nucleotide diversities at the targeted positions were evaluated for each library by sequencing the collection of pooled plasmid DNAs obtained after the initial PCR product had been used to transform an E. coli host. As expected, the fluorescence sequencing chromatograms showed unique DNA sequences at all positions except for those targeted for randomization. The relative peak heights for each base (which correspond to the relative nucleotide compositions of the mixed plasmid population) were calculated for each of the targeted bases at the appropriate locations on the chromatograms. These were used to calculate values for $Q_{codon}$ and used to estimate the number of amino acids likely to be present at each randomized position (Sullivan et al., 2013). A $Q_{codon}$ value of 1.0 represents perfect randomization while 0.0 indicates no sequence diversity. Libraries predicted to contain fewer than 17 of the 20 possible amino acids on the basis of low $Q_{codon}$ values were rejected and re-constructed until suitably diverse populations were obtained.

Once site-saturation libraries had been constructed and validated for all nine targeted positions, the plasmid mixtures were used to transform E. coli AC70R1-504 cells (a glgC⁻ mutant unable to accumulate glycogen due to loss of the host AGPase) so that the thermal stabilities of the AGPase variants could be assessed on the basis of glycogen accumulation at elevated growth temperatures. The liminary studies by methods known in the art including growth times, glucose concentrations present in the growth medium, growth temperature, etc.

We evaluated 92 randomly-chosen clones from each library in order to have a 95% chance of covering all variants present. Transformants were grown in the presence of glucose and the accumulated glycogen was revealed by incubating plates in the presence of iodine vapor. Two examples each of wild-type AGPase and a known thermostable variant (MP-TI) were included as controls. Since the darkness of iodine staining correlates with the amount of accumulated glycogen, digital photographs of plates were analyzed quantitatively by the ImageJ program (Image Processing and Analysis in Java; National Institute of Mental Health, Bethesda, Md., USA) to provide relative color density for each colony. These were used to calculate a relative color density for each library colony after dividing by the intensity of the positive control on the same plate. These assays were carried out at both 37° C. and 42° C. to provide thermal stabilities under challenging or extremely challenging temperatures. The numbers of clones showing significantly greater staining than the wild-type controls are collected in Table 3. These positives were examined by DNA sequencing and several variants were studied in detail following large-scale expression and purification. Following this first round of mutagenesis, Q96G, S444R, D161G, D161Q, E440A and E440R were purified and their ability to catalyze the reaction at 55° C. analyzed. This was to be sure that the dark staining at 42° C. correlated with activity of the purified enzyme at increased temperatures. As seen in Table 5, only changes at the 161 position conferred increased activity at 55° C. The change to glutamine offered some stability, while the change to glycine significantly increased the ability of the enzyme to operate at a much higher temperature (Table 5).

TABLE 5

Activity at 37° C. and 55° C. of purified first iteration mutants.

| Enzyme | Activity 37° C.* | Activity 55° C.* | % Activity 55° C./37° C. |
|---|---|---|---|
| Wt | 15.2 | 0 | — |
| Q96G | 6.7 | 1.35 | 20.2 |
| D161G | 13.1 | 7.8 | 60 |
| D161Q | 10.6 | 1.0 | 9.4 |
| E440A | 9.3 | 0.1 | 1.1 |
| A443R | 7.9 | 0 | 0 |
| S444R | 27.8 | 0.4 | 1.4 |

*Activity is presented in µmol/min/mg

The templates used for the next iteration of saturation mutagenesis were the double mutants Q96G;D161G (GG) and Q96R;D161G (RG). The Q96 mutants were chosen because they had the darkest colony staining. The D161G change was selected because of its increased 55° C. activity.

For the second iteration of saturation mutagenesis, QuikChange mutagenesis (Agilent) was performed at the remaining seven sites. Primer sequences are shown in Table 6. Three of the RG new mutant sites (I285, Q289, and P372) were transformed into AC70R1-504 cells containing the wile-type small subunit (Bt2). Colonies staining darker than the RG colonies were selected at the P372, I285 and Q289 locations. The DNA from seven dark staining RG;I285NNK colonies and nine RG;Q289NNK colonies was sequenced to determine the highest probability of change, but results were scattered, thus no particular amino acid change was dominant at these positions. In addition, no dark staining colonies were seen at position P372. Next, E440, A443, S444 and K445 sites were individually mutated, the DNA of each mutagenesis reaction was extracted, and combined for transformation into Bt2 competent cells. The darkest staining colonies were then re-plated and the DNA was sequenced from the twenty darkest staining colonies on these plates. The sequencing results showed that out of 20 colonies, several changes occurred one time, (A443V, S444Q, S444R, S444G), one change occurred four times (S444E) and one change appeared 12 times (A443R). The selection technique demonstrated that while discretion in picking darker stained colonies by eye was not perfect, the approach worked considerably well if multiple colonies were screened. Thus, the mutant Q96R;D161G;A443R (RGR) was selected for the next iteration.

TABLE 6

Primers used in site-directed mutagenesis after the first iteration.

| Mutation | Direction | SEQ ID | Primer sequence |
|---|---|---|---|
| D161G | For | 24 | GCGGGATCAACTTTGCTGGTGGGTCTGTACAGGTATTAGCGG |
| D161G | Rev | 25 | CCGCTAATACCTGTACAGACCCACCAGCAAAGTTGATCCCGC |
| I285X | For | 26 | GAGACCAACTTCCTGTCCTATGCTNNKGATGATGCACAGAAATATCC |
| I285X | Rev | 27 | GGATATTTCTGTGCATCATCMNNAGCATAGGACAGGAAGTTGGTCTC |
| Q289X | For | 28 | GCTATGCTATAGATGATGCTNNKAAATATCCATACCTTGCATC |
| Q289X | Rev | 29 | GATGCAAGGTATGGATATTTMNNAGCATCATCTATAGCATAGC |
| P372X | For | 30 | CCTTCCAAGTTTGATTTTTACGACNNKAAAACACCTTTCTTCACTGCACCC |
| P372X | Rev | 31 | GGGTGCAGTGAAGAAAGGTGTTTTMNNGTCGTAAAAATCAAACTTGGAAGG |
| E440X | For | 32 | GGAGCGGACATCTATGAAACTNNKGAAGAGGCTTCAAAGCTACTGTTAGC |
| E440X | Rev | 33 | GCTAACAGTAGCTTTGAAGCCTCTTCMNNAGTTTCATAGATGTCCGCTCC |
| A443X | For | 34 | CGGACATCTATGAAACTGAAGAAGAANNKTCAAAGCTACTGTTAGCTGG |
| A443X | Rev | 35 | CCAGCTAACAGTAGCTTTGAMNNTTCTTCTTCAGTTTCATAGATGTCCG |
| S444X | For | 36 | CATCTATGAAACTGAAGAAGAAGCGNNKAAGCTACTGTTAGCTGGGAAGG |
| S444X | Rev | 37 | CCTTCCCAGCTAACAGTAGCTTMNNCGCTTCTTCTTCAGTTTCATAGATG |
| K445X | For | 38 | CATCTATGAAACTGAAGAAGAAGCGTCANNKCTACTGTTAGCTGGGAAGGTC |
| K445X | Rev | 39 | GACCTTCCCAGCTAACAGTAGMNNTGACGCTTCTTCTTCAGTTTCATAGATG |

N is an equal representation of A, C, G and T; K is an equal representation of G and T; M is an equal representation of A and C.

A similar technique was used with GG as the template. QuikChange saturation mutagenesis was performed at each of the seven sites and the resulting mutant DNAs were combined. AC70R1-504 cells containing Bt2 were transformed with the combined mutant DNAs, grown overnight at 42° C. on glucose containing LB plates, and ensuing colonies were exposed to iodine vapors. Here, 36 dark staining colonies were selected and re-plated on an LB-glucose plate grown at 42° C. DNA was prepared from the six darkest staining streaks and sequenced. Mutations occurred at only 2 of the 7 positions, 2 of which resulted in S444E and the remaining was A443R. A443R was selected since this mutation was obtained ⅔ of the time. Thus, the two clones moving on to the next round of iterations were RGR and GGR.

The fourth iteration of saturation mutagenesis on both templates was performed using the same protocol. Following staining, six GGR;NNK colonies were selected based on their staining and the DNA sequenced. The results of the sequencing data indicated that the differences in staining were no longer visible, thus out of 6 colonies sequenced, 4 resulted in template, 1 had a change of Q289A and one had a change of I285V. Similarly when RGR was used as a template, 3 RGR;NNK clones were sequenced (1 template and 2 S444R). Since the staining technique was no longer able to discriminate between the template and the additional iteration, no additional iterations were performed.

The activity of each mutant, single to quadruple mutants, at 55° C. was then determined using an antibody capture plate assay. This assay was developed so that large numbers of samples could be rapidly purified and assayed. The antibody used has a unique property in that when AGPase is bound to it, it retains activity; however, the complex Ab:AGPase is more heat stable than the AGPase in solution. Plate assays revealed that while the wild-type (wt) enzyme had activity at 55° C. when bound to the antibody, it was not linear with time, and decreased significantly after the first 30 minutes of incubation. Both double mutants, GG and RG, had activity linear with time for 50 minutes. The plate assay was also used to evaluate the activity of the bound AGPase in the presence and absence of 3-PGA. Here it is shown that, both double mutants had appreciable activity in the absence of 3-PGA (Table 7), an unexpected result that links the heat stability and allosteric regulatory properties together.

TABLE 7

Plate assay of measured velocity (v) vs. time at 55° C. and activity in the presence and absence of 3-PGA.

| Mutant | 55° Activity (+3-PGA) | | | 37° Activity (+3-PGA) 30 min | 37° Activity (−3-PGA) 50 min |
| --- | --- | --- | --- | --- | --- |
| | 10-30 min | 30-50 min | 10-50 min | | |
| Wt | 88 | 44 | 132 | 71 | 4 |
| GG | 175 | 143 | 318 | 76 | 56 |
| GGR | 110 | 109 | 219 | 65 | 56 |
| GGRA | 111 | 151 | 262 | 86 | 52 |
| GGRV | 113 | 114 | 227 | 78 | 40 |
| RG | 107 | 139 | 246 | 74 | 95 |
| RGR | 114 | 141 | 255 | 96 | 115 |
| RGRR | 121 | 143 | 264 | 43 | 67 |
| MP | 97 | 132 | 229 | 76 | 75 |

GG = Q96G, D161G;
GGR = Q96G, D161G, A443R;
GGRA = Q96G, D161G, A443R, Q289A;
GGRV = Q96G, D161G, A443R, I285V;
RG = Q96R, D161G;
RGR = Q96R, D161G, A443R;
RGRR = Q96R, D161G, A443R, S444R

EXAMPLE 4

Kinetic Characterization of the Iterative Saturation Mutants

Each mutant, comprising 1, 2, 3 or 4 changes, was grown in a large scale culture, expressed and purified according to standard procedures (Boehlein et al., 2005). The $K_m$ for ATP and G-1-P, in the presence of the activator, 3-PGA, was determined by varying one substrate while the co-substrate was held constant and saturating. As shown in Table 8, in the presence of 3-PGA, the $K_m$ for both ATP and G-1-P for each of the mutants is similar to wt maize, with the largest variation in $K_m$ being approximately two-fold. Thus, the effects of these mutations on the kinetic constants are minimal. Next, the activation constant, $K_a$, was determined for each of the mutant enzymes. Here a decrease in the $K_a$ for each of the mutants of approximately 3-6 fold was observed. This property appears to stem from the D161G change, and includes all enzymes which carry this mutation (Table 8). To be certain the effect is the result of the D161G mutation, and not the result of other single mutant changes, Q96R and Q96G were purified and characterized. As shown in Table 8, the kinetic constants for Q96G and Q96R are more closely related to wt maize, exhibiting less than a 2-fold change in $K_a$ for 3-PGA. In addition, there was little fluctuation in the $K_m$ values for ATP and G-1-P. Thus it appears that the increased affinity for 3-PGA can be attributed to the D161G variant alone and the effect is retained when additional mutations are pyramided with D161G.

TABLE 8

Kinetic constants of ISM mutants.

| Enzyme | ATP $K_m$ | G-1-P $K_m$ | 3-PGA $K_a$ | $V_{max}$ | $V_{min}$ |
| --- | --- | --- | --- | --- | --- |
| D161G | 0.044 | 0.060 | 0.039 | 18.6 | 1.1 |
| RG | 0.063 | 0.038 | 0.034 | 17.8 | 3.2 |
| RGR | 0.062 | 0.028 | 0.039 | 13.7 | 2.0 |
| RGRR | 0.038 | 0.025 | 0.039 | 12.8 | 3.8 |
| GG | 0.031 | 0.021 | 0.040 | 13.3 | 0 |
| GGR | 0.057 | 0.038 | 0.056 | 31.4 | 4.1 |
| GGRA | 0.057 | 0.037 | 0.044 | 24.8 | 4.2 |
| GGRV | 0.046 | 0.024 | 0.062 | 19.1 | 1.7 |
| Q96R | 0.072 | 0.032 | 0.13 | 16.0 | 0 |
| Q96G | 0.055 | 0.064 | 0.19 | 19.5 | 0 |
| Wt | 0.069 | 0.039 | 0.22 | 22.6 | 0 |

TABLE 8-continued

Kinetic constants of ISM mutants.

| Enzyme | ATP $K_m$ | G-1-P $K_m$ | 3-PGA $K_a$ | $V_{max}$ | $V_{min}$ |
|--------|-----------|-------------|-------------|-----------|-----------|
| T142F  | 0.2       | 0.04        | 0.03        | 17.8      | 5.1       |
| SH2-E  | 0.10      | 0.03        | 0.07        | 16.6      | 4.2       |

RG = Q96R, D161G;
RGR = Q96R, D161G, A443R;
RGRR = Q96R, D161G, A443R, S444R;
GG = Q96G, D161G;
GGR = Q96G, D161G, A443R;
GGRA = Q96G, D161G, A443R, Q289A;
GGRV = Q96G, D161G, A443R, I285V

Next, the activity in the absence of 3-PGA was determined. Table 8 shows both the activity in the presence and absence of the activator. Each of the ISM mutants have a substantial amount of activity in the absence of 3-PGA, with the exception of GG (Table 8). This trait appears to also stem from the D161G mutation, since the Q96R and Q96G single mutants do not share this property. As several mutations are pyramided together, an additive effect of this 3-PGA independent activity is seen. Interestingly, the additional mutation of A443R to GG in the third iteration, resurrects the activity in the absence of 3-PGA and dramatically increases the $V_{max}$ in the presence of 3-PGA three-fold (13.3 µmol/min/mg (GG) to almost 31.4 µmol/min/mg (GGR) Table 8). This is the only ISM mutant which yielded an increase in the catalytic rate.

EXAMPLE 5

Kinetic and Thermodynamic Stability

While properties that include increased catalytic activity and activator-independent activities are of great agricultural importance, the main goal here was to create a variant that would remain active at increased temperatures. Two different methods were used to screen temperature effects on the purified ISM mutants. First, the kinetic stability of the enzyme at 55° C. was examined. This temperature rendered the wt maize enzyme completely inactive, while other previously constructed variants had substantial activity. Second, the thermodynamic stability of the enzymes was studied by pre-incubation of the naked enzymes (in the absence of substrates, activators and products) for various times at 37° C., followed by activity measurements at 37° C.

Table 9 displays the results of these 2 experiments. First, it is shown that D161G retains approximately 50% of its activity when assayed at 55° C. for 15 minutes (Table 9). While the D161G mutant has considerable activity at 55° C., its activity at 37° C. is slightly lower (84%) than the wild-type activity. Since all the other mutations stemmed from D161G, the activity in each subsequent mutation would be predicted to have this partial activity, unless the sites interact. This in fact was the case for each of the changes, except for the triple mutant, GGR. The addition of A443R to the GG mutant yielded an enzyme with considerably higher activity at 55° C. and surpassed the activity of the wt enzyme at 37° C. While some mutants render a higher percentage of activity, when comparing 55° C./37° C. the triple mutant has by far the highest activity in both circumstances.

TABLE 9

Velocity of ISM mutants at 37° C. and 55° C.

| Enzyme    | V 37° C. | V 55° C. | 55° C./37° C. | T1/2 |
|-----------|----------|----------|---------------|------|
| D161G     | 16.0     | 8.9      | 56            | 4.4  |
| RG        | 17.7     | 14.2     | 80            | 5.2  |
| RGR       | 11.2     | 6.6      | 58            | 5.0  |
| RGRR      | 9.2      | 8.5      | 92            | 6.8  |
| GG        | 12.1     | 8.0      | 66            | 7.2  |
| GGR       | 26.4     | 21.7     | 82            | 5.7  |
| GGRA      | 19.2     | 15.4     | 80            | 7.2  |
| GGRV      | 12.6     | 11.6     | 94            | 5.5  |
| Wt        | 19.2     | 0        | 0             | 6.0  |
| T142F     | 21.9     | 6.0      | 28            | 4.6  |
| SH2-E     | 22.4     | 24.3     | 111           | 3.5  |
| MP + SH2-E | 18.4    | 23.6     | 128           | 46   |

RG = Q96R, D161G;
RGR = Q96R, D161G, A443R;
RGRR = Q96R, D161G, A443R, S444R;
GG = Q96G, D161G;
GGR = Q96G, D161G, A443R;
GGRA = Q96G, D161G, A443R, Q289A;
GGRV = Q96G, D161G, A443R, I285V

TABLE 10

Kinetic constants in the absence of 3-PGA

| Enzyme       | ATP $K_m$ | G-1-P $K_m$ | $k_{cat}$ | $K_{ia}$ |
|--------------|-----------|-------------|-----------|----------|
| [a]Maize-wt  | [c]4.0    | 2.8         | 35.2      | ND       |
| D161G        | 0.043     | 6.8         | 48.8      | 1.4      |
| GGR          | 0.10      | 8.74        | 72.4      | 0.72     |
| [b]T142F     | 1.73      | 0.09        | 53.8      | 1.5      |
| [b]SH2-E     | 2.53      | 0.03        | 67.6      | 5.4      |

$V_{max}$ to $k_{cat}$ conversion, multiply $v_{max}$ (µmol) by 3.5
$K_m$ and $K_{ia}$ values are presented in mM; $k_{cat}$ values are presented in s$^{-1}$
[a]data from Boehlein et al., 2010
[b] data from Boehlein et al., 2013
[c] ATP $K_m$ could not be determined because G-1-P was not saturating. Since G-1-P saturation was not reached, value reported is the apparent $K_m$, in the presence of 15 mM G-1-P.

The thermodynamic stability was also determined for each of the mutants by incubating the enzymes for 1-15 minutes at 37° C., returning them to ice, and then assaying according to standard protocols. Control samples were maintained on ice, and the half-life of inactivation was determined from a plot of the log % activity vs. time. Interestingly, although all of the ISM mutants had a substantial activity at 55° C., none of the mutants had an increase in their half-life when compared to the wt maize enzyme (Table 9).

EXAMPLE 6

Selection of Mutants for Further Evaluation

Based on the kinetic results (Table 10) and catalytic properties at 55° C. (Table 10) both D161G and GGR were selected for a more detailed kinetic analysis. D161G was selected because this single mutation was the foundation for every other mutation, and had superior qualities, including a lower $K_a$ for 3-PGA, activity in the absence of 3-PGA and activity at 55° C. when compared to the maize wt enzyme. The GGR mutant was primarily chosen based on its increased catalytic rate at 37° C. and high performance at 55° C. Its high activity in the absence of 3-PGA was also paramount. The first kinetic parameters determined were the Michaelis constants, the catalytic rate ($k_{cat}$) and the dissociation constant ($K_{ia}$) for the E-ATP complex, in the absence of 3-PGA. Here, ATP was varied at several fixed concentrations of G-1-P, in the absence of the activator, 3-PGA. For the wt maize enzyme, this activator primarily responds by reducing the $K_m$ for both substrates, with little effect on the reaction rate (Boehlein et al., 2013). Here it is shown that the single mutation of D161G retains a high G-1-P $K_m$, and has a catalytic rate similar to the wt maize enzyme in the absence of the activator (Table 10). Interestingly, the $K_m$ for ATP is significantly decreased in this mutant when compared to wild-type (~100×) and is identical to its $K_m$ value in the presence of 3-PGA (0.04 mM). The kinetic mechanism established ATP as the first substrate to bind, thus the activator is no longer necessary for this first step. The GGR enzyme also retains a high $K_m$ for G-1-P in the absence of an activator, similar to the wt maize enzyme, but its catalytic rate is approximately double (Table 10). The ATP $K_m$ is once again comparable to its value in the activated form, alleviating the need for an activator to bind the first substrate. Thus, 3-PGA acts on both of these mutants by increasing the binding of G-1-P with little effect on the binding of ATP. This is in contrast to the single mutation of T142F (Boehlein et al., 2013), a recently constructed mutation created based on evolutionary constraints, where the ATP $K_m$ remains high, and the G-1-P $K_m$ is equal to its 3-PGA activated value. This variant also conditions both heat stability and high activity in the absence of an activator.

Next, the kinetics of the GGR mutant were further investigated by following Pi inhibition in the presence and absence of 3-PGA. Experiments were performed by keeping both substrates constant and non-saturating at several fixed concentrations of Pi. Inhibition of the wt maize AGPase by Pi is quite complex. In the absence of an activator, Pi was found to be a partial mixed type inhibitor with respect to both ATP and G-1-P (Table 11). Under the assay conditions, the calculated $K_m$ for both substrates are very high, greater than 20 mM, and the Ki for Pi is also high, in the 3-5 mM range. Interestingly, the inhibition is incomplete, thus even at high concentrations, Pi does not completely inhibit the wild-type enzyme. The partiality of inhibition obtained is calculated from a β factor <1 (Table 11). Additionally, Pi interacts with the substrates, in such a way that makes their binding better. This is reflected by an α value <1 when either substrate is varied, (Table 11).

TABLE 11

| | | | Pi inhibition in the absence of 3-PGA | | | | |
|---|---|---|---|---|---|---|---|
| Enzyme | Varied Substrate | [b]Pattern | $K_m$ | $K_i$ | α | β | $V_{max}$ |
| [a]Maize | ATP | P-MT | 20.4 +/− 10.1 | 3.4 +/− 1.1 | 0.063 +/− 0.034 | 0.52 +/− 0.17 | 6.7 +/− 2.2 |
| | G-1-P | P-MT | 22.2 +/− 9.0 | 5.1 +/− 2.1 | 0.095 +/− 0.065 | 0.92 +/− 0.31 | 4.2 +/− 1.1 |
| GGR | ATP | NC | 0.54 +/− 0.057 | 113.0 +/− 27 | | | 7.1 +/− 0.3 |
| | G-1-P | | | 13.1 +/− 0.96 | 52.7 +/− 2.9 | | 16.0 +/− 0.55 |
| SH2E | ATP | NC | 0.97 +/− 0.081 | 20.9 +/− 1.6 | | | 11.0 +/− 1.4 |
| | G-1-P | | 0.20 +/− 0.019 | 0.055 +/− 0.013 | 0.85 +/− 0.17 | 0.44 +/− 0.03 | 5.6 +/− 0.15 |

ATP, 0.5 mM; G-1-P, 5 mM
[a]data from Boehlein et al., 2010
[b]data from Boehlein et al., 2013

A similar examination of the Pi inhibition was then followed with GGR in the absence of 3-PGA. This investigation showed that inhibition was quite simple, with Pi exhibiting a non-competitive pattern with respect to each substrate, thus the substrate and Pi can be bound to the GGR mutant at any given time, and the ESI complex cannot go on to form product. Furthermore, the inhibition by phosphate is complete, and Pi does not affect the binding of either substrate. Under the conditions of this experiment, the Km for G-1-P is extremely high, similar to the wt AGPase, but the ATP Km is very low, approximately 40-fold lower than wt AGPase. While the inhibition by Pi is complete, the Ki value with respect to both substrates (50-100 mM) is extremely high, approximately 10-20 times higher than the normal concentration of Pi in the endosperm tissue of maize (~6.5 mM).

Inhibition by Pi was then followed in the presence of the activator 3-PGA. Here again, the wt AGPase displayed a partial mixed type inhibition pattern with $K_i$ values 0.5-1 mM (Table 12). The interaction factor, α, of >1 indicates that ATP binding in the presence of 3-PGA becomes more difficult as the concentration of Pi rises. The GGR mutant displayed a linear mixed type pattern with an interaction factor of 2.5 when varying ATP, thus in the presence of 3-PGA, Pi has a negative effect on ATP binding, and Pi inhibition is complete. A simple non-competitive inhibition pattern was seen when varying G-1-P. The $K_i$ for Pi was still much higher (10-20 mM) than the wt AGPase, thus this variant would be more recalcitrant to Pi inhibition in the endosperm. This is similar to what is seen for the evolutionary mutant SH2-E where simple inhibition patterns were also observed.

TABLE 12

Pi inhibition in the presence of 3-PGA

| Enzyme | Varied Substrate | [a]Pattern | [b]$K_m$ | $K_i$ | α | β | $V_{max}$ |
|---|---|---|---|---|---|---|---|
| Maize | ATP | P-MT | 0.11 +/− 0.0057 | 0.37 +/− 0.053 | 4.61 +/− 0.70 | 0.83 +/− 0.037 | 31.3 +/− 0.4 |
|  | G-1-P | P-MT | 0.091 +/− 0.0042 | 1.00 +/− 0.18 | 0.90 +/− 0.012 | 0.52 +/− 0.023 | 24.9 +/− 0.3 |
| GGR | ATP | L-MT | 0.11 +/− 0.005 | 10.7 +/− 1.7 | 2.5 +/− 0.66 |  | 21.9 +/− 3.6 |
|  | G-1-P | NC | 0.085 +/− 0.003 | 20.7 +/− 0.80 |  |  | 26.1 +/− 0.30 |
| SH2E | ATP | NC | 0.21 +/− 0.01 | 7.8 +/− 0.21 |  |  | 15.1 +/− 0.33 |
|  | G-1-P | NC | 0.063 +/− 0.003 | 6.62 +/− 0.39 |  |  | 10.0 +/− 1.6 |

ATP and G-1-P when held constant were 0.4 mM and 0.2 mM respectively
[a]data from Boehlein et al., 2010
[b]data from Boehlein et al., 2013

EXAMPLE 7

Transformation of Plant Cells and Field Studies pIPK27-MCSBAR expression vectors comprising maize 27 kd zein promoters operably linked to the coding regions of the variant Sh2-ISM sequences and NOS terminator sequences were constructed. Expression vectors also included an herbicide resistance gene as a selectable marker. Plasmids were amplified in *E. coli*, and transformed into *Agrobacterium tumefaciens* cells. Transformed *A. tumefaciens* cells were used to transform Hi II maize cells. A total of 12 independent events were generated that gave rise to female fertile plants. These plants were pollinated using B73 maize plants.

Progeny plants comprising the transgene were selected by painting a small strip of a leaf with herbicide one week following pollination. After 7 days, leaf strips were scored for resistance or sensitivity to the herbicide. Resulting mature ears were scored for total weight, seed number, and total seed weight. Temperatures on each day following pollination were recorded using an on-site weather station. Plants were evaluated for yield, including ear weight.

Approximately thirty-five plants derived from each line were evaluated for ear weight, with approximately 50% herbicide-sensitive and 50% herbicide-tolerant plants. The ear weight of herbicide-resistant plants was divided by the ear weight of herbicide-sensitive plants in order to determine the effect of transgene expression on yield, as herbicide-resistant plants are expected to contain the transgene. The average temperature over the four days following pollination is shown for each event. The ear weight ratios shown in Table 13 were determined.

TABLE 13

Ear Weight Ratios of herbicide-resistant plants divided by herbicide-sensitive plants

| Event | Ear Weight Ratio | Temp (° F.) |
|---|---|---|
| 7 | 1.24 | 96 |
| 10 | 1.03 | 96 |
| 25 | 1.01 | 96 |
| 11 | 1 | 96 |
| 6 | 0.91 | 96 |
| 16 | 0.91 | 96 |
| 45 | 0.66 | 96 |

EXAMPLE 8

Determination of Transgene Expression Levels

Events 7, 10, 25, and 11 were self-pollinated. The resulting seeds were planted in soil and grown in a greenhouse setting. The plants that grew from these seeds were cultivated and self-pollinated. Developing seeds were harvested 12 days after pollination and RNA was extracted from the developing embryos using Qiazol reagent and the 96 well RNA extraction kit from Qiagen. RNA was converted to cDNA using M-MuLV Reverse Transcriptase. cDNA was amplified using primers specific to the ism-2 transcript (SEQ ID NOs:71 and 72). The products of the RT-PCR reactions were visualized on an agarose gel stained with GelRed (VWR). The resulting gel image showed a clear signal at the correct size that was amplified from the RNA of events 7, 10, and 11, but not from event 25.

Following these qualitative RT-PCR experiments, quantitative RT-PCR (qRT-PCR) experiments were performed with the cDNA derived from the developing embryos of the plants described above. The primers used for amplification were SEQ ID NOs: 71 and 72. These qRT-PCR experiments produced the data shown in Table 14. As shown in this table, events 10-9, 10-5, and 11 accumulate transcript from the transgene at approximately 5.4, 7.7, and 20.8-times higher levels than event 7.

TABLE 14 qRT-PCR quantification of transgene expression levels

| Event | Fold Over Control |
|---|---|
| E7 | 0.13 ± 0.02 |
| E10-9 | 0.7 ± 0.2 |
| E10-5 | 1 ± 0.2 |
| E11 | 2.7 ± 0.2 |
| E25 | Run Error |
| WT Control | 0.0004 ± 0.0001 |

EXAMPLE 9

Determination of Yield Components in Greenhouse-Grown Maize

The plants that were used for the RT-PCR and qRT-PCR experiments described above were allowed to mature, and the resulting seeds were harvested in order to determine the yield components associated with these plants. Temperatures were controlled for the growth of these plants such that the average high temperature in the four days following pollination was 84° F. and the average low temperature in this same period was 74° F. Table 16 shows the yield data from these greenhouse-grown plants. This table shows that event 25, which did not show detectable transgene expression in RT-PCR and qRT-PCR experiments, had higher yield than event 11, with the highest expression levels, but lower yield than events 7 or 10, which both showed lower expression levels than event 11. Table 15 shows that the higher yields observed with events 7 and 10 resulted primarily from an increase in the number of seeds produced. Events 7 and 10 produced an average of 263 and 353 kernels per ear, respectively, while event 25 produced an average of 173 kernels per ear and event 11 produced an average of 92 kernels per ear. Ear weight, ear length, kernel count, and total seed weight differed significantly among the four events tested. Ear circumference and 100 kernel weight did not differ significantly among these events.

TABLE 15

Yield components of greenhouse-grown maize plants

| Event | Ear Weight (g) | Ear Length (cm) | Ear Circumference (cm) | 100 Kernel Weight (g) | Kernel Count | Total Seed Weight (g) |
|---|---|---|---|---|---|---|
| 25 | 47.02 | 8.80 | 12.60 | 18.05 | 186 | 33.57 |
|    | 45.12 | 7.60 | 13.30 | 22.06 | 129 | 28.46 |
|    | 62.86 | 11.10 | 12.70 | 22.78 | 198 | 45.10 |
|    | 55.98 | 7.90 | 13.60 | 23.60 | 178 | 42.01 |

TABLE 15-continued

Yield components of greenhouse-grown maize plants

| Event | Ear Weight (g) | Ear Length (cm) | Ear Circumference (cm) | 100 Kernel Weight (g) | Kernel Count | Total Seed Weight (g) |
|---|---|---|---|---|---|---|
| AVE | 52.75 | 8.85 | 13.05 | 21.62 | 173 | 37.29 |
| 11 | 52.68 | 6.70 | 14.50 | 25.84 | 124 | 32.04 |
|    | 41.06 | 7.40 | 13.20 | 23.00 | 101 | 23.23 |
|    | 18.72 | 4.40 | 11.00 | 18.78 | 50 | 9.39 |
| AVE | 37.49 | 6.17 | 12.90 | 22.54 | 92 | 21.55 |
| 7 | 59.04 | 10.30 | 12.90 | 22.30 | 223 | 49.73 |
|    | 77.54 | 11.50 | 12.70 | 19.92 | 302 | 60.16 |
|    | 75.98 | 9.80 | 13.30 | 23.30 | 263 | 61.28 |
| AVE | 70.85 | 10.53 | 12.97 | 21.84 | 263 | 57.06 |
| 10 | 85.52 | 11.40 | 14.00 | 21.96 | 353 | 77.52 |

All of the materials and methods disclosed and claimed herein can be made and used without undue experimentation as instructed by the above disclosure. Although the materials and methods of this invention have been described in terms of preferred embodiments and illustrative examples, it will be apparent to those of skill in the art that variations can be applied to the materials and methods described herein without departing from the concept, spirit and scope of this invention. All such similar substitutes and modifications apparent to those skilled in the art are deemed to be within the spirit, scope and concept of this invention as defined by the appended claims.

What is claimed is:

1. A polynucleotide comprising a sequence encoding a variant AGPase subunit polypeptide, said polypeptide comprising at least 70% identity to SEQ ID NO: 70 and comprising mutations at positions corresponding to amino acid 96, 161, and 443 of SEQ ID NO: 20 relative to a wild type AGPase subunit polypeptide.

2. The polynucleotide of claim 1, wherein said variant AGPase subunit polypeptide is an AGPase large subunit polypeptide.

3. The polynucleotide of claim 1, wherein said variant AGPase subunit polypeptide comprises a conserved motif having SEQ ID NO: 21, SEQ ID NO: 22, or SEQ ID NO: 23.

4. The polynucleotide of claim 1, wherein said polypeptide comprises at least 90% identity to SEQ ID NO:70.

5. The polynucleotide of claim 1, wherein said polypeptide comprises at least one mutation selected from the group consisting of a glycine or a glutamine at said position 161, an arginine or a glycine at said position 96, and an arginine at said position 443.

6. The polynucleotide of claim 1, wherein said polynucleotide is operably linked to a heterologous promoter functional in plants.

7. The polynucleotide of claim 1, wherein the polypeptide comprising said mutation relative to a wild type AGPase subunit polypeptide comprises SEQ ID NO: 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70.

8. A recombinant construct comprising the polynucleotide of claim 1.

9. A polypeptide encoded by the polynucleotide of claim 1.

10. A plant, seed, cell, or plant part comprising the polynucleotide of claim 1.

11. The plant, seed, cell, or plant part of claim 9, defined as a monocotyledonous plant, seed, cell, or plant part.

12. The plant, seed, cell, or plant part of claim 9, defined as a dicotyledonous plant, seed, cell, or plant part.

13. The plant, seed, cell, or plant part of claim 9, wherein said plant is selected from the group consisting of rice, wheat, barley, oats, rye, sorghum, maize, sugarcane, pineapple, onion, bananas, coconut, lilies, millet, tomato, potato, sweet potato, pea, strawberry, beet, chickpea, watermelon, muskmelon, cassava, taro, sunflower, flax, and beans.

14. A method of increasing the resistance of a plant to heat stress conditions or increasing starch biosynthesis of a plant comprising expressing in the plant the polynucleotide of claim 1.

15. The method of claim 14, wherein the plant is defined as a monocotyledonous plant.

16. The method of claim 14, wherein the plant is defined as a dicotyledonous plant.

17. The method of claim 14, wherein the plant is selected from the group consisting of rice, wheat, barley, oats, rye, sorghum, maize, sugarcane, pineapple, onion, bananas, coconut, lilies, millet, tomato, potato, sweet potato, pea, strawberry, beet, chickpea, watermelon, muskmelon, cassava, taro, sunflower, flax, and beans.

18. The method of claim 14, comprising transforming a plant cell with said polynucleotide and regenerating the plant therefrom.

19. The method of claim 14, comprising crossing a parent plant comprising said polynucleotide with itself or a second plant to obtain the plant in which resistance of a plant to heat stress conditions or starch biosynthesis is increased.

* * * * *

SEQUENCE LISTING

```
<160> NUMBER OF SEQ ID NOS: 72

<210> SEQ ID NO 1
<211> LENGTH: 40
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (12)..(13)
<223> OTHER INFORMATION: n is a, c, g, or t

<400> SEQUENCE: 1
gcactggatc tnnkctcttt cctctgacaa gcacaagagc                           40

<210> SEQ ID NO 2
<211> LENGTH: 40
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (13)..(14)
<223> OTHER INFORMATION: n is a, c, g, or t

<400> SEQUENCE: 2
agaggaaaga gmnnagatcc agtgcctccg cccaaaatga                           40

<210> SEQ ID NO 3
<211> LENGTH: 40
<212> TYPE: DNA
<213> ORGANISM: Artificial sequence
<220> FEATURE:
<223> OTHER INFORMATION: Primer
```

<220> FEATURE:
<221> NAME/KEY: misc_feature
<222> LOCATION: (12)..(13)
<223> OTHER INFORMATION: n is a, c, g, or t

<400> SEQUENCE: 3
tcaactttgc tnnkggatct gtacaggtat tagcggctac                              40

<210> SEQ ID NO 4
<211> LENGTH: 40
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (13)..(14)
<223> OTHER INFORMATION: n is a, c, g, or t

<400> SEQUENCE: 4
tgtacagatc cmnnagcaaa gttgatcccg ccttcaaggt                              40

<210> SEQ ID NO 5
<211> LENGTH: 40
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (12)..(13)
<223> OTHER INFORMATION: n is a, c, g, or t

<400> SEQUENCE: 5
tgagctatgc tnnkgatgat gcacagaaat atccatacct                              40

<210> SEQ ID NO 6
<211> LENGTH: 40
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (13)..(14)
<223> OTHER INFORMATION: n is a, c, g, or t

<400> SEQUENCE: 6
tgtgcatcat cmnnagcata gctcaggaag ttggtctcaa                              40

<210> SEQ ID NO 7
<211> LENGTH: 40
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (12)..(13)
<223> OTHER INFORMATION: n is a, c, g, or t

<400> SEQUENCE: 7
tagatgatgc annkaaatat ccataccttg catcaatggg                              40

<210> SEQ ID NO 8
<211> LENGTH: 40
<212> TYPE: DNA
<213> ORGANISM: Artificial sequence -continued

```
<220> FEATURE:
<223> OTHER INFORMATION: Primer
<220> FEATURE:
<221> NAME/KEY: misc_feature
<222> LOCATION: (13)..(14)
<223> OTHER INFORMATION: n is a, c, g, or t

<400> SEQUENCE: 8
tatggatatt tmnntgcatc atctatagca tagctcagga                40

<210> SEQ ID NO 9
<211> LENGTH: 40
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (12)..(13)
<223> OTHER INFORMATION: n is a, c, g, or t

<400> SEQUENCE: 9 attttttacga tnnkaaaaca cctttcttca ctgcaccccg                40

<210> SEQ ID NO 10
<211> LENGTH: 40
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (13)..(14)
<223> OTHER INFORMATION: n is a, c, g, or t

<400> SEQUENCE: 10
aaaggtgttt tmnnatcgta aaaatcaaac ttggaaggct                40

<210> SEQ ID NO 11
<211> LENGTH: 40
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (12)..(13)
<223> OTHER INFORMATION: n is a, c, g, or t

<400> SEQUENCE: 11
tctatgaaac tnnkgaagaa gcttcaaagc tactgttagc                40

<210> SEQ ID NO 12
<211> LENGTH: 40
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (13)..(14)
<223> OTHER INFORMATION: n is a, c, g, or t

<400> SEQUENCE: 12
gaagcttctt cmnnagtttc atagatgtcc gctcccatca                40

<210> SEQ ID NO 13
<211> LENGTH: 40
<212> TYPE: DNA
```

```
<213> ORGANISM: Artificial sequence
<220> FEATURE:
<223> OTHER INFORMATION: Primer
<220> FEATURE:
<221> NAME/KEY: misc_feature
<222> LOCATION: (12)..(13)
<223> OTHER INFORMATION: n is a, c, g, or t

<400> SEQUENCE: 13
ctgaagaaga annktcaaag ctactgttag ctgggaaggt                            40

<210> SEQ ID NO 14
<211> LENGTH: 40
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (13)..(14)
<223> OTHER INFORMATION: n is a, c, g, or t

<400> SEQUENCE: 14
agtagctttg amnnttcttc ttcagtttca tagatgtccg                            40

<210> SEQ ID NO 15
<211> LENGTH: 40
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (12)..(13)
<223> OTHER INFORMATION: n is a, c, g, or t

<400> SEQUENCE: 15
aagaagaagc tnnkaagcta ctgttagctg gaaggtccc                             40

<210> SEQ ID NO 16
<211> LENGTH: 40
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (13)..(14)
<223> OTHER INFORMATION: n is a, c, g, or t

<400> SEQUENCE: 16
aacagtagct tmnnagcttc ttcttcagtt tcatagatgt                            40

<210> SEQ ID NO 17
<211> LENGTH: 40
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (12)..(13)
<223> OTHER INFORMATION: n is a, c, g, or t

<400> SEQUENCE: 17
aagaagcttc annkctactg ttagctggga aggtcccagt                            40

<210> SEQ ID NO 18
<211> LENGTH: 40
```

<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (13)..(14)
<223> OTHER INFORMATION: n is a, c, g, or t

<400> SEQUENCE: 18
gctaacagta gmnntgaagc ttcttcttca gtttcataga                                40

<210> SEQ ID NO 19
<211> LENGTH: 1551
<212> TYPE: DNA
<213> ORGANISM: Zea mays

<400> SEQUENCE: 19
atgcagtttg cacttgcatt ggacacgaac tcaggtcctc accagataag atcttgtgag        60
ggtgatggga ttgacaggtt ggaaaaatta agtattgggg cagaaagca ggagaaagct         120
ttgagaaata ggtgctttgg tggtagagtt gctgcaacta cacaatgtat tcttacctca        180
gatgcttgtc ctgaaactct tcattctcaa acacagtcct ctaggaaaaa ttatgctgat        240
gcaaaccgtg tatctgcgat cattttgggc ggaggcactg atctcagct ctttcctctg         300
acaagcacaa gagctacgcc tgctgtacct gttggaggat gttacaggct tattgatatc        360
cctatgagta actgcttcaa cagtggtata aataagatat tgtgatgag tcagttcaat         420
tctacttcgc ttaaccgcca tattcatcgt acataccttg aaggcgggat caactttgct        480
gatggatctg tacaggtatt agcggctaca caaatgcctg aagagccagc tggatggttc        540
cagggtacag cagactctat cagaaaattt atctgggtac tcgaggatta ttacagtcac        600
aaatccattg acaacattgt aatcttgagt ggcgatcagc tttatcggat gaattacatg        660
gaacttgtgc agaaacatgt cgaggacgat gctgatatca ctatatcatg tgctcctgtt        720
gatgagagcc gagcttctaa aaatgggcta gtgaagattg atcatactgg acgtgtactt        780
caattctttg aaaaaccaaa gggtgctgat ttgaattcta tgagagttga gaccaacttc        840
ctgagctatg ctatagatga tgcacagaaa tatccatacc ttgcatcaat gggcatttat        900
gtcttcaaga aagatgcact tttagacctt ctcaagtcaa aatatactca attacatgac        960
tttggatctg aaatcctccc aagagctgta ctagatcata gtgtgcaggc atgcattttt       1020
acgggctatt gggaggatgt tggaacaatc aaatcattct ttgatgcaaa cttggccctc       1080
actgagcagc cttccaagtt tgattttta c gatccaaaaa caccttttctt cactgcaccc    1140
cgatgcttgc ctccgacgca attggacaag tgcaagatga aatatgcatt tatctcagat       1200
ggttgcttac tgagagaatg caacatcgag cattctgtga ttggagtctg ctcacgtgtc       1260
agctctggat gtgaactcaa ggactccgtg atgatgggag cggacatcta tgaaactgaa       1320
gaagaagctt caaagctact gttagctggg aaggtcccga ttggaatagg aaggaacaca       1380
aagataagga actgtatcat tgacatgaat gctaggattg ggaagaacgt ggtgatcaca       1440
aacagtaagg gcatccaaga ggctgatcac ccggaagaag ggtactacat aaggtctgga       1500
atcgtggtga tcctgaagaa tgcaaccatc aacgatgggt ctgtcatata g                1551

<210> SEQ ID NO 20
<211> LENGTH: 516
<212> TYPE: PRT
<213> ORGANISM: Zea mays

```
<400> SEQUENCE: 20

Met Gln Phe Ala Leu Ala Leu Asp Thr Asn Ser Gly Pro His Gln Ile
1               5                   10                  15

Arg Ser Cys Glu Gly Asp Gly Ile Asp Arg Leu Glu Lys Leu Ser Ile
            20                  25                  30

Gly Gly Arg Lys Gln Glu Lys Ala Leu Arg Asn Arg Cys Phe Gly Gly
        35                  40                  45

Arg Val Ala Ala Thr Thr Gln Cys Ile Leu Thr Ser Asp Ala Cys Pro
    50                  55                  60

Glu Thr Leu His Ser Gln Thr Gln Ser Ser Arg Lys Asn Tyr Ala Asp
65                  70                  75                  80

Ala Asn Arg Val Ser Ala Ile Ile Leu Gly Gly Thr Gly Ser Gln
                85                  90                  95

Leu Phe Pro Leu Thr Ser Thr Arg Ala Thr Pro Ala Val Pro Val Gly
            100                 105                 110

Gly Cys Tyr Arg Leu Ile Asp Ile Pro Met Ser Asn Cys Phe Asn Ser
        115                 120                 125

Gly Ile Asn Lys Ile Phe Val Met Ser Gln Phe Asn Ser Thr Ser Leu
    130                 135                 140

Asn Arg His Ile His Arg Thr Tyr Leu Glu Gly Gly Ile Asn Phe Ala
145                 150                 155                 160

Asp Gly Ser Val Gln Val Leu Ala Ala Thr Gln Met Pro Glu Glu Pro
                165                 170                 175

Ala Gly Trp Phe Gln Gly Thr Ala Asp Ser Ile Arg Lys Phe Ile Trp
            180                 185                 190

Val Leu Glu Asp Tyr Tyr Ser His Lys Ser Ile Asp Asn Ile Val Ile
        195                 200                 205

Leu Ser Gly Asp Gln Leu Tyr Arg Met Asn Tyr Met Glu Leu Val Gln
    210                 215                 220

Lys His Val Glu Asp Asp Ala Asp Ile Thr Ile Ser Cys Ala Pro Val
225                 230                 235                 240

Asp Glu Ser Arg Ala Ser Lys Asn Gly Leu Val Lys Ile Asp His Thr
                245                 250                 255

Gly Arg Val Leu Gln Phe Phe Glu Lys Pro Lys Gly Ala Asp Leu Asn
            260                 265                 270

Ser Met Arg Val Glu Thr Asn Phe Leu Ser Tyr Ala Ile Asp Asp Ala
        275                 280                 285

Gln Lys Tyr Pro Tyr Leu Ala Ser Met Gly Ile Tyr Val Phe Lys Lys
    290                 295                 300

Asp Ala Leu Leu Asp Leu Leu Lys Ser Lys Tyr Thr Gln Leu His Asp
305                 310                 315                 320

Phe Gly Ser Glu Ile Leu Pro Arg Ala Val Leu Asp His Ser Val Gln
                325                 330                 335

Ala Cys Ile Phe Thr Gly Tyr Trp Glu Asp Val Gly Thr Ile Lys Ser
            340                 345                 350

Phe Phe Asp Ala Asn Leu Ala Leu Thr Glu Gln Pro Ser Lys Phe Asp
        355                 360                 365

Phe Tyr Asp Pro Lys Thr Pro Phe Phe Thr Ala Pro Arg Cys Leu Pro
    370                 375                 380

Pro Thr Gln Leu Asp Lys Cys Lys Met Lys Tyr Ala Phe Ile Ser Asp
385                 390                 395                 400

Gly Cys Leu Leu Arg Glu Cys Asn Ile Glu His Ser Val Ile Gly Val
                405                 410                 415
```

```
Cys Ser Arg Val Ser Ser Gly Cys Glu Leu Lys Asp Ser Val Met Met
            420                 425                 430

Gly Ala Asp Ile Tyr Glu Thr Glu Glu Ala Ser Lys Leu Leu Leu
            435                 440                 445

Ala Gly Lys Val Pro Ile Gly Ile Gly Arg Asn Thr Lys Ile Arg Asn
450                 455                 460

Cys Ile Ile Asp Met Asn Ala Arg Ile Gly Lys Asn Val Val Ile Thr
465                 470                 475                 480

Asn Ser Lys Gly Ile Gln Glu Ala Asp His Pro Glu Glu Gly Tyr Tyr
                485                 490                 495

Ile Arg Ser Gly Ile Val Val Ile Leu Lys Asn Ala Thr Ile Asn Asp
            500                 505                 510

Gly Ser Val Ile
        515

<210> SEQ ID NO 21
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 21

Phe Xaa Xaa Gly Xaa Val Xaa Val Leu Ala
1               5                   10

<210> SEQ ID NO 22
<211> LENGTH: 13
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 22

Leu Gly Gly Gly Xaa Gly Xaa Xaa Leu Phe Pro Leu Thr
1               5                   10

<210> SEQ ID NO 23
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (2)..(2)
<223> OTHER INFORMATION: Xaa can be any naturally occurring amino acid
```

```
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(9)
<223> OTHER INFORMATION: Xaa can be any naturally occurring amino acid

<400> SEQUENCE: 23

Tyr Xaa Thr Glu Xaa Glu Xaa Xaa Xaa Leu Leu
1               5                   10

<210> SEQ ID NO 24
<211> LENGTH: 42
<212> TYPE: DNA
<213> ORGANISM: Artificial sequence
<220> FEATURE:
<223> OTHER INFORMATION: Primer

<400> SEQUENCE: 24
gcgggatcaa ctttgctggt gggtctgtac aggtattagc gg                              42

<210> SEQ ID NO 25
<211> LENGTH: 42
<212> TYPE: DNA
<213> ORGANISM: Artificial sequence
<220> FEATURE:
<223> OTHER INFORMATION: Primer

<400> SEQUENCE: 25
ccgctaatac ctgtacagac ccaccagcaa agttgatccc gc                              42

<210> SEQ ID NO 26
<211> LENGTH: 47
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (25)..(26)
<223> OTHER INFORMATION: n is a, c, g, or t

<400> SEQUENCE: 26
gagaccaact tcctgtccta tgctnnkgat gatgcacaga aatatcc                         47

<210> SEQ ID NO 27
<211> LENGTH: 47
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (22)..(23)
<223> OTHER INFORMATION: n is a, c, g, or t

<400> SEQUENCE: 27
ggatatttct gtgcatcatc mnnagcatag gacaggaagt tggtctc                         47

<210> SEQ ID NO 28
<211> LENGTH: 43
<212> TYPE: DNA
<213> ORGANISM: Artificial sequence
<220> FEATURE:
<223> OTHER INFORMATION: Primer
<220> FEATURE:
<221> NAME/KEY: misc_feature
```

<222> LOCATION: (21)..(22)
<223> OTHER INFORMATION: n is a, c, g, or t

<400> SEQUENCE: 28
gctatgctat agatgatgct nnkaaatatc cataccttgc atc                    43

<210> SEQ ID NO 29
<211> LENGTH: 43
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (22)..(23)
<223> OTHER INFORMATION: n is a, c, g, or t

<400> SEQUENCE: 29
gatgcaaggt atggatattt mnnagcatca tctatagcat agc                    43

<210> SEQ ID NO 30
<211> LENGTH: 51
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (25)..(26)
<223> OTHER INFORMATION: n is a, c, g, or t

<400> SEQUENCE: 30
ccttccaagt tgatttttta cgacnnkaaa acacctttct tcactgcacc c            51

<210> SEQ ID NO 31
<211> LENGTH: 51
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (26)..(27)
<223> OTHER INFORMATION: n is a, c, g, or t

<400> SEQUENCE: 31
gggtgcagtg aagaaaggtg ttttmnngtc gtaaaaatca aacttggaag g            51

<210> SEQ ID NO 32
<211> LENGTH: 50
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (22)..(23)
<223> OTHER INFORMATION: n is a, c, g, or t

<400> SEQUENCE: 32
ggagcggaca tctatgaaac tnnkgaagag gcttcaaagc tactgttagc              50

<210> SEQ ID NO 33
<211> LENGTH: 50
<212> TYPE: DNA
<213> ORGANISM: Artificial sequence
<220> FEATURE:
<223> OTHER INFORMATION: Primer
<220> FEATURE:

<221> NAME/KEY: misc_feature
<222> LOCATION: (28)..(29)
<223> OTHER INFORMATION: n is a, c, g, or t

<400> SEQUENCE: 33
gctaacagta gctttgaagc ctcttcmnna gtttcataga tgtccgctcc    50

<210> SEQ ID NO 34
<211> LENGTH: 49
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (27)..(28)
<223> OTHER INFORMATION: n is a, c, g, or t

<400> SEQUENCE: 34
cggacatcta tgaaactgaa gaagaannkt caaagctact gttagctgg    49

<210> SEQ ID NO 35
<211> LENGTH: 49
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (22)..(23)
<223> OTHER INFORMATION: n is a, c, g, or t

<400> SEQUENCE: 35
ccagctaaca gtagctttga mnnttcttct tcagtttcat agatgtccg    49

<210> SEQ ID NO 36
<211> LENGTH: 50
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (26)..(27)
<223> OTHER INFORMATION: n is a, c, g, or t

<400> SEQUENCE: 36
catctatgaa actgaagaag aagcgnnkaa gctactgtta gctgggaagg    50

<210> SEQ ID NO 37
<211> LENGTH: 50
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (24)..(25)
<223> OTHER INFORMATION: n is a, c, g, or t

<400> SEQUENCE: 37
ccttcccagc taacagtagc ttmnncgctt cttcttcagt ttcatagatg    50

<210> SEQ ID NO 38
<211> LENGTH: 52
<212> TYPE: DNA
<213> ORGANISM: Artificial sequence
<220> FEATURE:
<223> OTHER INFORMATION: Primer

```
<220> FEATURE:
<221> NAME/KEY: misc_feature
<222> LOCATION: (29)..(30)
<223> OTHER INFORMATION: n is a, c, g, or t

<400> SEQUENCE: 38
catctatgaa actgaagaag aagcgtcann kctactgtta gctgggaagg tc          52

<210> SEQ ID NO 39
<211> LENGTH: 52
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (23)..(24)
<223> OTHER INFORMATION: n is a, c, g, or t

<400> SEQUENCE: 39
gaccttccca gctaacagta gmnntgacgc ttcttcttca gtttcataga tg          52

<210> SEQ ID NO 40
<211> LENGTH: 516
<212> TYPE: PRT
<213> ORGANISM: Zea mays

<400> SEQUENCE: 40
```

| Met | Gln | Phe | Ala | Leu | Ala | Leu | Asp | Thr | Asn | Ser | Gly | Pro | His | Gln | Ile |
|---|---|---|---|---|---|---|---|---|---|---|---|---|---|---|---|
| 1 | | | | 5 | | | | | 10 | | | | | 15 | |

| Arg | Ser | Cys | Glu | Gly | Asp | Gly | Ile | Asp | Arg | Leu | Glu | Lys | Leu | Ser | Ile |
| | | | 20 | | | | | 25 | | | | | 30 | | |

| Gly | Gly | Arg | Lys | Gln | Glu | Lys | Ala | Leu | Arg | Asn | Arg | Cys | Phe | Gly | Gly |
| | | 35 | | | | | 40 | | | | | 45 | | | |

| Arg | Val | Ala | Ala | Thr | Thr | Gln | Cys | Ile | Leu | Thr | Ser | Asp | Ala | Cys | Pro |
| 50 | | | | | 55 | | | | | 60 | | | | | |

| Glu | Thr | Leu | His | Ser | Gln | Thr | Gln | Ser | Ser | Arg | Lys | Asn | Tyr | Ala | Asp |
| 65 | | | | 70 | | | | | 75 | | | | | 80 | |

| Ala | Asn | Arg | Val | Ser | Ala | Ile | Ile | Leu | Gly | Gly | Gly | Thr | Gly | Ser | Gln |
| | | | 85 | | | | | 90 | | | | | 95 | | |

| Leu | Phe | Pro | Leu | Thr | Ser | Thr | Arg | Ala | Thr | Pro | Ala | Val | Pro | Val | Gly |
| | | | 100 | | | | | 105 | | | | | 110 | | |

| Gly | Cys | Tyr | Arg | Leu | Ile | Asp | Ile | Pro | Met | Ser | Asn | Cys | Phe | Asn | Ser |
| | | 115 | | | | | 120 | | | | | 125 | | | |

| Gly | Ile | Asn | Lys | Ile | Phe | Val | Met | Ser | Gln | Phe | Asn | Ser | Thr | Ser | Leu |
| | 130 | | | | | 135 | | | | | 140 | | | | |

| Asn | Arg | His | Ile | His | Arg | Thr | Tyr | Leu | Glu | Gly | Gly | Ile | Asn | Phe | Ala |
| 145 | | | | | 150 | | | | | 155 | | | | | 160 |

| Asp | Gly | Ser | Val | Gln | Val | Leu | Ala | Ala | Thr | Gln | Met | Pro | Glu | Glu | Pro |
| | | | 165 | | | | | 170 | | | | | 175 | | |

| Ala | Gly | Trp | Phe | Gln | Gly | Thr | Ala | Asp | Ser | Ile | Arg | Lys | Phe | Ile | Trp |
| | | | 180 | | | | | 185 | | | | | 190 | | |

| Val | Leu | Glu | Asp | Tyr | Tyr | Ser | His | Lys | Ser | Ile | Asp | Asn | Ile | Val | Ile |
| | | | 195 | | | | | 200 | | | | | 205 | | |

| Leu | Ser | Gly | Asp | Gln | Leu | Tyr | Arg | Met | Asn | Tyr | Met | Glu | Leu | Val | Gln |
| | | 210 | | | | | 215 | | | | | 220 | | | |

| Lys | His | Val | Glu | Asp | Asp | Ala | Asp | Ile | Thr | Ile | Ser | Cys | Ala | Pro | Val |
| 225 | | | | | 230 | | | | | 235 | | | | | 240 |

| Asp | Glu | Ser | Arg | Ala | Ser | Lys | Asn | Gly | Leu | Val | Lys | Ile | Asp | His | Thr |

|   |   |   | 245 |   |   |   | 250 |   |   |   | 255 |   |

Gly Arg Val Leu Gln Phe Phe Glu Lys Pro Lys Gly Ala Asp Leu Asn
                260                 265                 270

Ser Met Arg Val Glu Thr Asn Phe Leu Ser Tyr Ala Ile Asp Asp Ala
            275                 280                 285

Gln Lys Tyr Pro Tyr Leu Ala Ser Met Gly Ile Tyr Val Phe Lys Lys
        290                 295                 300

Asp Ala Leu Leu Asp Leu Leu Lys Ser Lys Tyr Thr Gln Leu His Asp
305                 310                 315                 320

Phe Gly Ser Glu Ile Leu Pro Arg Ala Val Leu Asp His Ser Val Gln
                325                 330                 335

Ala Cys Ile Phe Thr Gly Tyr Trp Glu Asp Val Gly Thr Ile Lys Ser
            340                 345                 350

Phe Phe Asp Ala Asn Leu Ala Leu Thr Glu Gln Pro Ser Lys Phe Asp
        355                 360                 365

Phe Tyr Asp Pro Lys Thr Pro Phe Phe Thr Ala Pro Arg Cys Leu Pro
    370                 375                 380

Pro Thr Gln Leu Asp Lys Cys Lys Met Lys Tyr Ala Phe Ile Ser Asp
385                 390                 395                 400

Gly Cys Leu Leu Arg Glu Cys Asn Ile Glu His Ser Val Ile Gly Val
                405                 410                 415

Cys Ser Arg Val Ser Ser Gly Cys Glu Leu Lys Asp Ser Val Met Met
            420                 425                 430

Gly Ala Asp Thr Tyr Glu Thr Glu Glu Ala Ser Lys Leu Leu Leu
        435                 440                 445

Ala Gly Lys Val Pro Val Gly Ile Gly Arg Asn Thr Lys Ile Arg Asn
    450                 455                 460

Cys Ile Ile Asp Met Asn Ala Arg Ile Gly Lys Asn Val Val Ile Thr
465                 470                 475                 480

Asn Ser Lys Gly Ile Gln Glu Ala Asp His Pro Glu Gly Tyr Tyr
                485                 490                 495

Ile Arg Ser Gly Ile Val Val Ile Leu Lys Asn Ala Thr Ile Asn Asp
            500                 505                 510

Gly Ser Val Ile
        515

<210> SEQ ID NO 41
<211> LENGTH: 521
<212> TYPE: PRT
<213> ORGANISM: Zea mays

<400> SEQUENCE: 41

Met Gln Phe Ser Ser Val Leu Pro Leu Glu Gly Lys Ala Cys Met Ser
1               5                   10                  15

Pro Val Arg Arg Gly Ser Gly Gly Tyr Gly Ser Glu Arg Met Arg Ile
            20                  25                  30

Asn Cys Cys Ser Ile Arg Arg Asn Lys Ala Leu Arg Arg Met Cys Phe
        35                  40                  45

Ser Ala Arg Gly Ala Val Ser Ser Thr Gln Cys Val Leu Thr Ser Asp
    50                  55                  60

Ala Gly Pro Asp Thr Leu Val Arg Pro Asn His Pro Phe Arg Arg Asn
65                  70                  75                  80

Tyr Ala Asp Pro Asn Glu Val Ala Ala Val Ile Leu Gly Gly Gly Thr
                85                  90                  95

```
Gly Thr Gln Leu Phe Pro Leu Thr Ser Thr Arg Ala Thr Pro Ala Val
            100                 105                 110

Pro Ile Gly Gly Cys Tyr Arg Leu Ile Asp Ile Pro Met Ser Asn Cys
        115                 120                 125

Phe Asn Ser Gly Ile Asn Lys Ile Phe Val Met Thr Gln Phe Asn Ser
130                 135                 140

Ala Ser Leu Asn Arg His Ile His Arg Thr Tyr Leu Gly Gly Gly Ile
145                 150                 155                 160

Asn Phe Thr Asp Gly Ser Val Glu Val Leu Ala Ala Thr Gln Met Pro
                165                 170                 175

Gly Glu Ala Ala Gly Trp Phe Gln Gly Thr Ala Asp Ala Val Arg Lys
            180                 185                 190

Phe Ile Trp Val Leu Glu Asp Tyr Tyr Lys His Lys Ala Ile Glu His
        195                 200                 205

Ile Leu Ile Leu Ser Gly Asp Gln Leu Tyr Arg Met Asp Tyr Met Glu
        210                 215                 220

Leu Val Gln Lys His Val Asp Asp Asn Ala Asp Ile Thr Leu Ser Cys
225                 230                 235                 240

Ala Pro Val Gly Glu Ser Arg Ala Ser Asp Tyr Gly Leu Val Lys Phe
                245                 250                 255

Asp Ser Ser Gly Arg Val Ile Gln Phe Ser Glu Lys Pro Lys Gly Ala
                260                 265                 270

Ala Leu Glu Glu Met Lys Val Asp Thr Ser Phe Leu Asn Phe Ala Thr
            275                 280                 285

Cys Thr Leu Pro Ala Glu Tyr Pro Tyr Ile Ala Ser Met Gly Val Tyr
        290                 295                 300

Val Phe Lys Arg Asp Val Leu Leu Asp Leu Leu Lys Ser Arg Tyr Ala
305                 310                 315                 320

Glu Leu His Asp Phe Gly Ser Glu Ile Leu Pro Lys Ala Leu His Glu
                325                 330                 335

His Asn Val Gln Ala Tyr Val Phe Thr Asp Tyr Trp Glu Asp Ile Gly
            340                 345                 350

Thr Ile Arg Ser Phe Phe Asp Ala Asn Met Ala Leu Cys Glu Gln Pro
        355                 360                 365

Pro Lys Phe Glu Phe Tyr Asp Pro Lys Thr Pro Phe Phe Thr Ser Pro
        370                 375                 380

Arg Tyr Leu Pro Pro Thr Lys Ser Asp Lys Cys Arg Ile Lys Asp Ala
385                 390                 395                 400

Ile Ile Ser His Gly Cys Phe Leu Arg Glu Cys Ala Ile Glu His Ser
                405                 410                 415

Ile Val Gly Val Pro Ser Arg Leu Asn Ser Gly Cys Glu Leu Lys Asn
            420                 425                 430

Thr Met Met Met Gly Ala Asp Leu Tyr Glu Thr Glu Asp Glu Ile Ser
        435                 440                 445

Arg Leu Leu Ala Glu Gly Lys Val Pro Ile Gly Val Gly Glu Asn Thr
        450                 455                 460

Lys Ile Ser Asn Cys Ile Ile Asp Met Asn Cys Gln Gly Trp Lys Glu
465                 470                 475                 480

Arg Leu His Asn Lys Gln Arg Gly Arg Ser Lys Ser Pro Asp Arg Pro
                485                 490                 495

Gly Arg Arg Ile Leu Ile Arg Ser Gly Ile Val Val Leu Lys Asn
            500                 505                 510

Ala Thr Ile Lys Asp Gly Thr Val Ile
```

-continued

<210> SEQ ID NO 42
<211> LENGTH: 505
<212> TYPE: PRT
<213> ORGANISM: Zea mays

<400> SEQUENCE: 42

Met Gly Leu Arg Val Ala Ala Thr Ala Pro Ala Pro Ala Gly Val Arg
1               5                   10                  15

Val Leu Gly Arg Gly Ala Ala Arg Val Thr Pro Arg Pro Trp Ala Ala
                20                  25                  30

Val Gly Gly Arg Arg Arg Phe Ser Val Arg Met Ser Val Ala Thr Thr
            35                  40                  45

Glu Ala Thr Thr Thr Ile Ala Val Gly Ala Ser Glu Asp Gln Ala Leu
        50                  55                  60

Glu Ala Arg Asn Ser Lys Thr Val Val Ala Val Ile Leu Gly Gly Gly
65                  70                  75                  80

Ala Gly Thr Arg Leu Phe Pro Leu Thr Arg Arg Ala Lys Pro Ala
                85                  90                  95

Val Pro Ile Gly Gly Ala Tyr Arg Leu Ile Asp Val Pro Met Ser Asn
            100                 105                 110

Cys Ile Asn Ser Gly Ile Asn Lys Val Tyr Ile Leu Thr Gln Phe Asn
        115                 120                 125

Ser Gln Ser Leu Asn Arg His Leu Ser Arg Ala Tyr Asp Phe Ser Asn
    130                 135                 140

Gly Val Ala Ile Gly Asp Gly Phe Val Glu Val Leu Ala Ala Thr Gln
145                 150                 155                 160

Arg Pro Gly Thr Glu Gly Lys Arg Trp Phe Gln Gly Thr Ala Asp Ala
                165                 170                 175

Val Arg Gln Phe Asp Trp Leu Phe Asp Asp Ala Lys Ser Lys Asp Ile
            180                 185                 190

Glu Asp Val Leu Ile Leu Ser Gly Asp His Leu Tyr Arg Met Asp Tyr
        195                 200                 205

Met Asp Phe Val Gln Ser His Arg Gln Arg Gly Ala Gly Ile Ser Ile
    210                 215                 220

Cys Cys Leu Pro Ile Asp Gly Ser Arg Ala Ser Asp Phe Gly Leu Met
225                 230                 235                 240

Lys Ile Asp Asp Thr Gly Arg Val Ile Ser Phe Ser Glu Lys Pro Lys
                245                 250                 255

Gly Asp Glu Leu Lys Ala Met Gln Val Asp Thr Thr Val Leu Gly Leu
            260                 265                 270

Ser Lys Glu Glu Ala Glu Asn Lys Pro Tyr Ile Ala Ser Met Gly Ile
        275                 280                 285

Tyr Ile Phe Lys Lys Asp Ile Leu Leu Asn Leu Leu Arg Trp Arg Phe
    290                 295                 300

Pro Thr Ala Asn Asp Phe Gly Ser Glu Ile Ile Pro Ala Ser Ala Lys
305                 310                 315                 320

Glu Ile Asp Val Lys Ala Tyr Leu Phe Asn Asp Tyr Trp Glu Asp Ile
                325                 330                 335

Gly Thr Ile Lys Ser Phe Phe Glu Ala Asn Leu Ala Leu Ala Glu Gln
            340                 345                 350

Pro Pro Arg Phe Ser Phe Tyr Asp Ala Asp Lys Pro Met Tyr Thr Ser
        355                 360                 365

```
Arg Arg Asn Leu Pro Pro Ser Met Val Asn Asn Ser Lys Ile Thr Asp
    370                 375                 380

Ser Ile Ile Ser His Gly Cys Phe Leu Asp Asn Cys Arg Ile Glu His
385                 390                 395                 400

Ser Val Val Gly Val Arg Ser Arg Ile Gly Ser Asn Val His Leu Lys
                405                 410                 415

Asp Thr Val Met Leu Gly Ala Asp Tyr Tyr Glu Thr Ala Val Glu Arg
                420                 425                 430

Gly Glu Leu Leu Ala Glu Gly Lys Val Pro Ile Gly Ile Gly Glu Asn
                435                 440                 445

Thr Thr Ile Gln Lys Cys Ile Ile Asp Lys Asn Ala Arg Ile Gly Lys
    450                 455                 460

Lys Val Val Ile Ser Asn Ser Glu Gly Val Asp Glu Ala Asp Arg Thr
465                 470                 475                 480

Ser Glu Gly Phe Tyr Ile Arg Ser Gly Ile Thr Val Val Leu Lys Asn
                485                 490                 495

Ala Ile Ile Ala Asp Gly Leu Val Ile
                500                 505

<210> SEQ ID NO 43
<211> LENGTH: 523
<212> TYPE: PRT
<213> ORGANISM: Hordeum vulgare

<400> SEQUENCE: 43

Met Ser Ser Met Gln Phe Ser Ser Val Leu Pro Leu Glu Gly Lys Ala
1               5                   10                  15

Cys Val Ser Pro Val Arg Arg Glu Gly Ser Ala Cys Glu Arg Leu Lys
                20                  25                  30

Ile Gly Asp Ser Ser Ile Arg His Glu Arg Ala Ser Arg Arg Met
            35                  40                  45

Cys Asn Gly Gly Ala Arg Gly Pro Ala Ala Thr Gly Ala Gln Cys Val
    50                  55                  60

Leu Thr Ser Asp Ala Ser Pro Ala Asp Thr Leu Val Leu Arg Thr Ser
65                  70                  75                  80

Phe Arg Arg Asn Tyr Ala Asp Pro Asn Glu Val Ala Ala Val Ile Leu
                85                  90                  95

Gly Gly Gly Thr Gly Thr Gln Leu Phe Pro Leu Thr Ser Thr Arg Ala
                100                 105                 110

Thr Pro Ala Val Pro Ile Gly Gly Cys Tyr Arg Leu Ile Asp Ile Pro
            115                 120                 125

Met Ser Asn Cys Phe Asn Ser Gly Ile Asn Lys Ile Phe Val Met Thr
    130                 135                 140

Gln Phe Asn Ser Ala Ser Leu Asn Arg His Ile His Arg Thr Tyr Leu
145                 150                 155                 160

Gly Gly Gly Ile Asn Phe Thr Asp Gly Ser Val Glu Val Leu Ala Ala
                165                 170                 175

Thr Gln Met Pro Gly Glu Ala Ala Gly Trp Phe Arg Gly Thr Ala Asp
            180                 185                 190

Ala Val Arg Lys Phe Ile Trp Val Leu Glu Asp Tyr Tyr Lys His Lys
            195                 200                 205

Ser Ile Glu His Ile Leu Ile Leu Ser Gly Asp Gln Leu Tyr Arg Met
    210                 215                 220

Asp Tyr Met Glu Leu Val Gln Lys His Val Asp Asp Asn Ala Asp Ile
225                 230                 235                 240
```

-continued

```
Thr Leu Ser Cys Ala Pro Val Gly Glu Ser Arg Ala Ser Glu Tyr Gly
                245                 250                 255

Leu Val Lys Phe Asp Ser Ser Gly Arg Val Ile Gln Phe Ser Glu Lys
            260                 265                 270

Pro Lys Gly Asp Asp Leu Glu Ala Met Lys Val Asp Thr Ser Phe Leu
        275                 280                 285

Asn Phe Ala Ile Asp Asp Pro Ala Lys Tyr Pro Tyr Ile Ala Ser Met
    290                 295                 300

Gly Val Tyr Val Phe Lys Arg Asp Val Leu Leu Asn Leu Leu Lys Ser
305                 310                 315                 320

Arg Tyr Ala Glu Leu His Asp Phe Gly Ser Glu Ile Leu Pro Arg Ala
                325                 330                 335

Leu His Asp His Asn Val Gln Ala Tyr Val Phe Thr Asp Tyr Trp Glu
            340                 345                 350

Asp Ile Gly Thr Ile Arg Ser Phe Phe Asp Ala Asn Met Ala Leu Cys
        355                 360                 365

Glu Gln Pro Pro Lys Phe Glu Phe Tyr Asp Pro Lys Thr Pro Phe Phe
    370                 375                 380

Thr Ser Pro Arg Tyr Leu Pro Pro Thr Lys Ser Asp Lys Cys Arg Ile
385                 390                 395                 400

Lys Glu Ala Ile Ile Ser His Gly Cys Phe Leu Arg Glu Cys Lys Ile
                405                 410                 415

Glu His Ser Ile Ile Gly Val Arg Ser Arg Leu Asn Ser Gly Ser Glu
            420                 425                 430

Leu Lys Asn Ala Met Met Met Gly Ala Asp Ser Tyr Glu Thr Glu Asp
        435                 440                 445

Glu Ile Ser Arg Leu Met Ser Glu Gly Lys Val Pro Ile Gly Val Gly
    450                 455                 460

Glu Asn Thr Lys Ile Ser Asn Cys Ile Ile Asp Met Asn Ala Arg Ile
465                 470                 475                 480

Gly Arg Asp Val Val Ile Ser Asn Lys Glu Gly Val Gln Glu Ala Asp
                485                 490                 495

Arg Pro Glu Glu Gly Tyr Tyr Ile Arg Ser Gly Ile Val Ile Gln
            500                 505                 510

Lys Asn Ala Thr Ile Lys Asp Gly Thr Val Val
        515                 520
```

<210> SEQ ID NO 44
<211> LENGTH: 503
<212> TYPE: PRT
<213> ORGANISM: Hordeum vulgare

<400> SEQUENCE: 44

```
Met Asp Leu Arg Val Ala Ala Pro Ala Ser Val Ala Ala Ala Ala Arg
1               5                   10                  15

Arg Gly Ala Leu Gly Cys Ala Arg Val Arg Pro Leu Gln Gly Arg Arg
            20                  25                  30

Gln Cys Arg Pro Ser Val Arg Val Ser Val Ala Thr Thr Glu Ser Ala
        35                  40                  45

Ala Ala Ala Ala Val Ser Ala Ser Ala Asp Glu Asp Ala Glu Thr
    50                  55                  60

Thr Asn Pro Arg Thr Val Val Ala Val Ile Leu Gly Gly Gly Ala Gly
65                  70                  75                  80

Thr Arg Leu Phe Pro Leu Thr Lys Arg Arg Ala Lys Pro Ala Val Pro
```

```
            85                  90                  95
Ile Gly Gly Ala Tyr Arg Leu Ile Asp Val Pro Met Ser Asn Cys Ile
            100                 105                 110

Asn Ser Gly Ile Asn Lys Val Tyr Val Leu Thr Gln Phe Asn Ser Ala
            115                 120                 125

Ser Leu Asn Arg His Leu Phe Arg Ala Tyr Asn Phe Ser Asn Gly Val
            130                 135                 140

Gly Phe Gly Asp Gly Phe Val Glu Val Leu Ala Thr Gln Arg Pro
145                 150                 155                 160

Gly Ser Glu Gly Lys Arg Trp Phe Gln Gly Thr Ala Asp Ala Val Arg
                165                 170                 175

Gln Phe Ala Trp Leu Phe Asp Ala Lys Ser Lys Asp Ile Glu Asp
                180                 185                 190

Val Leu Ile Leu Ser Gly Asp His Leu Tyr Arg Met Asp Tyr Met Asp
                195                 200                 205

Phe Val Gln Ser His Arg Gln Arg Asp Ala Gly Ile Ser Ile Cys Cys
                210                 215                 220

Leu Pro Ile Asp Asp Ser Arg Ala Ser Asp Phe Gly Leu Met Lys Ile
225                 230                 235                 240

Asp Asp Thr Gly Arg Val Ile Ser Phe Ser Glu Lys Pro Lys Gly Ala
                245                 250                 255

Asp Leu Lys Ala Met Gln Val Asp Thr Thr Leu Leu Gly Leu Pro Lys
                260                 265                 270

Glu Glu Ala Glu Lys Lys Pro Tyr Ile Ala Ser Met Gly Val Tyr Ile
                275                 280                 285

Phe Lys Lys Glu Ile Leu Leu Asn Leu Leu Arg Trp Arg Phe Pro Thr
290                 295                 300

Ala Asn Asp Phe Gly Ser Glu Ile Ile Pro Ala Ala Arg Glu Ile
305                 310                 315                 320

Asn Val Lys Ala Tyr Leu Phe Asn Asp Tyr Trp Glu Asp Ile Gly Thr
                325                 330                 335

Ile Lys Ser Phe Phe Glu Ala Asn Leu Ala Leu Ala Glu Gln Pro Ser
                340                 345                 350

Lys Phe Ser Phe Tyr Asp Ala Ser Lys Pro Met Tyr Thr Ser Arg Arg
                355                 360                 365

Asn Leu Pro Pro Ser Met Ile Ser Gly Ser Lys Ile Thr Asp Ser Ile
                370                 375                 380

Ile Ser His Gly Cys Phe Leu Asp Lys Cys Arg Val Glu His Ser Val
385                 390                 395                 400

Val Gly Ile Arg Ser Arg Ile Gly Ser Asn Val His Leu Lys Asp Thr
                405                 410                 415

Val Met Leu Gly Ala Asp Phe Tyr Glu Thr Asp Ala Glu Arg Gly Asp
                420                 425                 430

Gln Leu Ala Glu Gly Lys Val Pro Ile Gly Ile Gly Glu Asn Thr Ser
                435                 440                 445

Ile Gln Asn Cys Ile Ile Asp Lys Asn Ala Arg Ile Gly Lys Asn Val
                450                 455                 460

Thr Ile Ala Asn Thr Glu Gly Val Gln Glu Ser Asp Arg Thr Ser Glu
465                 470                 475                 480

Gly Phe His Ile Arg Ser Gly Ile Thr Val Val Leu Lys Asn Ser Val
                485                 490                 495

Ile Ala Asp Gly Leu Val Ile
                500
```

<210> SEQ ID NO 45
<211> LENGTH: 517
<212> TYPE: PRT
<213> ORGANISM: Sorghum bicolor

<400> SEQUENCE: 45

```
Met Gln Phe Ser Leu Ala Ser Asp Ala Asn Ser Gly Pro His Pro Ile
1               5                   10                  15

Arg Arg Ser Cys Glu Gly Gly Ile Asp Arg Leu Glu Arg Leu Ser
            20                  25                  30

Ile Gly Gly Ser Lys Gln Glu Lys Ala Leu Arg Asn Arg Cys Phe Gly
        35                  40                  45

Gly Arg Val Ala Ala Thr Thr Gln Cys Ile Leu Thr Ser Asp Ala Cys
    50                  55                  60

Pro Glu Thr Leu His Phe Gln Thr Gln Ser Ser Arg Lys Ser Tyr Ala
65                  70                  75                  80

Asp Ala Asn His Val Ser Ala Ile Ile Leu Gly Gly Thr Gly Ser
                85                  90                  95

Gln Leu Phe Pro Leu Thr Ser Thr Arg Ala Thr Pro Ala Val Pro Val
            100                 105                 110

Gly Gly Cys Tyr Arg Leu Ile Asp Ile Pro Met Ser Asn Cys Phe Asn
        115                 120                 125

Ser Gly Ile Asn Lys Ile Phe Val Met Thr Gln Phe Asn Ser Thr Ser
    130                 135                 140

Leu Asn Arg His Ile His Arg Thr Tyr Leu Gly Gly Glu Ile Asn Phe
145                 150                 155                 160

Ala Asp Gly Ser Val Gln Val Leu Ala Asp Thr Gln Met Pro Glu Glu
                165                 170                 175

Pro Asp Gly Trp Phe Gln Gly Thr Ala Asp Ser Val Arg Lys Phe Ile
            180                 185                 190

Trp Val Leu Glu Asp Tyr Tyr Asn His Lys Ser Ile Glu His Ile Val
        195                 200                 205

Ile Leu Ser Gly Asp Gln Leu Tyr Gln Met Asn Tyr Met Glu Leu Val
    210                 215                 220

Gln Lys His Val Glu Asp Asn Ala Asp Ile Thr Val Ser Cys Ala Pro
225                 230                 235                 240

Val Asp Glu Ser Arg Ala Ser Asn Asn Gly Leu Val Lys Cys Asp His
                245                 250                 255

Thr Gly Arg Val Leu Gln Phe Phe Glu Lys Pro Lys Gly Ala Asp Leu
            260                 265                 270

Asn Ser Met Arg Val Asp Thr Asn Phe Leu Ser Tyr Ala Ile Gly Asp
        275                 280                 285

Ala Gln Lys Tyr Gln Tyr Ile Ala Ser Met Gly Ile Tyr Val Phe Lys
    290                 295                 300

Lys Asp Ala Leu Leu Asp Leu Leu Lys Ser Lys Tyr Thr Gln Leu His
305                 310                 315                 320

Asp Phe Gly Ser Glu Ile Leu Pro Arg Ala Val Leu Glu His Asn Val
                325                 330                 335

Gln Thr Cys Ile Phe Met Gly Tyr Trp Glu Asp Val Gly Thr Ile Lys
            340                 345                 350

Ser Phe Phe Asp Ala Asn Leu Ala Leu Thr Glu Gln Pro Ser Lys Phe
        355                 360                 365

Asp Phe Tyr Asp Pro Lys Thr Pro Phe Phe Thr Ala Pro Arg Tyr Leu
```

```
            370                 375                 380
Pro Pro Thr Gln Leu Asp Lys Cys Lys Ile Lys Asp Ala Ser Ile Ser
385                 390                 395                 400

Asp Gly Cys Leu Leu Arg Glu Cys Ser Ile Glu His Ser Val Ile Gly
                405                 410                 415

Val Cys Ser Arg Val Ser Tyr Gly Cys Glu Leu Lys Asp Cys Val Met
            420                 425                 430

Met Gly Ala Asp Ile Tyr Glu Thr Glu Glu Ala Ser Lys Leu Leu
        435                 440                 445

Leu Ala Gly Glu Val Pro Val Gly Ile Gly Gly Asn Thr Lys Ile Arg
    450                 455                 460

Asn Cys Ile Ile Asp Ile Asn Ala Arg Ile Gly Lys Asn Val Val Ile
465                 470                 475                 480

Thr Asn Ser Lys Gly Ile Gln Glu Ala Asp His Pro Glu Glu Gly Tyr
                485                 490                 495

Tyr Ile Lys Ser Gly Ile Val Val Ile Leu Lys Asn Ala Thr Ile Lys
            500                 505                 510

Asp Gly Ser Val Ile
        515

<210> SEQ ID NO 46
<211> LENGTH: 518
<212> TYPE: PRT
<213> ORGANISM: Oryza sativa

<400> SEQUENCE: 46

Met Gln Phe Met Met Pro Leu Asp Thr Asn Ala Cys Ala Gln Pro Met
1               5                   10                  15

Arg Arg Ala Gly Glu Gly Ala Gly Thr Glu Arg Leu Met Glu Arg Leu
            20                  25                  30

Asn Ile Gly Gly Met Thr Gln Glu Lys Ala Leu Arg Lys Arg Cys Phe
        35                  40                  45

Gly Asp Gly Val Thr Gly Thr Ala Arg Cys Val Phe Thr Ser Asp Ala
    50                  55                  60

Asp Arg Asp Thr Pro His Leu Arg Thr Gln Ser Ser Arg Lys Asn Tyr
65                  70                  75                  80

Ala Asp Ala Ser His Val Ser Ala Val Ile Leu Gly Gly Thr Gly
            85                  90                  95

Val Gln Leu Phe Pro Leu Thr Ser Thr Arg Ala Thr Pro Ala Val Pro
            100                 105                 110

Val Gly Gly Cys Tyr Arg Leu Ile Asp Ile Pro Met Ser Asn Cys Phe
            115                 120                 125

Asn Ser Gly Ile Asn Lys Ile Phe Val Met Thr Gln Phe Asn Ser Ala
130                 135                 140

Ser Leu Asn Arg His Ile His His Thr Tyr Leu Gly Gly Ile Asn
145                 150                 155                 160

Phe Thr Asp Gly Ser Val Gln Val Leu Ala Ala Thr Gln Met Pro Asp
                165                 170                 175

Glu Pro Ala Gly Trp Phe Gln Gly Thr Ala Asp Ala Ile Arg Lys Phe
            180                 185                 190

Met Trp Ile Leu Glu Asp His Tyr Asn Gln Asn Asn Ile Glu His Val
        195                 200                 205

Val Ile Leu Cys Gly Asp Gln Leu Tyr Arg Met Asn Tyr Met Glu Leu
    210                 215                 220
```

Val Gln Lys His Val Asp Asp Asn Ala Asp Ile Thr Ile Ser Cys Ala
225                 230                 235                 240

Pro Ile Asp Gly Ser Arg Ala Ser Asp Tyr Gly Leu Val Lys Phe Asp
            245                 250                 255

Asp Ser Gly Arg Val Ile Gln Phe Leu Glu Lys Pro Glu Gly Ala Asp
            260                 265                 270

Leu Glu Ser Met Lys Val Asp Thr Ser Phe Leu Ser Tyr Ala Ile Asp
            275                 280                 285

Asp Lys Gln Lys Tyr Pro Tyr Ile Ala Ser Met Gly Ile Tyr Val Leu
            290                 295                 300

Lys Lys Asp Val Leu Leu Asp Ile Leu Lys Ser Lys Tyr Ala His Leu
305                 310                 315                 320

Gln Asp Phe Gly Ser Glu Ile Leu Pro Arg Ala Val Leu Glu His Asn
            325                 330                 335

Val Lys Ala Cys Val Phe Thr Glu Tyr Trp Glu Asp Ile Gly Thr Ile
            340                 345                 350

Lys Ser Phe Phe Asp Ala Asn Leu Ala Leu Thr Glu Gln Pro Pro Lys
            355                 360                 365

Phe Glu Phe Tyr Asp Pro Lys Thr Pro Phe Phe Thr Ser Pro Arg Tyr
            370                 375                 380

Leu Pro Pro Ala Arg Leu Glu Lys Cys Lys Ile Lys Asp Ala Ile Ile
385                 390                 395                 400

Ser Asp Gly Cys Ser Phe Ser Glu Cys Thr Ile Glu His Ser Val Ile
            405                 410                 415

Gly Ile Ser Ser Arg Val Ser Ile Gly Cys Glu Leu Lys Asp Thr Met
            420                 425                 430

Met Met Gly Ala Asp Gln Tyr Glu Thr Glu Glu Thr Ser Lys Leu
            435                 440                 445

Leu Phe Glu Gly Lys Val Pro Ile Gly Ile Gly Glu Asn Thr Lys Ile
450                 455                 460

Arg Asn Cys Ile Ile Asp Met Asn Ala Arg Ile Gly Arg Asn Val Ile
465                 470                 475                 480

Ile Ala Asn Thr Gln Gly Val Gln Glu Ser Asp His Pro Glu Glu Gly
            485                 490                 495

Tyr Tyr Ile Arg Ser Gly Ile Val Val Ile Leu Lys Asn Ala Thr Ile
            500                 505                 510

Lys Asp Gly Thr Val Ile
            515

<210> SEQ ID NO 47
<211> LENGTH: 518
<212> TYPE: PRT
<213> ORGANISM: Oryza sativa

<400> SEQUENCE: 47

Met Glu Phe Met Met Pro Leu Asp Thr Asn Ala Cys Ala Gln Pro Met
1               5                   10                  15

Arg Arg Ala Gly Glu Gly Ala Gly Thr Glu Arg Leu Met Glu Arg Leu
            20                  25                  30

Asn Ile Gly Gly Met Thr Gln Glu Lys Ala Leu Arg Lys Arg Cys Phe
            35                  40                  45

Gly Asp Gly Val Thr Gly Thr Ala Arg Cys Val Phe Thr Ser Asp Ala
        50                  55                  60

Asp Arg Asp Thr Pro His Leu Arg Thr Gln Ser Ser Arg Lys Asn Tyr
65                  70                  75                  80

```
Ala Asp Ala Ser His Val Ser Ala Val Ile Leu Gly Gly Thr Gly
                85                  90                  95

Val Gln Leu Phe Pro Leu Thr Ser Thr Arg Ala Thr Pro Ala Val Pro
                100                 105                 110

Val Gly Gly Cys Tyr Arg Leu Ile Asp Ile Pro Met Ser Asn Cys Phe
            115                 120                 125

Asn Ser Gly Ile Asn Lys Ile Phe Val Met Thr Gln Phe Asn Ser Ala
130                 135                 140

Ser Leu Asn Arg His Ile His His Thr Tyr Leu Gly Gly Ile Asn
145                 150                 155                 160

Phe Thr Asp Gly Ser Val Gln Val Leu Ala Ala Thr Gln Met Pro Asp
                165                 170                 175

Glu Pro Ala Gly Trp Phe Gln Gly Thr Ala Asp Ala Ile Arg Lys Phe
                180                 185                 190

Met Trp Ile Leu Glu Asp His Tyr Asn Gln Asn Asn Ile Glu His Val
                195                 200                 205

Val Ile Leu Cys Gly Asp Gln Leu Tyr Arg Met Asn Tyr Met Glu Leu
            210                 215                 220

Val Gln Lys His Val Asp Asp Asn Ala Asp Ile Thr Ile Ser Cys Ala
225                 230                 235                 240

Pro Ile Asp Gly Ser Arg Ala Ser Asp Tyr Gly Leu Val Lys Phe Asp
                245                 250                 255

Asp Ser Gly Arg Val Ile Gln Phe Leu Glu Lys Pro Glu Gly Ala Asp
                260                 265                 270

Leu Glu Ser Met Lys Val Asp Thr Ser Phe Leu Ser Tyr Ala Ile Asp
                275                 280                 285

Asp Lys Gln Lys Tyr Pro Tyr Ile Ala Ser Met Gly Ile Tyr Val Leu
                290                 295                 300

Lys Lys Asp Val Leu Leu Asp Ile Leu Lys Ser Lys Tyr Ala His Leu
305                 310                 315                 320

Gln Asp Phe Gly Ser Glu Ile Leu Pro Arg Ala Val Leu Glu His Asn
                325                 330                 335

Val Lys Ala Cys Val Phe Thr Glu Tyr Trp Glu Asp Ile Gly Thr Ile
                340                 345                 350

Lys Ser Phe Phe Asp Ala Asn Leu Ala Leu Thr Glu Gln Pro Pro Lys
                355                 360                 365

Phe Glu Phe Tyr Asp Pro Lys Thr Pro Phe Phe Thr Ser Pro Arg Tyr
370                 375                 380

Leu Pro Pro Ala Arg Leu Glu Lys Cys Lys Ile Lys Asp Ala Ile Ile
385                 390                 395                 400

Ser Asp Gly Cys Ser Phe Ser Glu Cys Thr Ile Glu His Ser Val Ile
                405                 410                 415

Gly Ile Ser Ser Arg Val Ser Ile Gly Cys Glu Leu Lys Asp Thr Met
                420                 425                 430

Met Met Gly Ala Asp Gln Tyr Glu Thr Glu Glu Thr Ser Lys Leu
                435                 440                 445

Leu Phe Glu Gly Lys Val Pro Ile Gly Ile Gly Glu Asn Thr Lys Ile
450                 455                 460

Arg Asn Cys Ile Ile Asp Met Asn Ala Arg Ile Gly Arg Asn Val Ile
465                 470                 475                 480

Ile Ala Asn Thr Gln Gly Val Gln Glu Ser Asp His Pro Glu Glu Gly
                485                 490                 495
```

```
Tyr Tyr Ile Arg Ser Gly Ile Val Val Ile Leu Lys Asn Ala Thr Ile
            500                 505                 510

Lys His Gly Pro Ile Ile
        515

<210> SEQ ID NO 48
<211> LENGTH: 514
<212> TYPE: PRT
<213> ORGANISM: Oryza sativa

<400> SEQUENCE: 48

Met Gln Phe Met Met Pro Leu Asp Thr Asn Ala Cys Ala Gln Pro Met
1               5                   10                  15

Arg Arg Ala Gly Glu Gly Ala Gly Thr Glu Arg Leu Met Glu Arg Leu
            20                  25                  30

Asn Ile Gly Gly Met Thr Gln Glu Lys Ala Leu Arg Lys Arg Cys Phe
        35                  40                  45

Gly Asp Gly Val Thr Gly Thr Ala Arg Arg Val Phe Thr Ser Asp Ala
50                  55                  60

Asp Arg Asp Thr Pro His Leu Arg Thr Gln Phe Ser Arg Lys Asn Tyr
65                  70                  75                  80

Ala Asp Ala Ser His Val Ser Ala Val Ile Leu Gly Gly Gly Thr Gly
                85                  90                  95

Val Gln Leu Phe Pro Leu Thr Arg Thr Arg Ala Thr Pro Ala Val Pro
            100                 105                 110

Val Gly Gly Cys Tyr Arg Leu Ile Asp Ile Pro Met Ser Asn Cys Phe
        115                 120                 125

Asn Ser Gly Ile Asn Lys Asn Ile Phe Val Met Thr Gln Phe Asn Leu
130                 135                 140

Thr Ser Leu Asn Arg Asn Ile His His Thr Tyr Leu Val Gly Gly Ile
145                 150                 155                 160

Asn Leu Thr Asp Gly Ser Val Gln Val Leu Ala Ala Thr Gln Met Pro
                165                 170                 175

Asp Glu Pro Ala Gly Trp Phe Gln Gly Thr Ala Asp Ala Ile Arg Lys
            180                 185                 190

Phe Met Trp Ile Leu Glu Asp His Ile His Lys Ser Ile Asp Asn Ile
        195                 200                 205

Val Ile Leu Cys Gly Asp Gln Leu Tyr Arg Met Asn Tyr Met Glu Leu
210                 215                 220

Val Gln Lys His Val Asp Thr Asn Ala Asp Ile Thr Ile Ser Cys Ala
225                 230                 235                 240

Pro Ile Asp Gly Ser Arg Ala Ser Asp Tyr Gly Leu Val Lys Phe Asp
                245                 250                 255

His Ser Gly Arg Val Ile Gln Phe Leu Glu Lys Pro Glu Gly Ala Asp
            260                 265                 270

Leu Glu Ser Met Val Asp Thr Ser Phe Leu Ser Tyr Ala Ile Asp Asp
        275                 280                 285

Lys Gln Lys Tyr Pro Tyr Ile Ala Ser Met Gly Ile Tyr Val Leu Lys
290                 295                 300

Lys Asp Val Leu Leu Asp Ile Leu Lys Ser Lys Tyr Ala His Leu Gln
305                 310                 315                 320

Asp Phe Gly Ser Glu Ile Leu Pro Arg Ala Leu Leu Glu His Asn Val
                325                 330                 335

Lys Val Ala Cys Val Phe Thr Glu Tyr Trp Glu Asp Ile Gly Thr Ile
            340                 345                 350
```

```
Lys Ser Phe Phe Asp Ala Asn Leu Ala Leu Thr Glu Gln Pro Pro Lys
            355                 360                 365

Phe Glu Phe Tyr Asp Pro Lys Thr Pro Phe Phe Thr Ser Pro Arg Tyr
370                 375                 380

Leu Pro Pro Ala Arg Leu Asp Lys Cys Lys Cys Lys Ile Lys Asp Ala
385                 390                 395                 400

Ile Ile Ser Asp Gly Cys Ser Phe Ser Glu Cys Thr Ile Glu His Ser
                405                 410                 415

Val Ile Gly Ile Ser Ser Arg Val Ser Ser Gly Cys Glu Leu Lys Ile
            420                 425                 430

Tyr Glu Thr Glu Glu Thr Ser Lys Leu Leu Phe Glu Gly Lys Val
        435                 440                 445

Pro Ile Gly Ile Gly Gln Asn Thr Lys Ile Arg Asn Cys Ile Ile Asp
            450                 455                 460

Met Asn Ala Arg Ile Gly Arg Asn Ala Ile Ile Ala Asn Thr Gln Gly
465                 470                 475                 480

Val Gln Glu Ser Asp His Pro Glu Glu Gly Tyr Ile Arg Ser Gly Ile
                485                 490                 495

Val Val Ile Leu Lys Asn Ala Thr Asn Ala Thr Ile Lys His Gly Thr
            500                 505                 510

Val Ile
```

<210> SEQ ID NO 49
<211> LENGTH: 519
<212> TYPE: PRT
<213> ORGANISM: Oryza sativa

<400> SEQUENCE: 49

```
Met Gln Phe Ser Ser Val Phe Pro Leu Glu Gly Lys Ala Cys Val Ser
1               5                   10                  15

Pro Ile Arg Arg Gly Gly Glu Gly Ser Ala Ser Asp Arg Leu Lys Ile
            20                  25                  30

Gly Asp Ser Ser Ser Ile Lys His Asp Arg Ala Val Arg Arg Met Cys
        35                  40                  45

Leu Gly Tyr Arg Gly Thr Lys Asn Gly Ala Gln Cys Val Leu Thr Ser
50                  55                  60

Asp Ala Gly Pro Asp Thr Leu His Val Arg Thr Ser Phe Arg Arg Asn
65                  70                  75                  80

Phe Ala Asp Pro Asn Glu Val Ala Ala Val Ile Leu Gly Gly Gly Thr
                85                  90                  95

Gly Thr Gln Leu Phe Pro Leu Thr Ser Arg Ala Thr Pro Ala Val
            100                 105                 110

Pro Ile Gly Gly Cys Tyr Arg Leu Ile Asp Ile Pro Met Ser Asn Cys
        115                 120                 125

Phe Asn Ser Gly Ile Asn Lys Ile Phe Ile Met Thr Gln Phe Asn Ser
130                 135                 140

Ala Ser Leu Asn Arg His Ile His Arg Thr Tyr Leu Gly Gly Gly Ile
145                 150                 155                 160

Asn Phe Thr Asp Gly Ser Val Glu Val Leu Ala Ala Thr Gln Met Pro
                165                 170                 175

Gly Glu Ala Ala Gly Trp Phe Gln Gly Thr Ala Asp Ala Val Arg Lys
            180                 185                 190

Phe Ile Trp Val Leu Glu Asp Tyr Tyr Lys His Lys Ala Ile Glu His
        195                 200                 205
```

Ile Leu Ile Leu Ser Gly Asp Gln Leu Tyr Arg Met Asp Tyr Met Glu
            210                 215                 220

Leu Val Gln Lys His Val Asp Asp Asn Ala Asp Ile Thr Leu Ser Cys
225                 230                 235                 240

Ala Pro Val Gly Glu Ser Arg Ala Ser Asp Tyr Gly Leu Val Lys Phe
            245                 250                 255

Asp Ser Ser Gly Arg Val Ile Gln Phe Ser Glu Lys Pro Lys Gly Thr
            260                 265                 270

Asp Leu Glu Ala Met Lys Val Asp Thr Ser Phe Leu Asn Phe Ala Ile
            275                 280                 285

Asp Asp Pro Thr Lys Phe Pro Tyr Ile Ala Ser Met Gly Val Tyr Val
            290                 295                 300

Phe Lys Arg Asp Val Leu Leu Asn Leu Leu Lys Ser Arg Tyr Ala Glu
305                 310                 315                 320

Leu His Asp Phe Gly Ser Glu Ile Leu Pro Arg Ala Leu His Glu His
            325                 330                 335

Asn Val Gln Ala Tyr Val Phe Ala Asp Tyr Trp Glu Asp Ile Gly Thr
            340                 345                 350

Ile Arg Ser Phe Phe Asp Ala Asn Met Ala Leu Cys Glu Gln Pro Pro
            355                 360                 365

Lys Phe Glu Phe Tyr Asp Pro Lys Thr Pro Phe Phe Thr Ser Pro Arg
            370                 375                 380

Tyr Leu Pro Pro Thr Lys Ser Asp Lys Cys Arg Ile Lys Asp Ala Ile
385                 390                 395                 400

Ile Ser His Gly Cys Leu Leu Arg Glu Cys Thr Ile Gly His Ser Ile
            405                 410                 415

Val Gly Val Arg Ser Arg Leu Asn Ser Ala Cys Glu Leu Lys Asn Thr
            420                 425                 430

Met Met Met Gly Ala Asp Leu Tyr Glu Thr Glu Asp Glu Ile Ser Arg
            435                 440                 445

Leu Leu Ser Glu Gly Lys Val Pro Ile Gly Val Gly Glu Asn Thr Lys
            450                 455                 460

Ile Asn Asn Cys Ile Ile Asp Met Asn Ala Arg Val Gly Arg Asn Val
465                 470                 475                 480

Val Ile Thr Asn Ser Glu Gly Val Gln Glu Ser Asp Arg Pro Glu Glu
            485                 490                 495

Gly Tyr Tyr Ile Arg Ser Gly Ile Val Val Ile Leu Lys Asn Ala Thr
            500                 505                 510

Ile Lys Asp Gly Lys Val Ile
            515

<210> SEQ ID NO 50
<211> LENGTH: 522
<212> TYPE: PRT
<213> ORGANISM: Triticum aestivum

<400> SEQUENCE: 50

Met Ser Ser Met Gln Phe Ser Ser Val Leu Pro Leu Glu Gly Lys Ala
1               5                   10                  15

Cys Ile Ser Pro Val Arg Arg Glu Gly Ser Ala Ser Glu Arg Leu Lys
            20                  25                  30

Val Gly Asp Ser Ser Ser Ile Arg His Glu Arg Ala Ser Arg Arg Met
            35                  40                  45

Cys Asn Gly Gly Arg Gly Pro Ala Ala Thr Gly Ala Gln Cys Val Leu

```
            50                  55                  60
Thr Ser Asp Ala Ser Pro Ala Asp Thr Leu Val Leu Arg Thr Ser Phe
 65                  70                  75                  80

Arg Arg Asn Tyr Ala Asp Pro Asn Glu Val Ala Val Ile Leu Gly
                 85                  90                  95

Gly Gly Thr Gly Thr Gln Leu Phe Pro Leu Thr Ser Thr Arg Ala Thr
                100                 105                 110

Pro Ala Val Pro Ile Gly Gly Cys Tyr Arg Leu Ile Asp Ile Pro Met
                115                 120                 125

Ser Asn Cys Phe Asn Ser Gly Ile Asn Lys Ile Phe Val Met Thr Gln
130                 135                 140

Phe Asn Ser Ala Ser Leu Asn Arg His Ile His Arg Thr Tyr Leu Gly
145                 150                 155                 160

Gly Gly Ile Asn Phe Thr Asp Gly Ser Val Glu Val Leu Ala Ala Thr
                165                 170                 175

Gln Met Pro Gly Glu Ala Ala Gly Trp Phe Arg Gly Thr Ala Asp Ala
                180                 185                 190

Val Arg Lys Phe Ile Trp Val Leu Glu Asp Tyr Tyr Lys Asn Lys Ser
                195                 200                 205

Ile Glu His Ile Leu Ile Leu Ser Gly Asp Gln Leu Tyr Arg Met Asp
210                 215                 220

Tyr Met Glu Leu Val Gln Lys His Val Asp Asp Asn Ala Asp Ile Thr
225                 230                 235                 240

Leu Ser Cys Ala Pro Val Gly Glu Ser Arg Ala Ser Glu Tyr Gly Leu
                245                 250                 255

Val Lys Phe Asp Ser Ser Gly Arg Val Val Gln Phe Ser Glu Lys Pro
                260                 265                 270

Lys Gly Asp Asp Leu Glu Ala Met Lys Val Asp Thr Ser Phe Leu Asn
                275                 280                 285

Phe Ala Ile Asp Asp Pro Ala Lys Tyr Pro Tyr Ile Ala Ser Met Gly
290                 295                 300

Val Tyr Val Phe Lys Arg Asp Val Leu Leu Asn Leu Leu Lys Ser Arg
305                 310                 315                 320

Tyr Ala Glu Leu His Asp Phe Gly Ser Glu Ile Leu Pro Arg Ala Leu
                325                 330                 335

His Asp His Asn Val Gln Ala Tyr Val Phe Thr Asp Tyr Trp Glu Asp
                340                 345                 350

Ile Gly Thr Ile Arg Ser Phe Phe Asp Ala Asn Met Ala Leu Cys Glu
                355                 360                 365

Gln Pro Pro Lys Phe Glu Phe Tyr Asp Pro Lys Thr Pro Phe Phe Thr
370                 375                 380

Ser Pro Arg Tyr Leu Pro Pro Thr Lys Ser Asp Lys Cys Arg Ile Lys
385                 390                 395                 400

Glu Ala Ile Ile Ser His Gly Cys Phe Leu Arg Glu Cys Lys Ile Glu
                405                 410                 415

His Ser Ile Ile Gly Val Arg Ser Arg Leu Asn Ser Gly Ser Glu Leu
                420                 425                 430

Lys Asn Ala Met Met Met Gly Ala Asp Ser Tyr Glu Thr Glu Asp Glu
                435                 440                 445

Ile Ser Arg Leu Met Ser Glu Gly Lys Val Pro Ile Gly Val Gly Glu
450                 455                 460

Asn Thr Lys Ile Ser Asn Cys Ile Ile Asp Met Asn Ala Arg Ile Gly
465                 470                 475                 480
```

```
Arg Asp Val Val Ile Ser Asn Lys Glu Gly Val Gln Glu Ala Asp Arg
            485                 490                 495

Pro Glu Glu Gly Tyr Tyr Ile Arg Ser Gly Ile Val Val Ile Gln Lys
            500                 505                 510

Asn Ala Thr Ile Lys Asp Gly Thr Val Val
            515                 520

<210> SEQ ID NO 51
<211> LENGTH: 516
<212> TYPE: PRT
<213> ORGANISM: Lycopersicon esculentum

<400> SEQUENCE: 51

Met Ser Val Ala Thr Asp Val Arg Phe Ala Leu Leu Arg Asn Asn Pro
1               5                   10                  15

Ala Ala Leu Thr Gly Thr Asn Leu Lys Ile Val Lys Phe Cys Asn Gly
            20                  25                  30

Glu Leu Met Gly Lys Lys Leu Lys Tyr Thr Lys Phe Gln Leu Arg Ser
        35                  40                  45

Asn Val Val Lys Pro His Ile Cys Met Ser Leu Thr Thr Asp Ile Ala
    50                  55                  60

Gly Glu Ala Lys Leu Lys Asp Leu Glu Ala Lys Lys Glu Asp Ala Arg
65                  70                  75                  80

Thr Val Val Ala Ile Ile Leu Gly Gly Gly Gly Thr Arg Leu Phe
                85                  90                  95

Pro Leu Thr Lys Arg Arg Ala Lys Pro Ala Val Pro Ile Gly Gly Ala
            100                 105                 110

Tyr Arg Leu Ile Asp Val Pro Met Ser Asn Cys Ile Asn Ser Gly Ile
        115                 120                 125

Asn Lys Val Tyr Ile Leu Thr Gln Phe Asn Ser Ala Ser Leu Asn Arg
    130                 135                 140

His Ile Ala Arg Ala Tyr Asn Phe Gly Asn Gly Val Thr Phe Gly Asp
145                 150                 155                 160

Gly Tyr Val Glu Val Leu Ala Ala Thr Gln Thr Pro Gly Glu Leu Gly
                165                 170                 175

Lys Arg Trp Phe Gln Gly Thr Ala Asp Ala Val Arg Gln Phe His Trp
            180                 185                 190

Leu Phe Glu Asp Ala Arg Ser Lys Asp Ile Glu Asp Val Leu Ile Leu
        195                 200                 205

Ser Gly Asp His Leu Tyr Arg Met Asp Tyr Leu His Phe Val Gln Ser
    210                 215                 220

His Arg Gln Ser Gly Ala Asp Ile Thr Ile Ser Ser Leu Pro Ile Asp
225                 230                 235                 240

Asp Ser Arg Ala Ser Asp Phe Gly Leu Met Lys Ile Asp Asp Thr Gly
                245                 250                 255

Arg Val Met Ser Phe Ser Glu Lys Pro Lys Gly Asp Asp Leu Lys Ala
            260                 265                 270

Met Ala Val Asp Thr Thr Val Leu Gly Leu Ser Pro Glu Glu Ala Lys
        275                 280                 285

Glu Lys Pro Tyr Ile Ala Ser Met Gly Val Tyr Val Phe Lys Lys Asp
    290                 295                 300

Ile Leu Leu Asn Leu Leu Arg Trp Arg Phe Pro Thr Val Asn Asp Phe
305                 310                 315                 320

Gly Ser Glu Ile Ile Pro Ala Ser Thr Lys Glu Phe Cys Val Lys Ala
```

```
                        325                 330                 335
Tyr Tyr Leu Phe Asn Asp Tyr Trp Glu Asp Ile Gly Thr Ile Arg Ser
            340                 345                 350
Phe Phe Glu Ala Asn Leu Ala Leu Thr Glu His Pro Pro Arg Phe Ser
        355                 360                 365
Phe Tyr Asp Ala Thr Lys Pro Ile Tyr Thr Ser Arg Arg Asn Leu Pro
    370                 375                 380
Pro Ser Ala Ile Asp Asn Ser Lys Ile Val Asp Ser Ile Val Ser His
385                 390                 395                 400
Gly Ser Phe Leu Thr Asn Cys Phe Val Glu His Ser Val Val Gly Ile
                405                 410                 415
Arg Ser Arg Ile Gly Thr Asn Val His Leu Lys Asp Thr Val Met Leu
            420                 425                 430
Gly Ala Asp Tyr Tyr Glu Thr Asp Ala Glu Ile Ala Ser Gln Leu Ala
        435                 440                 445
Glu Gly Lys Val Pro Leu Gly Ile Gly Glu Asn Thr Arg Ile Lys Glu
    450                 455                 460
Cys Ile Ile Asp Lys Asn Ala Arg Ile Gly Lys Asn Val Val Ile Ala
465                 470                 475                 480
Asn Ser Glu Gly Val Gln Glu Ala Asp Arg Ser Ser Glu Gly Phe Tyr
                485                 490                 495
Ile Arg Ser Gly Ile Thr Val Ile Leu Lys Asn Ser Thr Ile Pro Asp
            500                 505                 510
Gly Thr Val Ile
        515

<210> SEQ ID NO 52
<211> LENGTH: 524
<212> TYPE: PRT
<213> ORGANISM: Lycopersicon esculentum

<400> SEQUENCE: 52

Met Asp Thr Cys Cys Ala Ala Met Lys Ser Thr Val His Leu Gly Arg
1               5                   10                  15
Val Ser Thr Gly Gly Phe Asn Asn Gly Glu Lys Glu Ile Phe Gly Glu
            20                  25                  30
Lys Ile Arg Gly Ser Leu Asn Asn Asn Leu Arg Ile Asn Gln Leu Ser
        35                  40                  45
Lys Ser Leu Lys Leu Glu Lys Lys Ile Lys Phe Gly Glu Ala Tyr Ser
    50                  55                  60
Val Ile Thr Ile Glu Asn Asp Thr Glu Thr Val Phe Val Asp Met Pro
65                  70                  75                  80
Arg Leu Glu Arg Arg Ala Asn Pro Lys Asp Val Ala Ala Val Ile
                85                  90                  95
Leu Gly Gly Gly Glu Gly Thr Lys Leu Phe Pro Leu Thr Ser Arg Thr
            100                 105                 110
Ala Thr Pro Ala Val Pro Val Gly Gly Cys Tyr Arg Leu Ile Asp Ile
        115                 120                 125
Pro Met Ser Asn Cys Ile Asn Ser Ala Ile Asn Lys Ile Phe Val Leu
    130                 135                 140
Thr Gln Tyr Asn Ser Ala Ala Leu Asn Arg His Ile Ala Arg Thr Tyr
145                 150                 155                 160
Phe Gly Asn Gly Val Ser Phe Gly Asp Gly Phe Val Glu Val Leu Ala
                165                 170                 175
```

```
Ala Thr Gln Thr Pro Gly Glu Ala Gly Lys Lys Trp Phe Gln Gly Thr
                180                 185                 190

Ala Asp Ala Val Arg Lys Phe Ile Trp Val Phe Glu Asp Ala Lys Asn
            195                 200                 205

Lys Asn Ile Glu Asn Ile Leu Val Leu Ser Gly Asp His Leu Tyr Arg
210                 215                 220

Met Asp Tyr Met Glu Leu Val Gln Asn His Ile Asp Arg Asn Ala Asp
225                 230                 235                 240

Ile Thr Leu Ser Cys Ala Pro Ala Glu Asp Ser Arg Ala Ser Asp Phe
                245                 250                 255

Gly Leu Val Lys Ile Asp Ser Arg Gly Arg Val Val Gln Phe Ala Glu
            260                 265                 270

Lys Pro Lys Gly Phe Asp Leu Lys Ala Met Gln Val Asp Thr Thr Leu
        275                 280                 285

Val Gly Leu Ser Pro Gln Asp Ala Lys Lys Ser Pro Tyr Ile Ala Ser
    290                 295                 300

Met Gly Val Tyr Val Phe Lys Thr Asp Val Leu Leu Lys Leu Leu Lys
305                 310                 315                 320

Trp Ser Tyr Pro Thr Ser Asn Asp Phe Gly Ser Glu Ile Ile Pro Ala
                325                 330                 335

Ala Ile Asp Asp Tyr Asn Val Gln Ala Tyr Ile Phe Lys Asp Tyr Trp
            340                 345                 350

Glu Asp Ile Gly Thr Ile Lys Ser Phe Tyr Asn Ala Ser Leu Ala Leu
        355                 360                 365

Thr Gln Glu Phe Pro Gly Phe Gln Phe Tyr Asp Pro Lys Thr Pro Phe
    370                 375                 380

Tyr Thr Ser Pro Arg Phe Leu Pro Pro Thr Lys Ile Asp Asn Cys Lys
385                 390                 395                 400

Ile Lys Asp Ala Ile Ile Ser His Gly Cys Phe Leu Arg Asp Cys Thr
                405                 410                 415

Val Glu His Ser Ile Val Gly Glu Arg Ser Arg Leu Asp Cys Gly Val
            420                 425                 430

Glu Leu Lys Asp Thr Phe Met Met Gly Ala Asp Tyr Tyr Gln Thr Glu
        435                 440                 445

Ser Glu Ile Ala Ser Leu Leu Ala Glu Gly Lys Val Pro Ile Gly Ile
    450                 455                 460

Gly Glu Asn Thr Lys Ile Arg Lys Cys Ile Ile Asp Lys Asn Ala Lys
465                 470                 475                 480

Ile Gly Lys Asn Val Ser Ile Ile Asn Lys Asp Gly Val Gln Glu Ala
                485                 490                 495

Asp Arg Pro Glu Glu Gly Phe Tyr Ile Arg Ser Gly Ile Ile Ile Ile
            500                 505                 510

Ala Glu Lys Ala Thr Ile Arg Asp Gly Thr Val Ile
        515                 520

<210> SEQ ID NO 53
<211> LENGTH: 518
<212> TYPE: PRT
<213> ORGANISM: Lycopersicon esculentum

<400> SEQUENCE: 53

Met Asp Ala Leu Cys Ala Gly Thr Ala Gln Ser Val Ala Ile Cys Asn
1               5                   10                  15

Gln Glu Ser Thr Phe Trp Gly Gln Lys Ile Ser Gly Arg Arg Leu Ile
            20                  25                  30
```

```
Asn Lys Gly Phe Gly Val Arg Trp Cys Lys Ser Phe Thr Thr Gln Gln
     35                  40                  45
Arg Gly Arg Gly Val Thr Ser Ala Val Leu Thr Arg Asp Ile Asn Lys
     50                  55                  60
Glu Met Leu Pro Phe Glu Asn Ser Met Phe Glu Glu Gln Pro Thr Ala
65                   70                  75                  80
Asp Pro Lys Ala Val Ala Ser Val Ile Leu Gly Gly Val Gly Thr
                 85                  90                  95
Arg Leu Phe Pro Leu Thr Ser Arg Arg Ala Lys Pro Ala Val Pro Ile
                 100                 105                 110
Gly Gly Cys Tyr Arg Leu Ile Asp Val Pro Met Ser Asn Cys Ile Asn
                 115                 120                 125
Ser Gly Ile Arg Lys Ile Phe Ile Leu Thr Gln Phe Asn Ser Phe Ser
     130                 135                 140
Leu Asn Arg His Leu Ala Arg Thr Tyr Asn Phe Gly Asn Gly Val Gly
145                  150                 155                 160
Phe Gly Asp Gly Phe Val Glu Val Leu Ala Ala Thr Gln Thr Pro Gly
                 165                 170                 175
Asp Ala Gly Lys Met Trp Phe Gln Gly Thr Ala Asp Ala Val Arg Gln
                 180                 185                 190
Phe Ile Trp Val Phe Glu Asn Gln Lys Asn Lys Asn Val Glu His Ile
                 195                 200                 205
Ile Ile Leu Ser Gly Asp His Leu Tyr Arg Met Asn Tyr Met Asp Phe
210                  215                 220
Val Gln Lys His Ile Asp Ala Asn Ala Asp Ile Thr Val Ser Cys Val
225                  230                 235                 240
Pro Met Asp Asp Gly Arg Ala Ser Asp Phe Gly Leu Met Lys Ile Asp
                 245                 250                 255
Glu Thr Gly Arg Ile Ile Gln Phe Ala Glu Lys Pro Lys Gly Pro Ala
                 260                 265                 270
Leu Lys Val Met Gln Val Asp Thr Ser Ile Leu Gly Leu Ser Glu Gln
     275                 280                 285
Glu Ala Ser Asn Phe Pro Tyr Ile Ala Ser Met Gly Val Tyr Val Phe
     290                 295                 300
Lys Thr Asp Val Leu Leu Lys Leu Leu Lys Ser Ala Tyr Pro Ser Cys
305                  310                 315                 320
Asn Asp Phe Gly Ser Glu Ile Ile Pro Ser Ala Val Lys Asp His Asn
                 325                 330                 335
Val Gln Ala Tyr Leu Phe Asn Asp Tyr Trp Glu Asp Ile Gly Thr Val
                 340                 345                 350
Lys Ser Phe Phe Asp Ala Asn Leu Ala Leu Thr Lys Gln Pro Pro Lys
     355                 360                 365
Phe Asp Phe Asn Asp Pro Lys Thr Pro Phe Tyr Thr Ser Ala Arg Phe
     370                 375                 380
Leu Pro Pro Thr Lys Val Asp Lys Ser Arg Ile Val Asp Ala Ile Ile
385                  390                 395                 400
Ser His Gly Gly Phe Leu Arg Glu Cys Asn Ile Gln His Ser Ile Val
                 405                 410                 415
Gly Val Arg Ser Arg Leu Asp Tyr Gly Val Glu Phe Lys Asp Thr Met
                 420                 425                 430
Met Met Gly Ala Asp Tyr Tyr Gln Thr Glu Ser Glu Ile Ala Ser Leu
     435                 440                 445
```

Leu Ala Glu Gly Lys Val Pro Ile Gly Val Gly Pro Asn Thr Lys Ile
            450                 455                 460

Gln Lys Cys Ile Ile Asp Lys Asn Ala Lys Ile Gly Lys Asp Val Val
465                 470                 475                 480

Ile Leu Asn Lys Gln Gly Val Glu Glu Ala Asp Arg Ser Ala Glu Gly
                485                 490                 495

Phe Tyr Ile Arg Ser Gly Ile Thr Val Ile Met Lys Asn Ala Thr Ile
            500                 505                 510

Lys Asp Gly Thr Val Ile
            515

<210> SEQ ID NO 54
<211> LENGTH: 483
<212> TYPE: PRT
<213> ORGANISM: Solanum tuberosum

<400> SEQUENCE: 54

Met Gly Lys Lys Leu Lys Tyr Thr Lys Phe Gln Leu Arg Ser Asn Val
1               5                   10                  15

Val Lys Pro Asn Ile Cys Met Ser Leu Thr Thr Asp Ile Ala Gly Glu
            20                  25                  30

Ala Lys Leu Lys Asp Leu Glu Arg Gln Lys Lys Gly Asp Ala Arg Thr
        35                  40                  45

Val Val Ala Ile Ile Leu Gly Gly Gly Ala Gly Thr Arg Leu Phe Pro
50                  55                  60

Leu Thr Lys Arg Arg Ala Lys Pro Ala Val Pro Met Gly Gly Ala Tyr
65                  70                  75                  80

Arg Leu Ile Asp Val Pro Met Ser Asn Cys Ile Asn Ser Gly Ile Asn
                85                  90                  95

Lys Val Tyr Ile Leu Thr Gln Phe Asn Ser Ala Ser Leu Asn Arg His
            100                 105                 110

Ile Ala Arg Ala Tyr Asn Phe Gly Asn Gly Val Thr Phe Glu Ser Gly
        115                 120                 125

Tyr Val Glu Val Leu Ala Ala Thr Gln Thr Pro Gly Glu Leu Gly Lys
130                 135                 140

Arg Trp Phe Gln Gly Thr Ala His Ala Val Arg Gln Phe His Trp Leu
145                 150                 155                 160

Phe Glu Asp Ala Arg Ser Lys Asp Ile Glu Asp Val Leu Ile Leu Ser
                165                 170                 175

Gly Asp His Leu Tyr Arg Met Asp Tyr Leu His Phe Val Gln Ser His
            180                 185                 190

Arg Gln Ser Gly Ala Asp Ile Thr Ile Ser Ser Leu Pro Ile Asp Asp
        195                 200                 205

Ser Arg Ala Ser Asp Phe Gly Leu Met Lys Ile Asp Asp Thr Gly Arg
210                 215                 220

Val Met Ser Phe Ser Glu Lys Pro Lys Gly Asp Asp Leu Lys Ala Met
225                 230                 235                 240

Ala Val Asp Thr Thr Val Leu Gly Leu Ser Pro Glu Glu Ala Lys Glu
                245                 250                 255

Lys Pro Tyr Ile Ala Ser Ile Gly Lys Val Tyr Val Phe Lys Lys Asp
            260                 265                 270

Ile Leu Leu Asn Leu Leu Arg Trp Arg Phe Pro Thr Ala Asn Asp Phe
        275                 280                 285

Gly Ser Glu Ile Ile Pro Ala Ser Thr Lys Glu Phe Cys Val Lys Ala
290                 295                 300

```
Tyr Leu Phe Asn Asp Tyr Trp Glu Asp Ile Gly Thr Ile Arg Ser Phe
305                 310                 315                 320

Phe Arg Ala Asn Leu Ala Leu Thr Glu His Pro Pro Arg Phe Ser Phe
            325                 330                 335

Tyr Asp Ala Thr Lys Pro Ile Tyr Thr Ser Arg Arg Asn Leu Pro Pro
            340                 345                 350

Ser Ala Ile Asp Asn Ser Lys Ile Val Asp Ser Ile Val Ser His Gly
            355                 360                 365

Ile Phe Leu Thr Asn Cys Phe Val Glu His Ser Val Val Gly Ile Arg
370                 375                 380

Ser Arg Ile Gly Thr Asn Val His Leu Lys Asp Thr Val Met Leu Gly
385                 390                 395                 400

Ala Asp Tyr Tyr Glu Thr Asp Ala Glu Ile Arg Ser Gln Leu Ala Glu
                405                 410                 415

Gly Lys Val Pro Leu Gly Ile Gly Glu Asn Thr Arg Ile Lys Asp Cys
            420                 425                 430

Ile Ile Asp Lys Asn Ala Arg Ile Gly Lys Asn Val Val Ile Ala Asn
            435                 440                 445

Ser Glu Gly Val Gln Glu Ala Asp Arg Ser Ser Glu Gly Phe Tyr Met
450                 455                 460

Ala Ser Gly Ile Thr Val Ile Ser Lys Asn Ser Thr Ile Pro Asp Gly
465                 470                 475                 480

Thr Val Ile

<210> SEQ ID NO 55
<211> LENGTH: 470
<212> TYPE: PRT
<213> ORGANISM: Solanum tuberosum

<400> SEQUENCE: 55

Asn Lys Ile Lys Pro Gly Val Ala Tyr Ser Val Ile Thr Thr Glu Asn
1               5                   10                  15

Asp Thr Gln Thr Val Phe Val Asp Met Pro Arg Leu Glu Arg Arg Arg
            20                  25                  30

Ala Asn Pro Lys Asp Val Ala Ala Val Ile Leu Gly Gly Gly Glu Gly
        35                  40                  45

Thr Lys Leu Phe Pro Leu Thr Ser Arg Thr Ala Thr Pro Ala Val Pro
    50                  55                  60

Val Gly Gly Cys Tyr Arg Leu Ile Asp Ile Pro Met Ser Asn Cys Ile
65                  70                  75                  80

Asn Ser Ala Ile Asn Lys Ile Phe Val Leu Thr Gln Tyr Asn Ser Ala
                85                  90                  95

Pro Leu Asn Arg His Ile Ala Arg Thr Tyr Phe Gly Asn Gly Val Ser
            100                 105                 110

Phe Gly Asp Gly Phe Val Glu Val Leu Ala Ala Thr Gln Thr Pro Gly
        115                 120                 125

Glu Ala Gly Lys Lys Trp Phe Gln Gly Thr Ala Asp Ala Val Arg Lys
    130                 135                 140

Phe Ile Trp Val Phe Glu Asp Ala Lys Asn Lys Asn Ile Glu Asn Ile
145                 150                 155                 160

Val Val Leu Ser Gly Asp His Leu Tyr Arg Met Asp Tyr Met Glu Leu
                165                 170                 175

Val Gln Asn His Ile Asp Arg Asn Ala Asp Ile Thr Leu Ser Cys Ala
            180                 185                 190
```

```
Pro Ala Glu Asp Ser Arg Ala Ser Asp Phe Gly Leu Val Lys Ile Asp
            195                 200                 205

Ser Arg Gly Arg Val Val Gln Phe Ala Glu Lys Pro Lys Gly Phe Asp
210                 215                 220

Leu Lys Ala Met Gln Val Asp Thr Thr Leu Val Gly Leu Ser Pro Gln
225                 230                 235                 240

Asp Ala Lys Lys Ser Pro Tyr Ile Ala Ser Met Gly Val Tyr Val Phe
            245                 250                 255

Lys Thr Asp Val Leu Lys Leu Leu Lys Trp Ser Tyr Pro Thr Ser
            260                 265                 270

Asn Asp Phe Gly Ser Glu Ile Ile Pro Ala Ala Ile Asp Asp Tyr Asn
            275                 280                 285

Val Gln Ala Tyr Ile Phe Lys Asp Tyr Trp Glu Asp Ile Gly Thr Ile
            290                 295                 300

Lys Ser Phe Tyr Asn Ala Ser Leu Ala Leu Thr Gln Glu Phe Pro Glu
305                 310                 315                 320

Phe Gln Phe Tyr Asp Pro Lys Thr Pro Phe Tyr Thr Ser Pro Arg Phe
            325                 330                 335

Leu Pro Pro Thr Lys Ile Asp Asn Cys Lys Ile Lys Asp Ala Ile Ile
            340                 345                 350

Ser His Gly Cys Phe Leu Arg Asp Cys Ser Val Glu His Ser Ile Val
            355                 360                 365

Gly Glu Arg Ser Arg Leu Asp Cys Gly Val Glu Leu Lys Asp Thr Phe
            370                 375                 380

Met Met Gly Ala Asp Tyr Tyr Gln Thr Glu Ser Glu Ile Ala Ser Leu
385                 390                 395                 400

Leu Ala Glu Gly Lys Val Pro Ile Gly Ile Gly Glu Asn Thr Lys Ile
            405                 410                 415

Arg Lys Cys Ile Ile Asp Lys Asn Ala Lys Ile Gly Lys Asn Val Ser
            420                 425                 430

Ile Ile Asn Lys Asp Gly Val Gln Glu Ala Asp Arg Pro Glu Glu Gly
            435                 440                 445

Phe Tyr Ile Arg Ser Gly Ile Ile Ile Leu Glu Lys Ala Thr Ile
            450                 455                 460

Arg Asp Gly Thr Val Ile
465                 470

<210> SEQ ID NO 56
<211> LENGTH: 519
<212> TYPE: PRT
<213> ORGANISM: Solanum tuberosum

<400> SEQUENCE: 56

Met Asp Ala Leu Cys Ala Ser Met Lys Gly Thr Ala Gln Leu Val Ala
1               5                   10                  15

Ile Cys Asn Gln Glu Ser Ala Phe Trp Gly Lys Ile Ser Gly Arg
            20                  25                  30

Arg Leu Ile Asn Lys Gly Phe Gly Val Arg Ser Cys Lys Ser Phe Thr
            35                  40                  45

Thr Gln Gln Arg Gly Arg Asn Val Thr Pro Ala Val Leu Thr Arg Asp
            50                  55                  60

Ile Asn Lys Glu Met Leu Pro Phe Glu Glu Ser Met Phe Glu Glu Gln
65                  70                  75                  80

Pro Thr Ala Asp Pro Lys Ala Val Ala Ser Val Ile Leu Gly Gly Gly
```

```
                     85                  90                  95
Val Gly Thr Arg Leu Phe Pro Leu Thr Ser Arg Arg Ala Lys Pro Ala
                100                 105                 110

Val Pro Ile Gly Gly Cys Tyr Arg Leu Ile Asp Val Pro Met Ser Asn
            115                 120                 125

Cys Ile Asn Ser Gly Ile Arg Lys Ile Phe Ile Leu Thr Gln Phe Asn
130                 135                 140

Ser Phe Ser Leu Asn Arg His Leu Ala Thr Tyr Asn Phe Gly Asn Gly
145                 150                 155                 160

Val Gly Phe Gly Asp Gly Phe Val Glu Val Leu Ala Gly Thr Gln Thr
                165                 170                 175

Pro Gly Asp Gly Arg Lys Met Trp Phe Gln Ala Ala Asp Ala Val Arg
            180                 185                 190

Glu Phe Ile Trp Val Phe Glu Asn Gln Lys Asn Lys Asn Val Glu His
        195                 200                 205

Ile Ile Ile Leu Ser Gly Asp His Leu Tyr Arg Met Asn Tyr Met Asp
    210                 215                 220

Phe Val Gln Lys His Ile Asp Thr Asn Ala Asp Ile Thr Val Ser Cys
225                 230                 235                 240

Val Pro Met Asp Asp Gly Arg Ala Ser Asp Phe Gly Leu Met Lys Ile
                245                 250                 255

Asp Glu Thr Gly Ala Ile Ile Gln Phe Ala Glu Lys Pro Lys Gly Pro
            260                 265                 270

Ala Leu Lys Ala Met Gln Val Asp Thr Ser Ile Leu Gly Leu Ser Glu
        275                 280                 285

Gln Glu Ala Ser Asn Phe Pro Tyr Ile Ala Ser Met Gly Val Tyr Val
    290                 295                 300

Phe Lys Thr Asp Val Leu Leu Asn Leu Leu Lys Ser Ala Tyr Pro Ser
305                 310                 315                 320

Cys Asn Asp Phe Gly Ser Glu Ile Ile Pro Ser Ala Val Lys Asp His
                325                 330                 335

Asn Val Gln Ala Tyr Leu Phe Asn Asp Tyr Trp Glu Asp Ile Gly Thr
            340                 345                 350

Val Lys Ser Phe Phe Asp Ala Asn Leu Ala Leu Thr Lys Gln Pro Pro
        355                 360                 365

Lys Phe Asp Phe Asn Asp Pro Lys Thr Pro Phe Tyr Thr Ser Ala Arg
    370                 375                 380

Phe Leu Pro Pro Thr Lys Val Asp Lys Ser Arg Ile Val Asp Ala Ile
385                 390                 395                 400

Ile Ser His Gly Cys Phe Leu Arg Glu Cys Asn Ile Gln His Ser Ile
                405                 410                 415

Val Gly Val Arg Ser Arg Leu Asp Tyr Gly Val Glu Phe Lys Asp Thr
            420                 425                 430

Met Met Met Gly Ala Asp Tyr Tyr Gln Thr Glu Cys Glu Ile Ala Ser
        435                 440                 445

Leu Leu Ala Glu Gly Lys Val Pro Ile Gly Val Gly Pro Asn Thr Lys
    450                 455                 460

Ile Gln Asn Cys Ile Ile Asp Lys Asn Ala Lys Ile Gly Lys Asp Val
465                 470                 475                 480

Val Ile Leu Asn Lys Glu Gly Val Glu Ala Asp Arg Ser Ala Glu
                485                 490                 495

Gly Phe Tyr Ile Arg Ser Gly Ile Thr Val Ile Met Lys Asn Ala Thr
            500                 505                 510
```

```
Ile Lys Asp Gly Thr Val Ile
        515

<210> SEQ ID NO 57
<211> LENGTH: 517
<212> TYPE: PRT
<213> ORGANISM: Ipomoea batatas

<400> SEQUENCE: 57

Met Glu Phe Cys Pro Thr Leu Lys Ser Ser Ala His Leu Pro Arg Glu
1               5                   10                  15

Thr Glu Phe Phe Gly Gly Arg Ile Arg Gly Ser Leu Asn Asn Asn Val
            20                  25                  30

Leu Ala Ser Lys Ser Arg Lys Ser Leu Arg Val Asp Gly Asn Lys Arg
        35                  40                  45

Lys Ile Lys Pro Gly Val Ala Phe Ser Val Leu Thr Arg Glu Asn Gly
    50                  55                  60

Thr Glu Thr Leu Thr Val Glu Ala Pro Ile Leu Glu Arg Arg Arg Ala
65                  70                  75                  80

Asn Pro Lys Asn Val Ala Ala Ile Ile Leu Gly Gly Gly Ala Gly Thr
                85                  90                  95

Gln Leu Phe Pro Leu Thr Asn Arg Ala Ala Thr Pro Ala Val Pro Leu
            100                 105                 110

Gly Gly Cys Tyr Arg Leu Ile Asp Ile Pro Met Ser Asn Cys Ile Asn
        115                 120                 125

Ser Gly Val Asn Lys Ile Phe Val Leu Thr Gln Phe Asn Ser Ala Ser
    130                 135                 140

Leu Asn Arg His Ile Ser Arg Thr Tyr Phe Gly Asn Gly Val Ser Phe
145                 150                 155                 160

Gly Asp Gly Phe Val Glu Val Leu Ala Ala Thr Gln Thr Gln Gly Glu
                165                 170                 175

Thr Gly Met Lys Trp Phe Gln Gly Thr Ala Asp Ala Val Arg Gln Phe
            180                 185                 190

Thr Trp Val Phe Glu Asp Ala Lys Asn Lys Asp Ile Asp Asn Ile Val
        195                 200                 205

Ile Leu Ser Gly Asp Gln Leu Tyr Arg Met Asp Tyr Met Asp Leu Val
    210                 215                 220

Gln Asn His Ile Glu Arg Asn Ser Asp Ile Thr Leu Ser Cys Ala Thr
225                 230                 235                 240

Val Gly Asp Ser Arg Ala Ser Asp Phe Gly Leu Val Lys Ile Asp Arg
                245                 250                 255

Arg Gly Arg Val Val Gln Phe Cys Glu Lys Pro Lys Gly Thr Asp Leu
            260                 265                 270

Lys Ala Met Gln Val Asp Thr Thr Leu Leu Gly Leu Pro Pro Gln Asp
        275                 280                 285

Ala Arg Leu Asn Pro Tyr Ile Ala Ser Met Gly Val Tyr Val Phe Lys
    290                 295                 300

Thr Asp Val Leu Leu Arg Leu Leu Arg Trp Arg Tyr Pro Thr Ser Asn
305                 310                 315                 320

Asp Phe Gly Ser Glu Ile Leu Pro Ala Ala Val Met Glu His Asn Val
                325                 330                 335

Gln Ala Tyr Ile Phe Arg Asp Tyr Trp Glu Asp Ile Gly Thr Ile Lys
            340                 345                 350

Ser Phe Tyr Asp Ala Asn Leu Ala Leu Thr Glu Glu Phe Pro Lys Phe
```

```
                355                 360                 365
Glu Phe Tyr Asp Pro Lys Thr Pro Phe Tyr Thr Ser Pro Arg Phe Leu
    370                 375                 380

Pro Pro Thr Lys Ile Asp Asn Cys Lys Ile Lys Asp Ala Ile Ile Ser
385                 390                 395                 400

His Gly Cys Phe Leu Arg Glu Cys Thr Val Glu His Ser Ile Ile Gly
                405                 410                 415

Glu Arg Ser Arg Leu Asp Cys Gly Val Glu Leu Lys Asp Thr Leu Met
            420                 425                 430

Met Gly Ala Asp Asn Tyr Glu Thr Glu Ser Glu Ile Ala Ser Leu Leu
        435                 440                 445

Ala Asp Gly Lys Val Pro Ile Gly Val Gly Glu Asn Thr Lys Ile Arg
    450                 455                 460

Asn Ala Ile Ile Asp Lys Asn Val Arg Ile Gly Lys Asp Val Val Ile
465                 470                 475                 480

Thr Asn Lys Asp Gly Val Gln Glu Ser Asp Arg Pro Asp Glu Gly Phe
                485                 490                 495

Tyr Ile Arg Ser Gly Ile Thr Ile Ile Met Glu Lys Ala Thr Ile Arg
            500                 505                 510

Asp Gly Thr Val Ile
        515

<210> SEQ ID NO 58
<211> LENGTH: 515
<212> TYPE: PRT
<213> ORGANISM: Ipomoea batatas

<400> SEQUENCE: 58

Met Asp Ala Tyr Cys Ala Thr Leu Lys Ser Thr Thr His Leu Pro Arg
1               5                   10                  15

Glu Ser Glu Leu Trp Gly Lys Arg Met Leu Lys Thr Ser Val Val Val
            20                  25                  30

Asn Gln Phe Gly Lys Ser Leu Lys Leu Glu Arg Asn Gly Arg Lys Ile
        35                  40                  45

Lys Pro Gly Val Ala Phe Ser Val Leu Thr Arg Glu Thr Gly Arg Glu
    50                  55                  60

Thr Leu Ser Val Glu Ala Pro Arg Leu Glu Arg Val Arg Ala Asn Pro
65                  70                  75                  80

Lys Asn Val Ala Ala Ile Ile Leu Gly Gly Gly Ala Gly Thr Gln Leu
                85                  90                  95

Phe Pro Leu Thr Asn Arg Ala Ala Thr Pro Ala Val Pro Val Gly Gly
            100                 105                 110

Cys Tyr Arg Met Ile Asp Ile Pro Met Ser Asn Cys Ile Asn Ser Gly
        115                 120                 125

Ile Asn Lys Ile Phe Val Leu Thr Gln Phe Asn Ser Ala Ser Leu Asn
    130                 135                 140

Arg His Ile Ala Arg Thr Tyr Phe Gly Asn Gly Val Ser Phe Gly Asp
145                 150                 155                 160

Gly Phe Val Glu Val Leu Ala Ala Thr Gln Thr Ser Gly Glu Thr Gly
                165                 170                 175

Met Lys Trp Phe Gln Gly Pro Ala Asp Ala Val Arg Lys Phe Thr Trp
            180                 185                 190

Val Phe Glu Asp Ala Lys Asn Lys Asp Ile Glu Asn Ile Leu Ile Leu
        195                 200                 205
```

Ser Gly Asp Gln Leu Tyr Arg Met Asp Tyr Met Asp Leu Val Gln Asn
210                 215                 220

His Leu Asp Arg Asn Ser Asp Ile Thr Leu Ser Cys Ala Pro Val Gly
225                 230                 235                 240

Asp Ser Arg Ala Val Asp Phe Gly Leu Val Lys Ile Asp Arg Arg Gly
            245                 250                 255

Lys Val Val Gln Phe Gln Glu Lys Pro Lys Gly Ala Asp Leu Glu Ala
                260                 265                 270

Met Gln Val Asp Thr Thr Arg Leu Gly Leu Ser Pro Glu Asp Ala Lys
            275                 280                 285

Arg Asn Pro Tyr Ile Ala Ser Met Gly Leu Tyr Val Phe Arg Arg Asp
290                 295                 300

Leu Leu Leu Asn Leu Leu Arg Trp Ile Tyr Pro Thr Ala Asn Asp Phe
305                 310                 315                 320

Gly Ser Glu Ile Ile Pro Ala Val Ile Thr Glu His Asn Val Gln Ala
                325                 330                 335

Tyr Phe Phe Lys Asp Tyr Trp Glu Asp Ile Gly Thr Ile Lys Thr Phe
            340                 345                 350

Tyr Asp Ala Asn Leu Ala Leu Ala Glu Glu Phe Pro Lys Phe Glu Phe
            355                 360                 365

Tyr Asp Pro Lys Thr Pro Phe Tyr Thr Ser Pro Arg Phe Leu Pro Pro
370                 375                 380

Thr Lys Ile Asp Asn Cys Lys Ile Lys Asp Ala Ile Ile Ser His Gly
385                 390                 395                 400

Cys Phe Leu Arg Glu Cys Ile Val Glu His Ser Ile Val Gly Glu Arg
                405                 410                 415

Ser Arg Leu Asp Phe Gly Val Glu Leu Lys Asp Thr Leu Met Met Gly
            420                 425                 430

Ala Asp Tyr Tyr Glu Thr Glu Ser Glu Ile Ala Ser Leu Leu Ala Asp
            435                 440                 445

Gly Lys Val Pro Ile Gly Ile Gly His Asn Thr Lys Ile Ser Asn Cys
450                 455                 460

Ile Ile Asp Lys Asn Val Arg Ile Gly Lys Asp Val Ile Ile Ala Asn
465                 470                 475                 480

Lys Asp Gly Val Glu Glu Ala Asp Arg Pro Glu Glu Gly Phe Tyr Ile
            485                 490                 495

Arg Ser Gly Ile Pro Val Ile Met Glu Lys Ala Val Ile Lys Asp Gly
            500                 505                 510

Thr Val Ile
515

<210> SEQ ID NO 59
<211> LENGTH: 518
<212> TYPE: PRT
<213> ORGANISM: Ipomoea batatas

<400> SEQUENCE: 59

Met Asp Ala Leu Cys Ala Ser Met Arg Ala His Pro Val Pro Val Ser
1               5                   10                  15

Lys Gly Phe Gly Tyr Gly Asp Ser Gly Leu Trp Gly Lys Ile Arg
                20                  25                  30

Gly Cys Ser Arg Ile Lys Thr Glu Arg His Glu Gly Met Pro Lys Lys
            35                  40                  45

Val Asn Leu Gly Val Ala Cys Ser Ile Leu Thr His Asp Ile Asn Lys
50                  55                  60

```
Glu His Leu Ser Phe Glu Thr Gln His Phe Glu His Ser Gln Gly
 65                  70                  75                  80

Asp Pro Arg Asn Val Ala Ser Ile Val Leu Gly Gly Ala Gly Thr
                 85                  90                  95

Arg Leu Phe Pro Leu Thr Arg Ser Arg Ala Lys Pro Ala Val Pro Ile
                100                 105                 110

Gly Gly Cys Tyr Arg Leu Ile Asp Val Pro Met Ser Asn Cys Ile Asn
                115                 120                 125

Ser Gly Ile Arg Lys Ile Phe Ile Leu Thr Gln Phe Asn Ser Phe Ser
                130                 135                 140

Leu Asn Arg His Leu Ala Arg Ala Tyr Gly Ile Gly Asn Gly Val Asn
145                 150                 155                 160

Phe Gly Asp Gly Phe Val Glu Val Leu Ala Ala Thr Gln Thr Pro Gly
                165                 170                 175

Glu Ala Gly Lys Met Trp Phe Gln Gly Thr Ala Asp Ala Val Arg Gln
                180                 185                 190

Phe Ile Trp Val Phe Glu Asp Ala Lys Asn Lys Asn Ile Asp Asn Ile
                195                 200                 205

Leu Ile Leu Ser Gly Asp His Leu Tyr Arg Met Asp Tyr Met Asp Phe
210                 215                 220

Val Gln Arg His Ile Asp Thr Asn Ala Asp Ile Thr Val Ser Cys Val
225                 230                 235                 240

Pro Met Asp Asp Ser Arg Ala Ser Asp Tyr Gly Leu Met Lys Ile Asp
                245                 250                 255

Gly Ser Gly Arg Ile Val His Phe Ala Glu Lys Pro Lys Gly Pro Ala
                260                 265                 270

Leu Lys Thr Met Gln Val Asp Thr Ser Leu Leu Gly Leu Ser Glu Asn
                275                 280                 285

Glu Ala Lys Lys Tyr Pro Tyr Ile Ala Ser Met Gly Val Tyr Val Phe
290                 295                 300

Arg Thr Glu Val Leu Leu Asn Leu Leu Arg Ser Gln Tyr Pro Ser Cys
305                 310                 315                 320

Asn Asp Phe Gly Ser Glu Ile Ile Pro Ala Ala Val Lys Asp His Asn
                325                 330                 335

Val Gln Ala Tyr Leu Phe Ser Asp Tyr Trp Glu Asp Ile Gly Thr Val
                340                 345                 350

Lys Ser Phe Phe Asp Ala Asn Leu Ala Leu Thr Glu Gln Pro Pro Met
                355                 360                 365

Phe Asp Phe Asn Asp Pro Lys Thr Pro Phe Tyr Thr Ser Pro Arg Phe
                370                 375                 380

Leu Pro Pro Thr Lys Val Asp Lys Cys Lys Ile Val Asp Ala Ile Ile
385                 390                 395                 400

Ser His Gly Cys Phe Leu Arg Glu Cys Ser Val Lys His Ser Ile Val
                405                 410                 415

Gly Ile Arg Ser Arg Leu Asp Tyr Gly Val Glu Leu Glu Asp Thr Met
                420                 425                 430

Val Met Gly Ala Asp Tyr Tyr Gln Thr Glu Ser Glu Ile Ala Ser Leu
                435                 440                 445

Leu Ala Thr Gly Lys Val Pro Ile Gly Ile Gly Thr Asn Thr Lys Ile
                450                 455                 460

Arg Asn Cys Ile Ile Asp Lys Asn Ala Arg Ile Gly Lys Asp Val Val
465                 470                 475                 480
```

```
Ile Ala Asn Lys Asp Gly Val Asp Glu Ala Asp Arg Ala Asp Glu Gly
            485                 490                 495

Phe Tyr Ile Arg Ser Gly Ile Thr Ile Val Leu Lys Asn Ala Thr Ile
            500                 505                 510

Arg Asp Gly Thr Val Ile
        515

<210> SEQ ID NO 60
<211> LENGTH: 525
<212> TYPE: PRT
<213> ORGANISM: Ipomoea batatas

<400> SEQUENCE: 60

Met Ala Val Thr Ala Asp Gly Arg Ile Ala Leu Leu Ala Ala Arg Gln
1               5                   10                  15

Leu Arg Glu Gly Ala Ala Met Thr Val Ser Ser Cys Arg Leu Ser Val
            20                  25                  30

Lys Phe Cys Asn Gly Glu Phe Met Gly Lys Lys Ile Lys Leu Arg Lys
        35                  40                  45

Phe Gln Gln Arg Asn Gly Thr Lys Tyr Asn Val Val Ala Arg Pro Arg
    50                  55                  60

Val Ser Met Ser Leu Thr Thr Asp Val Ala Gly Glu Ala Lys Leu Lys
65                  70                  75                  80

Asp Tyr Gly Met Glu Lys Thr Asp Pro Arg Thr Val Val Ala Ile Ile
                85                  90                  95

Leu Gly Gly Gly Ala Gly Thr Arg Leu Phe Pro Leu Thr Lys Arg Arg
            100                 105                 110

Ala Lys Pro Ala Val Pro Ile Gly Gly Ala Tyr Arg Leu Ile Asp Val
        115                 120                 125

Pro Met Ser Asn Cys Ile Asn Ser Gly Ile Asn Lys Val Tyr Ile Leu
    130                 135                 140

Thr Gln Phe Asn Ser Ala Ser Leu Asn Arg His Leu Ala Arg Ala Tyr
145                 150                 155                 160

Asn Phe Gly Ser Gly Val Thr Phe Gly Asp Gly Tyr Val Glu Val Leu
                165                 170                 175

Ala Ala Thr Gln Thr Pro Gly Glu Ala Gly Lys Arg Trp Phe Gln Gly
            180                 185                 190

Thr Ala Asp Ala Val Arg Gln Phe His Trp Leu Phe Glu Asp Pro Lys
        195                 200                 205

Ser Lys Asp Ile Glu Asp Val Leu Ile Leu Ser Gly Asp His Leu Tyr
    210                 215                 220

Arg Met Asp Tyr Met Asp Phe Val Gln Ser His Arg Gln Ser Gly Ala
225                 230                 235                 240

Asp Ile Thr Ile Ser Ser Leu Pro Ile Asp Asp Arg Arg Ala Ser Asp
                245                 250                 255

Phe Gly Leu Met Lys Ile Asp Asp Lys Gly Arg Val Leu Phe Phe Ser
            260                 265                 270

Glu Lys Pro Lys Gly Asp Asp Leu Lys Ala Met Ala Val Asp Thr Ser
        275                 280                 285

Val Leu Gly Leu Ser Pro Glu Glu Ala Lys Gln Lys Pro Tyr Ile Ala
    290                 295                 300

Ser Met Gly Val Tyr Val Phe Lys Lys Glu Ile Leu Leu Asn Leu Leu
305                 310                 315                 320

Arg Trp Arg Phe Pro Thr Ala Asn Asp Phe Gly Ser Glu Ile Ile Pro
                325                 330                 335
```

```
Ala Ser Ala Arg Glu Phe Tyr Ile Gln Ala Tyr Leu Phe Asn Asp Tyr
            340                 345                 350

Trp Glu Asp Ile Gly Thr Ile Arg Ser Phe Phe Glu Ala Asn Leu Ala
            355                 360                 365

Leu Thr Glu His Pro Pro Arg Phe Ser Phe Tyr Asp Ala Thr Lys Pro
        370                 375                 380

Ile Tyr Thr Ser Arg Arg Asn Leu Pro Pro Ser Ala Ile Thr Asn Ser
385                 390                 395                 400

Lys Ile Val Asp Ser Ile Ile Ser His Gly Ser Phe Leu Ser Asp Cys
                405                 410                 415

Phe Val Glu His Ser Val Val Gly Ile Arg Ser Arg Ile Asn Ser Asn
            420                 425                 430

Val His Leu Lys Asp Thr Val Met Leu Gly Ala Asp Tyr Tyr Glu Thr
        435                 440                 445

Gly Ala Glu Ile Ala Ser Leu Leu Thr Glu Gly Val Pro Ile Gly
    450                 455                 460

Ile Gly Glu Asn Ser Arg Ile Lys Glu Cys Ile Ile Asp Lys Asn Ala
465                 470                 475                 480

Arg Ile Gly Lys Asn Val Val Ile Ala Asn Ser Glu Gly Ile Gln Glu
                485                 490                 495

Ala Asp Arg Thr Ser Glu Gly Phe Tyr Ile Arg Ser Gly Val Thr Val
            500                 505                 510

Ile Leu Lys Asn Ser Thr Ile Pro Asp Gly Leu Val Ile
        515                 520                 525

<210> SEQ ID NO 61
<211> LENGTH: 527
<212> TYPE: PRT
<213> ORGANISM: Citrus sinensis

<400> SEQUENCE: 61

Met Asp Ser Cys Cys Val Gly Leu Arg Ala Asn Thr His Val Val Lys
1               5                   10                  15

Ala Ser Lys Tyr Gly Ser Lys Ile Gly Asp Asn Ala Leu Trp Gly Glu
            20                  25                  30

Arg Ile Arg Gly Ser Val Ser Asn Asp Gly Cys Thr Lys Gln Leu Lys
        35                  40                  45

Lys Ser Leu Lys Ala Glu Lys Arg Asp Glu Lys Val Lys Pro Gly Val
    50                  55                  60

Ala Tyr Ala Val Met Thr Ser Lys His Pro Asn Glu Val Met Thr Leu
65                  70                  75                  80

Ala Pro Pro Arg Leu Glu Arg Arg Val Asp Pro Lys Asn Val Ala
                85                  90                  95

Ala Ile Ile Leu Gly Gly Gly Ala Gly Thr Lys Leu Phe Pro Leu Thr
            100                 105                 110

Leu Arg Ala Ala Thr Pro Ala Val Pro Val Ala Gly Cys Tyr Arg Leu
        115                 120                 125

Ile Asp Ile Pro Met Ser Asn Cys Ile Asn Ser Gly Ile Asn Lys Ile
    130                 135                 140

Phe Val Leu Thr Gln Phe Asn Ser Ala Ser Leu Asn Arg His Ile Ala
145                 150                 155                 160

Arg Thr Tyr Phe Gly Asn Gly Thr Asn Phe Gly Asp Gly Phe Val Glu
                165                 170                 175

Val Leu Ala Ala Thr Gln Thr Pro Gly Glu Ser Gly Lys Asn Trp Phe
```

```
                    180                 185                 190
Gln Gly Thr Ala Asp Ala Val Arg Gln Phe Thr Trp Val Phe Glu Asp
                195                 200                 205
Ala Lys Asn Arg Asn Ile Glu Asn Val Ala Ile Leu Cys Gly Asp His
            210                 215                 220
Leu Tyr Arg Met Asp Tyr Met Asp Phe Ile Gln Ser His Val Asp Arg
225                 230                 235                 240
Asp Ala Asp Ile Thr Ile Ser Cys Ala Ala Val Gly Glu Ser Arg Ala
                245                 250                 255
Ser Asp Tyr Gly Leu Val Lys Ile Asp Asn Met Gly Arg Ile Ala Gln
                260                 265                 270
Phe Ala Glu Lys Pro Ser Gly Ala Asn Leu Lys Ala Met Gln Val Asp
                275                 280                 285
Thr Ser Leu Leu Gly Phe Ser Pro Gln Glu Ala Arg Lys Cys Pro Tyr
            290                 295                 300
Val Ala Ser Met Gly Val Tyr Val Phe Lys Lys Asp Val Leu Leu Lys
305                 310                 315                 320
Leu Leu Arg Trp Arg Tyr Pro Thr Ser Asn Asp Phe Gly Ser Glu Ile
                325                 330                 335
Ile Pro Ala Ala Ile Met Glu His Asp Val Gln Ala Tyr Ile Phe Arg
                340                 345                 350
Asp Tyr Trp Glu Asp Ile Gly Thr Ile Lys Ser Phe Tyr Glu Ala Asn
                355                 360                 365
Met Ala Leu Thr Lys Glu Ser Pro Ala Phe His Phe Tyr Asp Pro Lys
            370                 375                 380
Thr Pro Phe Tyr Thr Ser Pro Arg Phe Leu Pro Pro Thr Lys Ile Asp
385                 390                 395                 400
Asn Cys Arg Met Lys Asp Ala Ile Ile Ser His Gly Cys Phe Leu Arg
                405                 410                 415
Glu Cys Thr Val Glu His Ser Ile Val Gly Glu Arg Ser Arg Ile Asp
                420                 425                 430
Tyr Gly Val Glu Leu Lys Asp Thr Val Met Leu Gly Ala Asp Tyr Tyr
            435                 440                 445
Gln Thr Glu Ser Glu Ile Ala Ser Leu Leu Ala Glu Gly Lys Val Pro
        450                 455                 460
Ile Gly Val Gly Arg Asn Thr Lys Ile Arg Asn Cys Ile Ile Asp Lys
465                 470                 475                 480
Asn Val Lys Ile Gly Lys Asp Val Val Ile Val Asn Lys Asp Gly Val
                485                 490                 495
Gln Glu Ala Asp Arg Pro Glu Leu Gly Phe Tyr Ile Arg Ser Gly Ile
                500                 505                 510
Thr Ile Ile Met Glu Lys Ala Thr Ile Glu Asp Gly Met Val Ile
            515                 520                 525

<210> SEQ ID NO 62
<211> LENGTH: 510
<212> TYPE: PRT
<213> ORGANISM: Pisum sativum

<400> SEQUENCE: 62

Met Ala Ser Gly Cys Val Ser Leu Lys Thr Asn Thr His Phe Pro Asn
1               5                   10                  15
Ser Lys Lys Gly Ser Phe Phe Gly Glu Arg Ile Lys Gly Ser Leu Lys
            20                  25                  30
```

-continued

```
Asn Ser Ser Trp Val Thr Thr Gln Lys Lys Ile Lys Pro Ala Ser Phe
         35                  40                  45
Ser Ala Ile Leu Thr Ser Asp Asp Pro Lys Gly Ser Leu Asn Leu Gln
 50                  55                  60
Val Pro Ser Phe Leu Arg Leu Arg Ala Asp Pro Lys Asn Val Ile Ser
 65                  70                  75                  80
Ile Val Leu Gly Gly Gly Pro Gly Thr His Leu Tyr Pro Leu Thr Lys
                 85                  90                  95
Arg Ala Ala Thr Pro Ala Val Pro Val Gly Gly Cys Tyr Arg Leu Ile
             100                 105                 110
Asp Ile Pro Met Ser Asn Cys Ile Asn Ser Gly Ile Asn Lys Ile Phe
             115                 120                 125
Val Leu Thr Gln Phe Asn Ser Ala Ser Leu Asn Arg His Ile Ala Arg
130                 135                 140
Thr Tyr Phe Gly Asn Gly Val Asn Phe Gly Asp Gly Phe Val Glu Val
145                 150                 155                 160
Leu Ala Ala Thr Gln Thr Pro Gly Glu Ala Gly Lys Lys Trp Phe Gln
                165                 170                 175
Gly Thr Ala Asp Ala Val Arg Gln Phe Thr Trp Ile Phe Glu Asp Ala
            180                 185                 190
Lys Asn Ile Asn Val Glu Asn Val Leu Ile Leu Ala Gly Asp His Leu
        195                 200                 205
Tyr Arg Met Asp Tyr Met Asp Leu Leu Gln Ser His Val Asp Arg Asn
    210                 215                 220
Ala Asp Ile Thr Val Ser Cys Ala Ala Val Gly Asp Asn Arg Ala Ser
225                 230                 235                 240
Asp Tyr Gly Leu Val Lys Val Asp Asp Arg Gly Asn Ile Ile Gln Phe
                245                 250                 255
Ser Glu Lys Pro Lys Gly Ala Asp Leu Lys Ala Met Gln Val Asp Thr
            260                 265                 270
Ser Arg Leu Gly Leu Ser Pro Gln Asp Ala Leu Lys Ser Pro Tyr Ile
        275                 280                 285
Ala Ser Met Gly Val Tyr Val Phe Lys Lys Asp Val Leu Leu Lys Leu
    290                 295                 300
Leu Lys Trp Arg Tyr Pro Thr Ser Asn Asp Phe Gly Ser Glu Ile Ile
305                 310                 315                 320
Pro Ser Ala Ile Arg Glu His Asn Val Gln Ala Tyr Phe Phe Gly Asp
                325                 330                 335
Tyr Trp Glu Asp Ile Gly Thr Ile Lys Ser Phe Tyr Asp Ala Asn Leu
            340                 345                 350
Ala Leu Thr Glu Glu Ser Pro Lys Phe Glu Phe Tyr Asp Pro Lys Thr
        355                 360                 365
Pro Ile Phe Thr Ser Pro Gly Phe Leu Pro Pro Thr Lys Ile Asp Asn
    370                 375                 380
Ser Arg Val Val Asp Ala Ile Ile Ser His Gly Cys Phe Leu Arg Asp
385                 390                 395                 400
Cys Thr Ile Gln His Ser Ile Val Gly Glu Arg Ser Arg Leu Asp Tyr
                405                 410                 415
Gly Val Glu Leu Gln Asp Thr Val Met Met Gly Ala Asp Tyr Tyr Gln
            420                 425                 430
Thr Glu Ser Glu Ile Ala Ser Leu Leu Ala Glu Gly Lys Val Pro Ile
        435                 440                 445
Gly Ile Gly Arg Asn Thr Lys Ile Lys Asn Cys Ile Ile Asp Lys Asn
```

```
                    450               455                460
Ala Lys Ile Gly Lys Glu Val Ile Ala Asn Lys Glu Gly Val Gln
465                 470                475                480

Glu Ala Asp Arg Ser Glu Asp Gly Phe Tyr Ile Arg Ser Gly Ile Thr
                485                 490                 495

Ile Ile Met Glu Lys Ala Thr Ile Glu Asp Gly Thr Val Ile
                500                 505                 510

<210> SEQ ID NO 63
<211> LENGTH: 507
<212> TYPE: PRT
<213> ORGANISM: Fragaria x ananassa

<400> SEQUENCE: 63

Met Asp Ser Trp Cys Val Thr Leu Lys Pro Asn Thr His Leu Arg Gln
1               5                   10                  15

Pro Thr Gln Ala Gly Leu Cys Cys Gly Ala Asn Gly Phe Leu Gly Gln
                20                  25                  30

Arg Ile Arg Glu Ser Phe Gly Asn Arg Gly Trp Val His Gly Ser Glu
            35                  40                  45

Lys Thr Arg Pro Gly Val Val Ser Ser Val Val Thr Thr Lys Asp Phe
50                  55                  60

Glu Thr Thr Leu Lys Val Pro Thr Tyr His Arg Pro Arg Val Asp Pro
65                  70                  75                  80

Lys Asn Val Ala Ser Ile Ile Leu Gly Gly Gly Ala Phe Thr Gln Leu
                85                  90                  95

Phe Pro Leu Thr Arg Arg Ala Ala Thr Pro Ala Val Pro Val Gly Gly
                100                 105                 110

Cys Tyr Arg Leu Ile Asp Ile Pro Met Ser Asn Cys Ile Asn Ser Asn
            115                 120                 125

Ile Asn Lys Ile Phe Val Leu Thr Gln Phe Asn Ser Thr Ser Leu Asn
130                 135                 140

Arg His Leu Ala Arg Thr Tyr Phe Gly Asn Gly Ile Asn Phe Gly Asp
145                 150                 155                 160

Gly Phe Val Glu Val Leu Ala Ala Thr Gln Thr Ser Gly Glu Ala Gly
                165                 170                 175

Met Asp Trp Phe Gln Gly Thr Ala Asp Ala Val Arg Gln Phe Val Trp
            180                 185                 190

Val Phe Glu Asp Ala Lys Asn Arg Asn Val Glu Asn Ile Leu Ile Leu
            195                 200                 205

Ser Gly Asp His Leu Tyr Arg Met Asp Tyr Met Asp Phe Val Gln Ser
210                 215                 220

His Val Asp Ser Asn Ala Asp Ile Thr Leu Ser Cys Ala Val Val Gly
225                 230                 235                 240

Asp Ser Arg Ala Ser Asp Tyr Gly Leu Val Lys Ile Asp Ser Arg Gly
                245                 250                 255

Lys Ile Ile Gln Phe Ala Glu Lys Pro Arg Gly Ala Gly Leu Lys Ala
            260                 265                 270

Met Gln Ser Asp Thr Thr Leu Leu Gly Phe Ser Pro Gln Asp Ala Leu
            275                 280                 285

Lys Ser Pro Tyr Val Ala Ser Met Gly Val Tyr Val Phe Lys Thr Asp
            290                 295                 300

Ile Leu Leu Glu Leu Leu Lys Lys Ser Tyr Pro Asn Ser Asn Asp Phe
305                 310                 315                 320
```

```
Gly Ser Glu Ile Ile Pro Ala Ala Val Glu Arg Asn Val Gln Ala
                325                 330                 335

Tyr Ile Phe Ile Asp Tyr Trp Glu Asp Ile Gly Thr Ile Gln Ser Phe
    340                 345                 350

Tyr Asp Ala Asn Leu Ala Leu Thr Glu Glu Phe Pro Lys Phe Gln Phe
            355                 360                 365

Tyr Asp Pro Lys Thr Pro Phe Phe Thr Ser Pro Arg Phe Leu Pro Pro
    370                 375                 380

Thr Lys Ile Asp Asn Ser Arg Val Val Asp Ala Ile Ile Ser His Gly
385                 390                 395                 400

Cys Phe Leu Gln Glu Cys Phe Val Gln Ser Ser Ile Val Gly Glu Arg
                405                 410                 415

Ser Arg Leu Asp Tyr Gly Val Glu Leu Lys Asp Ser Ile Met Met Gly
            420                 425                 430

Ala Asp Ser Tyr Gln Thr Glu Ser Glu Ile Ala Ala Leu Leu Ala Arg
        435                 440                 445

Gly Lys Val Pro Ile Gly Ile Gly Arg Asn Thr Lys Ile Arg Leu Cys
    450                 455                 460

Ile Val Asp Leu Asn Ala Lys Ile Gly Lys Asp Val Ile Ile Met Asn
465                 470                 475                 480

Lys Asp Gly Ile Gln Glu Ala Asp Arg Pro Glu Gly Phe Tyr Ile
                485                 490                 495

Arg Glu Glu Ser Leu Ser Leu Trp Arg Arg Glu
            500                 505
```

<210> SEQ ID NO 64
<211> LENGTH: 522
<212> TYPE: PRT
<213> ORGANISM: Beta vulgaris

<400> SEQUENCE: 64

```
Met Asp Ala Ser Ala Ala Ile Asn Val Asn Ala His Leu Thr Glu
1               5                   10                  15

Val Gly Lys Lys Arg Phe Leu Gly Glu Arg Ile Ser Gln Ser Leu Lys
                20                  25                  30

Gly Lys Asp Leu Arg Ala Leu Phe Ser Arg Thr Glu Ser Lys Gly Arg
            35                  40                  45

Asn Val Asn Lys Pro Gly Val Ala Phe Ser Val Leu Thr Ser Asp Phe
    50                  55                  60

Asn Gln Ser Val Lys Glu Ser Leu Lys Tyr Glu Pro Ala Leu Phe Glu
65                  70                  75                  80

Ser Pro Lys Ala Asp Pro Lys Asn Val Ala Ala Ile Val Leu Gly Gly
                85                  90                  95

Gly Ala Gly Thr Arg Leu Phe Pro Leu Thr Ser Arg Arg Ala Lys Pro
            100                 105                 110

Ala Val Pro Ile Gly Gly Cys Tyr Arg Leu Ile Asp Val Pro Met Ser
        115                 120                 125

Asn Cys Ile Asn Ser Gly Ile Arg Lys Ile Phe Ile Leu Thr Gln Phe
    130                 135                 140

Asn Ser Phe Ser Leu Asn Arg His Leu Ala Arg Thr Tyr Asn Phe Gly
145                 150                 155                 160

Asp Gly Val Asn Phe Gly Asp Gly Phe Val Glu Val Phe Ala Ala Thr
                165                 170                 175

Gln Thr Pro Gly Glu Ser Gly Lys Lys Trp Phe Gln Gly Thr Ala Asp
            180                 185                 190
```

Ala Val Arg Gln Phe Phe Trp Ala Phe Glu Asp Ser Lys Ser Lys Asp
            195                 200                 205

Val Glu His Ile Val Ile Leu Ser Gly Asp His Leu Tyr Arg Met Asp
    210                 215                 220

Tyr Met Ser Phe Trp Gln Lys His Ile Asp Thr Asn Ala Asp Ile Thr
225                 230                 235                 240

Val Ser Cys Ile Pro Met Asp Asp Ser Arg Ala Ser Asp Tyr Gly Leu
            245                 250                 255

Met Lys Ile Asp His Thr Gly Arg Ile Val His Phe Ala Glu Lys Pro
            260                 265                 270

Lys Gly Ser Asp Leu Thr Ala Met Gln Val Asp Thr Thr Val Leu Gly
            275                 280                 285

Leu Ser Asp Leu Glu Ala Met Ser Asn Pro Tyr Ile Ala Ser Met Gly
            290                 295                 300

Val Tyr Val Phe Arg Thr Asp Val Leu Met Glu Leu Leu Asn Arg Lys
305                 310                 315                 320

Tyr Pro Ser Ser Asn Asp Phe Gly Ser Glu Ile Ile Pro Ser Ala Val
            325                 330                 335

Gly Glu Ser Asn Val Gln Ala Tyr Leu Phe Asn Asp Tyr Trp Glu Asp
            340                 345                 350

Ile Gly Thr Ile Lys Ser Phe Phe Asp Ser Asn Leu Ala Leu Thr Gln
            355                 360                 365

Gln Pro Pro Lys Phe Glu Phe Tyr Asp Pro Lys Thr Pro Phe Tyr Thr
            370                 375                 380

Ser Ala Arg Phe Leu Pro Pro Thr Lys Val Asp Arg Cys Lys Ile Val
385                 390                 395                 400

Asp Ser Ile Val Ser His Gly Cys Phe Leu Gln Glu Ser Ser Ile Gln
            405                 410                 415

His Ser Ile Val Gly Val Arg Ser Arg Leu Glu Ser Gly Val Glu Phe
            420                 425                 430

Gln Asp Thr Met Met Met Gly Ala Asp Tyr Tyr Gln Thr Glu Ser Glu
            435                 440                 445

Ile Ala Ser Leu Leu Ala Glu Gly Lys Val Pro Val Gly Val Gly Gln
            450                 455                 460

Asn Thr Lys Ile Lys Asn Cys Ile Ile Asp Lys Asn Ala Lys Ile Gly
465                 470                 475                 480

Lys Asp Val Val Ile Ala Asn Thr Asp Gly Val Glu Glu Ala Asp Arg
            485                 490                 495

Pro Asn Glu Gly Phe Tyr Ile Arg Ser Gly Ile Thr Ile Ile Leu Lys
            500                 505                 510

Asn Ala Thr Ile Gln Asp Gly Leu Val Ile
            515                 520

<210> SEQ ID NO 65
<211> LENGTH: 521
<212> TYPE: PRT
<213> ORGANISM: Cicer arietinum

<400> SEQUENCE: 65

Met Asp Leu Ala Ile Gly Ser Asn Tyr Ala Ser Leu Arg Ser Ser Val
1               5                   10                  15

Phe Leu Gly Glu Thr Leu Lys Gly Asn Leu Ser Thr Lys Phe Leu Thr
            20                  25                  30

Ser Pro Lys Phe Ser Gln Ile His Ile Asn Asn Leu Arg Ser Phe Asn

-continued

```
                35                  40                  45
Pro Arg Asn Gly Ala Ser Tyr Ser Val Leu Thr Ser Gly Ile Asn Asp
 50                  55                  60

Phe Glu Glu Ser Met Thr Phe His Glu Gly Pro Tyr Phe Asp Thr Pro
65                   70                  75                  80

Lys Ala Asp Pro Lys Ser Val Ala Ser Ile Leu Gly Gly Gly Ala
                 85                  90                  95

Gly Thr Arg Leu Phe Pro Leu Thr Ser Lys Arg Ala Lys Pro Ala Val
                100                 105                 110

Pro Ile Gly Gly Cys Tyr Arg Leu Ile Asp Ile Pro Met Ser Asn Cys
                115                 120                 125

Ile Asn Ser Gly Ile Arg Lys Ile Phe Ile Leu Thr Gln Phe Asn Ser
                130                 135                 140

Phe Ser Leu Asn Arg His Leu Ser Arg Ser Tyr Asn Phe Gly Asn Val
145                 150                 155                 160

Ser Thr Phe Gly Glu Gly Phe Val Glu Val Leu Ala Ala Thr Gln Thr
                165                 170                 175

Ser Gly Glu Ala Gly Lys Lys Trp Phe Gln Gly Thr Ala Asp Ala Val
                180                 185                 190

Arg Gln Phe Ile Trp Val Phe Glu Asp Ala Lys Thr Lys Asn Val Glu
                195                 200                 205

His Ile Leu Ile Leu Ser Gly Asp His Leu Tyr Arg Met Asn Tyr Met
                210                 215                 220

Asp Phe Val Gln Lys His Ile Asp Thr Asn Ala Asp Ile Thr Val Ser
225                 230                 235                 240

Cys Ile Pro Met Asp Asp Ser Arg Ala Ser Asp Tyr Gly Leu Leu Lys
                245                 250                 255

Ile Asp Gly Lys Gly Arg Ile Ile Gln Phe Ala Glu Lys Pro Lys Gly
                260                 265                 270

Ser Glu Leu Lys Ala Met Arg Val Asp Thr Thr Leu Leu Gly Leu Ser
                275                 280                 285

Pro Glu Glu Ala Lys Lys Gln Pro Tyr Ile Ala Ser Met Gly Val Tyr
                290                 295                 300

Val Phe Arg Thr Glu Thr Leu Leu Lys Leu Leu Arg Ser Asn Cys Ser
305                 310                 315                 320

Thr Cys Asn Asp Phe Gly Ser Glu Ile Ile Pro Ser Ala Val Asn Asp
                325                 330                 335

Asp His Asn Val Gln Ala Tyr Leu Phe Asn Asp Tyr Trp Glu Asp Ile
                340                 345                 350

Gly Thr Ile Lys Ser Phe Phe Asp Ala Asn Leu Ala Leu Thr Asp Gln
                355                 360                 365

Pro Pro Lys Phe Gln Phe Tyr Asp Pro Asn Thr Pro Phe Tyr Thr Phe
                370                 375                 380

Pro Arg Phe Leu Pro Pro Thr Lys Val Glu Lys Cys Lys Ile Val Asp
385                 390                 395                 400

Ala Ile Ile Ser His Gly Cys Phe Leu Arg Glu Cys Ser Val Gln His
                405                 410                 415

Ser Ile Val Gly Ile Arg Ser Arg Leu Glu Ser Gly Val Glu Leu Gln
                420                 425                 430

Asp Thr Met Met Met Gly Ala Asp Tyr Tyr Gln Thr Glu Ser Glu Ile
                435                 440                 445

Ala Ser Leu Leu Ala Glu Gly Lys Val Pro Val Gly Val Gly Glu Asn
                450                 455                 460
```

```
Thr Lys Ile Arg Asn Cys Ile Ile Asp Lys Asn Ala Arg Ile Gly Arg
465                 470                 475                 480

Asn Val Ile Ile Thr Asn Ala Asp Gly Val Glu Glu Ala Asp Arg Thr
            485                 490                 495

Lys Glu Gly Phe Tyr Ile Arg Ser Gly Ile Thr Ala Ile Leu Lys Asn
            500                 505                 510

Ala Thr Ile Lys Asp Gly Thr Val Ile
        515                 520
```

```
<210> SEQ ID NO 66
<211> LENGTH: 481
<212> TYPE: PRT
<213> ORGANISM: Citrullus lanatus

<400> SEQUENCE: 66

Asn Ser Asn Ser Ser Pro Arg Ser Thr Ala Arg Lys Leu Thr Pro Gly
1               5                   10                  15

Val Ala Tyr Ser Val Leu Met Ser Glu Ile Ser Glu Val Ser Ser Thr
            20                  25                  30

Leu Gln Ala Pro Ile Phe Glu Thr Pro Arg Ala Asp Pro Lys Lys Ile
        35                  40                  45

Ala Ser Ile Ile Leu Gly Gly Ala Gly Thr Arg Leu Phe Pro Leu
    50                  55                  60

Thr Ser Gln Arg Ala Lys Pro Ala Val Pro Ile Gly Gly Cys Tyr Arg
65                  70                  75                  80

Leu Ile Asp Ile Pro Met Ser Asn Cys Ile Asn Ser Gly Ile Glu Lys
                85                  90                  95

Ile Phe Val Leu Thr Gln Phe Asn Ser Phe Ser Leu Asn Arg His Leu
            100                 105                 110

Ala Arg Ile Tyr Asn Phe Gly Asn Gly Val Asn Phe Gly Asp Gly Phe
        115                 120                 125

Val Glu Val Leu Ala Ala Thr Gln Thr Ser Gly Glu Thr Gly Lys Lys
    130                 135                 140

Trp Phe Gln Gly Thr Ala Asp Ala Val Arg Gln Phe Ile Trp Leu Phe
145                 150                 155                 160

Glu Asp Ala Lys Thr Lys Asn Val Glu His Thr Leu Ile Leu Ser Gly
                165                 170                 175

Asp His Leu Tyr Arg Met Asp Tyr Met Asp Phe Val Gln Arg His Ile
            180                 185                 190

Asp Thr Asn Ala Asp Ile Thr Val Ser Cys Ile Pro Met Asp Asp Ser
        195                 200                 205

Arg Ala Ser Asp Tyr Gly Leu Met Lys Ile Asp Asp Thr Gly Arg Ile
    210                 215                 220

Leu His Phe Ala Glu Lys Pro Lys Gly Ser Asp Leu Glu Ala Met Lys
225                 230                 235                 240

Val Asp Thr Thr Val Leu Gly Leu Ser Asn Gln Asp Ala Arg Lys Asn
                245                 250                 255

Pro Tyr Ile Ala Ser Met Gly Val Tyr Ile Phe Arg Thr Asp Leu Leu
            260                 265                 270

Leu Lys Leu Leu Thr Trp Ser Tyr Pro Ser Cys Asn Asp Phe Gly Ser
        275                 280                 285

Glu Ile Ile Pro Ser Ala Val Lys Asp Tyr Lys Val Gln Ala Tyr Leu
    290                 295                 300

Phe Asn Asp Tyr Trp Glu Asp Ile Gly Thr Val Lys Ser Phe Phe Asp
```

```
                305                 310                 315                 320
Ala Asn Leu Ala Leu Thr Glu Gln Pro Pro Lys Phe Glu Phe Tyr Asp
                    325                 330                 335

Pro Lys Thr Pro Phe Tyr Thr Ser Pro Arg Phe Leu Pro Pro Ser Lys
                    340                 345                 350

Val Glu Lys Cys Arg Ile Val Asp Ala Ile Ser His Gly Cys Phe
                    355                 360                 365

Leu Arg Glu Cys Ser Val Glu His Ser Ile Val Gly Val Arg Ser Arg
            370                 375                 380

Leu Glu Tyr Gly Val Glu Leu Lys Asp Thr Met Met Met Gly Ala Asp
385                 390                 395                 400

Tyr Tyr Gln Thr Glu Ser Glu Ile Ala Ser Leu Leu Ala Glu Gly Lys
                405                 410                 415

Ile Pro Ile Gly Ile Gly Glu Asn Thr Lys Ile Arg Asn Cys Ile Ile
                420                 425                 430

Asp Lys Asn Ala Arg Ile Gly Arg Asn Val Val Ile Ala Asn Ser Asp
            435                 440                 445

Asp Val Gln Glu Ala Asp Arg Pro Glu Asp Gly Phe Tyr Ile Arg Ser
        450                 455                 460

Gly Ile Thr Val Thr Leu Lys Asn Ala Thr Ile Lys Asp Gly Thr Ile
465                 470                 475                 480

Ile

<210> SEQ ID NO 67
<211> LENGTH: 526
<212> TYPE: PRT
<213> ORGANISM: Citrullus lanatus

<400> SEQUENCE: 67

Met Val Ala Met Asp Ser Cys Phe Val Ser Leu Lys Ser Asn Thr His
1               5                   10                  15

Leu Met Lys Gly Asn Trp Gly Gly Leu Asp Arg Cys Glu Asn Gly Phe
                20                  25                  30

Tyr Gly Glu Lys Val Arg Gly Ser Phe Asn Glu Asn Ala Trp Ile Lys
            35                  40                  45

Ser Leu Lys Ser Glu Lys Lys Ala Leu Lys Leu Thr Pro Asn Val Ala
    50                  55                  60

Tyr Ala Val Ala Thr Pro Asn Ile Ser Lys Gln Pro Val Ser Ile Gln
65                  70                  75                  80

Val Pro Ser Ile Pro Lys Val Lys Ala Asn Pro Lys Asn Val Ala Ser
                85                  90                  95

Ile Ile Leu Gly Gly Gly Ala Gly Thr His Leu Phe Pro Leu Thr Arg
                100                 105                 110

Arg Ser Ala Thr Pro Ala Val Pro Val Gly Gly Cys Tyr Arg Leu Ile
            115                 120                 125

Asp Ile Pro Met Ser Asn Cys Ile Asn Ser Gly Ile Asn Lys Ile Phe
    130                 135                 140

Val Leu Thr Gln Phe Asn Ser Ala Ser Leu Asn Arg His Ile Ser Arg
145                 150                 155                 160

Thr Tyr Phe Gly Asn Gly Val Asn Phe Gly Glu Gly Phe Val Glu Val
                165                 170                 175

Leu Ala Ala Thr Gln Thr Ser Gly Glu Thr Gly Met His Trp Phe Gln
            180                 185                 190

Gly Thr Ala Asp Ala Val Arg Gln Phe Ile Trp Val Phe Glu Asp Ala
```

```
                195                 200                 205
Lys Asn Arg Asn Val Glu Asn Ile Leu Ile Leu Ala Gly Asp His Met
210                 215                 220

Tyr Arg Met Asp Tyr Met Asp Phe Val Gln Asn His Ile Asp Arg Asn
225                 230                 235                 240

Ala Asp Ile Ser Ile Ser Cys Ala Ala Val Gly Asp Ser Arg Ala Ser
                245                 250                 255

Asp Tyr Gly Leu Val Lys Ile Asp Ser Arg Gly Arg Ile Ile Gln Phe
                260                 265                 270

Ser Glu Lys Pro Met Gly Ala Asn Leu Ser Ala Met Arg Val Asp Thr
                275                 280                 285

Thr Ser Phe Gly Leu Ser Arg Glu Glu Ser Leu Lys Ser Pro Tyr Ile
290                 295                 300

Ala Ser Met Gly Val Tyr Val Phe Lys Thr Asp Ile Leu Leu Asn Leu
305                 310                 315                 320

Leu Lys Trp Arg Tyr Pro Thr Ser Asn Asp Phe Gly Ser Glu Ile Ile
                325                 330                 335

Pro Ala Ala Val Lys Glu His Asn Val Gln Ala Tyr Ile Phe Arg Asp
                340                 345                 350

Tyr Trp Glu Asp Ile Gly Ser Ile Lys Thr Phe Tyr Asp Ala Asn Leu
            355                 360                 365

Ala Leu Thr Glu Glu Phe Pro Lys Phe Glu Phe Tyr Asp Pro Lys Thr
370                 375                 380

Pro Ile Tyr Thr Ser Pro Arg Phe Leu Pro Pro Thr Lys Ile Asp Lys
385                 390                 395                 400

Cys Gln Ile Val Asp Ala Ile Ser His Gly Cys Phe Leu Arg Glu
                405                 410                 415

Cys Ser Val Gln His Ser Ile Val Gly Glu Arg Ser Arg Leu Asp Tyr
                420                 425                 430

Gly Val Glu Leu Lys Asp Thr Ile Met Met Gly Ala Asp Thr Tyr Gln
                435                 440                 445

Thr Glu Pro Glu Ile Ala Gly Leu Leu Ala Glu Gly Lys Val Pro Ile
450                 455                 460

Gly Ile Gly Arg Asn Thr Lys Ile Arg Asn Cys Ile Ile Asp Lys Asn
465                 470                 475                 480

Ala Lys Ile Gly Lys Asp Val Val Ile Met Asn Lys Glu Gly Val Gln
                485                 490                 495

Glu Ala Asp Arg Pro Glu Gln Gly Phe Tyr Ile Arg Ser Gly Ile Thr
                500                 505                 510

Ile Ile Leu Glu Lys Ala Thr Ile Glu Asp Gly Thr Val Ile
            515                 520                 525

<210> SEQ ID NO 68
<211> LENGTH: 525
<212> TYPE: PRT
<213> ORGANISM: Cucumis melo

<400> SEQUENCE: 68

Met Val Ala Met Asp Ser Cys Phe Val Ser Leu Lys Ser Asn Thr Gln
1               5                   10                  15

Leu Met Lys Gly Asn Trp Gly Gly Leu Asp Arg Cys Glu Asn Gly Phe
                20                  25                  30

Met Val Glu Lys Val Arg Gly Gly Phe Asn Glu Asn Val Trp Ile Lys
            35                  40                  45
```

-continued

Ser Leu Lys Tyr Glu Lys Lys Ala Leu Lys Leu Thr Pro Asn Val Ala
50                  55                  60

Tyr Ala Val Thr Pro Asn Val Ser Lys Gln Pro Met Thr Ile Gln Val
65                  70                  75                  80

Pro Thr Val Pro Lys Val Lys Ala Asn Pro Lys Asn Val Ala Ser Ile
            85                  90                  95

Ile Leu Gly Gly Gly Ala Gly Thr His Leu Phe Pro Leu Thr Lys Arg
                100                 105                 110

Ser Ala Thr Pro Ala Val Pro Ala Gly Gly Cys Tyr Arg Leu Ile Asp
            115                 120                 125

Ile Pro Met Ser Asn Cys Ile Asn Ser Gly Ile Asn Lys Ile Phe Val
130                 135                 140

Leu Thr Gln Phe Asn Ser Ala Ser Leu Asn Arg His Ile Ser Arg Thr
145                 150                 155                 160

Tyr Phe Gly Asn Gly Val Thr Phe Lys Glu Gly Phe Val Glu Val Leu
                165                 170                 175

Ala Ala Thr Gln Thr Ser Gly Glu Ser Gly Met Tyr Trp Phe Gln Gly
            180                 185                 190

Thr Ala Asp Ala Val Arg Gln Phe Ile Trp Val Phe Glu Asp Ala Lys
            195                 200                 205

Asn Arg Asn Val Glu Asn Ile Leu Ile Leu Ala Gly Asp His Met Tyr
210                 215                 220

Arg Met Gly Tyr Met Asp Phe Val Gln Asn His Ile Asp Arg Asn Ala
225                 230                 235                 240

Asp Ile Ser Ile Ser Cys Ala Ala Val Asp Asp Ser Arg Ala Ser Asp
                245                 250                 255

Tyr Gly Leu Val Lys Leu Asp Ser Arg Gly Arg Ile Ile Gln Phe Ser
            260                 265                 270

Glu Lys Pro Lys Gly Ala Asn Leu Asn Arg Met Arg Val Asp Thr Thr
            275                 280                 285

Ser Phe Gly Leu Ser Arg Glu Glu Ser Leu Lys Ser Pro Tyr Ile Gly
290                 295                 300

Ser Met Gly Val Tyr Val Phe Lys Thr Asp Val Leu Leu Asn Leu Leu
305                 310                 315                 320

Lys Trp Arg Tyr Pro Ser Ser Asn Asp Phe Gly Ser Glu Ile Ile Pro
                325                 330                 335

Ala Ala Ile Lys Asp His Asn Val Gln Ala Phe Met Phe Arg Asp Tyr
            340                 345                 350

Trp Glu Asp Ile Gly Thr Ile Lys Thr Phe Tyr Asp Ala Asn Leu Ala
            355                 360                 365

Leu His Gly Asn Val Ser Lys Phe Glu Phe Tyr Asp Pro Lys Thr Pro
370                 375                 380

Phe Tyr Thr Ser Pro Arg Phe Leu Pro Pro Thr Lys Ile Asp Arg Cys
385                 390                 395                 400

Gln Ile Val Asp Ala Ile Ile Ser His Gly Cys Phe Leu Arg Glu Cys
                405                 410                 415

Ser Ile Gln His Ser Ile Val Gly Glu Arg Ser Arg Leu Asp Tyr Gly
            420                 425                 430

Val Glu Leu Lys Asp Thr Ile Met Met Gly Ala Asp Asn Tyr Gln Thr
            435                 440                 445

Glu Ser Glu Ile Thr Gly Leu Leu Ala Glu Gly Lys Val Pro Val Gly
450                 455                 460

Ile Gly Pro Asn Thr Lys Ile Arg Lys Cys Ile Ile Asp Lys Asn Ala

```
            465                 470                 475                 480
Lys Ile Gly Lys Asp Val Ile Met Asn Lys Asp Gly Val Gln Glu
                485                 490                 495
Ala Asp Arg Pro Glu Gln Gly Phe Tyr Ile Arg Ser Gly Ile Thr Ile
                500                 505                 510
Val Met Glu Lys Ala Thr Ile Glu Asp Gly Thr Val Ile
                515                 520                 525

<210> SEQ ID NO 69
<211> LENGTH: 518
<212> TYPE: PRT
<213> ORGANISM: Cucumis melo

<400> SEQUENCE: 69

Met His Lys Ile Ser Ser Gln Glu Lys Asn Gln Cys Phe Gly Phe Trp
1               5                   10                  15
Gly Asp Ser Ser Leu Gly Arg Asn Gly Arg Trp Lys Gln Ile Gln Arg
                20                  25                  30
Asn Ala Ser Ser Arg Asn Asn Ser Asp Ser Ser Ser Ser Arg Ala
            35                  40                  45
Arg Ser Leu His Pro Glu Leu Leu Ile Leu Phe Ser Cys Ser Glu Val
    50                  55                  60
Asn Glu Glu Thr Thr Thr Leu Gln Ala Pro Ile Phe Glu Ala Pro Arg
65                  70                  75                  80
Ala Asp Pro Lys Lys Val Ala Ser Ile Ile Leu Gly Gly Ala Gly
                85                  90                  95
Thr Arg Leu Phe Pro Leu Thr Ser Gln Arg Ala Lys Pro Ala Val Pro
                100                 105                 110
Ile Gly Gly Cys Tyr Arg Leu Ile Asp Ile Pro Met Ser Asn Cys Ile
                115                 120                 125
Asn Ser Gly Ile Glu Lys Ile Ser Ser Asn Ala Val Asn Ser Phe Ser
            130                 135                 140
Leu Asn Arg His Leu Ala Arg Ile Tyr Asn Phe Gly Asn Gly Val Asn
145                 150                 155                 160
Phe Gly Asp Gly Phe Val Glu Val Leu Ala Ala Thr Gln Thr Ser Gly
                165                 170                 175
Glu Thr Gly Lys Lys Trp Phe Gln Gly Thr Ala Asp Ala Val Arg Pro
                180                 185                 190
Phe Ile Trp Leu Phe Glu Asp Ala Gln Thr Lys Asn Val Glu His Thr
                195                 200                 205
Leu Ile Leu Ser Gly Asp His Leu Tyr Arg Met Asp Tyr Met Asp Phe
            210                 215                 220
Val Gln Arg His Ile Asp Thr Asn Ala Asp Ile Thr Val Ser Cys Ile
225                 230                 235                 240
Pro Met Asp Asp Ser Arg Ala Ser Asp Tyr Gly Leu Met Lys Ile Asp
                245                 250                 255
Asp Thr Gly Arg Ile Ile His Phe Ser Glu Lys Pro Lys Gly Ser Asp
                260                 265                 270
Leu Glu Glu Met Gln Val Asp Thr Ala Val Leu Gly Leu Ser Asp Glu
                275                 280                 285
Asp Ala Arg Lys Asn Pro Tyr Ile Ala Ser Met Gly Val Tyr Ile Phe
            290                 295                 300
Arg Thr Asp Leu Leu Leu Lys Leu Leu Thr Trp Ser Tyr Pro Ala Cys
305                 310                 315                 320
```

-continued

```
Asn Asp Phe Gly Ser Glu Ile Ile Pro Ala Val Lys Asp Tyr Lys
            325                 330                 335

Val Gln Ala Tyr Leu Phe Asn Asp Tyr Trp Glu Asp Ile Gly Thr Val
        340                 345                 350

Lys Ser Phe Phe Asp Ala Asn Leu Ala Leu Thr Glu Gln Pro Pro Lys
        355                 360                 365

Phe Glu Phe Tyr Asp Pro Lys Thr Pro Phe Tyr Thr Ser Pro Arg Ser
    370                 375                 380

Cys Pro Pro Ser Lys Val Glu Lys Cys Arg Ile Val Asp Ala Ile Ile
385                 390                 395                 400

Ser His Gly Cys Phe Leu Arg Glu Cys Thr Val Glu Pro Leu Ile Val
            405                 410                 415

Gly Val Arg Ser Arg Leu Glu Tyr Gly Val Glu Leu Lys Asp Thr Met
        420                 425                 430

Met Met Gly Ala Tyr Tyr Gln Thr Glu Ser Glu Ile Ala Ser Leu
        435                 440                 445

Leu Ala Glu Gly Lys Ile Pro Ile Gly Ile Gly Glu Asn Thr Lys Ile
    450                 455                 460

Arg Asn Cys Ile Ile Asp Lys Asn Ala Lys Ile Gly Arg Asn Val Val
465                 470                 475                 480

Ile Ala Asn Thr Asp Asp Val Gln Glu Ala Asp Arg Pro Glu Glu Gly
            485                 490                 495

Phe Tyr Ile Arg Ser Gly Ile Thr Val Thr Leu Lys Asn Ala Thr Ile
        500                 505                 510

Lys Asp Gly Thr Ile Ile
        515
```

<210> SEQ ID NO 70
<211> LENGTH: 516
<212> TYPE: PRT
<213> ORGANISM: Zea mays

<400> SEQUENCE: 70

```
Met Gln Phe Ala Leu Ala Leu Asp Thr Asn Ser Gly Pro His Gln Ile
1               5                   10                  15

Arg Ser Cys Glu Gly Asp Gly Ile Asp Arg Leu Glu Lys Leu Ser Ile
            20                  25                  30

Gly Gly Arg Lys Gln Glu Lys Ala Leu Arg Asn Arg Cys Phe Gly Gly
        35                  40                  45

Arg Val Ala Ala Thr Thr Gln Cys Ile Leu Thr Ser Asp Ala Cys Pro
    50                  55                  60

Glu Thr Leu His Ser Gln Thr Gln Ser Ser Arg Lys Asn Tyr Ala Asp
65                  70                  75                  80

Ala Asn Arg Val Ser Ala Ile Ile Leu Gly Gly Thr Gly Ser Gly
            85                  90                  95

Leu Phe Pro Leu Thr Ser Thr Arg Ala Thr Pro Ala Val Pro Val Gly
        100                 105                 110

Gly Cys Tyr Arg Leu Ile Asp Ile Pro Met Ser Asn Cys Phe Asn Ser
    115                 120                 125

Gly Ile Asn Lys Ile Phe Val Met Ser Gln Phe Asn Ser Thr Ser Leu
130                 135                 140

Asn Arg His Ile His Arg Thr Tyr Leu Glu Gly Gly Ile Asn Phe Ala
145                 150                 155                 160

Gly Gly Ser Val Gln Val Leu Ala Ala Thr Gln Met Pro Glu Glu Pro
            165                 170                 175
```

```
Ala Gly Trp Phe Gln Gly Thr Ala Asp Ser Ile Arg Lys Phe Ile Trp
                180                 185                 190

Val Leu Glu Asp Tyr Tyr Ser His Lys Ser Ile Asp Asn Ile Val Ile
            195                 200                 205

Leu Ser Gly Asp Gln Leu Tyr Arg Met Asn Tyr Met Glu Leu Val Gln
        210                 215                 220

Lys His Val Glu Asp Ala Asp Ile Thr Ile Ser Cys Ala Pro Val
225                 230                 235                 240

Asp Glu Ser Arg Ala Ser Lys Asn Gly Leu Val Lys Ile Asp His Thr
                245                 250                 255

Gly Arg Val Leu Gln Phe Phe Glu Lys Pro Lys Gly Ala Asp Leu Asn
            260                 265                 270

Ser Met Arg Val Glu Thr Asn Phe Leu Ser Tyr Ala Ile Asp Asp Ala
        275                 280                 285

Gln Lys Tyr Pro Tyr Leu Ala Ser Met Gly Ile Tyr Val Phe Lys Lys
    290                 295                 300

Asp Ala Leu Leu Asp Leu Leu Lys Ser Lys Tyr Thr Gln Leu His Asp
305                 310                 315                 320

Phe Gly Ser Glu Ile Leu Pro Arg Ala Val Leu Asp His Ser Val Gln
                325                 330                 335

Ala Cys Ile Phe Thr Gly Tyr Trp Glu Asp Val Gly Thr Ile Lys Ser
            340                 345                 350

Phe Phe Asp Ala Asn Leu Ala Leu Thr Glu Gln Pro Ser Lys Phe Asp
        355                 360                 365

Phe Tyr Asp Pro Lys Thr Pro Phe Phe Thr Ala Pro Arg Cys Leu Pro
    370                 375                 380

Pro Thr Gln Leu Asp Lys Cys Lys Met Lys Tyr Ala Phe Ile Ser Asp
385                 390                 395                 400

Gly Cys Leu Leu Arg Glu Cys Asn Ile Glu His Ser Val Ile Gly Val
                405                 410                 415

Cys Ser Arg Val Ser Ser Gly Cys Glu Leu Lys Asp Ser Val Met Met
            420                 425                 430

Gly Ala Asp Ile Tyr Glu Thr Glu Glu Arg Ser Lys Leu Leu Leu
        435                 440                 445

Ala Gly Lys Val Pro Ile Gly Ile Gly Arg Asn Thr Lys Ile Arg Asn
    450                 455                 460

Cys Ile Ile Asp Met Asn Ala Arg Ile Gly Lys Asn Val Val Ile Thr
465                 470                 475                 480

Asn Ser Lys Gly Ile Gln Glu Ala Asp His Pro Glu Glu Gly Tyr Tyr
                485                 490                 495

Ile Arg Ser Gly Ile Val Val Ile Leu Lys Asn Ala Thr Ile Asn Asp
            500                 505                 510

Gly Ser Val Ile
        515

<210> SEQ ID NO 71
<211> LENGTH: 21
<212> TYPE: DNA
<213> ORGANISM: Artificial sequence
<220> FEATURE:
<223> OTHER INFORMATION: Primer

<400> SEQUENCE: 71
tcgtggtgat cctgaagaat g                                             21
```

```
<210> SEQ ID NO 72
<211> LENGTH: 22
<212> TYPE: DNA
<213> ORGANISM: Artificial sequence
<220> FEATURE:
<223> OTHER INFORMATION: Primer

<400> SEQUENCE: 72
ttcgagtcat caccactttg ta                                              22
```